United States Patent [19]

Durant et al.

[11] 4,293,699

[45] Oct. 6, 1981

[54] PHARMACOLOGICALLY ACTIVE GUANIDINE COMPOUNDS

[75] Inventors: Graham J. Durant, Welwyn Garden City; John C. Emmett, Codicote; Charon R. Ganellin, Welwyn Garden City, all of England

[73] Assignee: Smith Kline & French Laboratories Limited, Welwyn Garden City, England

[21] Appl. No.: 132,605

[22] Filed: Mar. 21, 1980

Related U.S. Application Data

[60] Division of Ser. No. 948,358, Oct. 4, 1978, Pat. No. 4,228,291, which is a division of Ser. No. 764,921, Feb. 2, 1977, Pat. No. 4,137,237, which is a division of Ser. No. 637,496, Dec. 4, 1975, Pat. No. 4,022,797, which is a division of Ser. No. 450,957, Mar. 14, 1974, Pat. No. 3,950,333, which is a continuation-in-part of Ser. No. 290,584, Sep. 20, 1972, abandoned, which is a continuation-in-part of Ser. No. 230,451, Feb. 29, 1972, abandoned.

[30] Foreign Application Priority Data

Feb. 3, 1972 [IE] Ireland ................................. 136/72

[51] Int. Cl.$^3$ .................. C07C 235/04; C07C 235/06; C07C 471/02

[52] U.S. Cl. .................................. 546/121; 548/329; 548/330

[58] Field of Search .............. 548/329, 330; 546/121

[56] References Cited

U.S. PATENT DOCUMENTS

| | | | |
|---|---|---|---|
| 3,354,174 | 11/1967 | Bell | 548/330 |
| 3,718,662 | 2/1973 | Narayanan et al. | 548/329 |
| 3,838,161 | 9/1974 | Rajappa | 548/214 |
| 3,868,457 | 2/1975 | Black et al. | 424/246 X |
| 3,876,647 | 4/1975 | Durant et al. | 546/330 |
| 3,897,444 | 7/1975 | Durant et al. | 548/202 |
| 3,907,822 | 9/1975 | Narayanan et al. | 548/329 |
| 3,932,443 | 1/1976 | White | 548/342 |
| 3,950,353 | 4/1976 | Durant et al. | 548/342 |

OTHER PUBLICATIONS

C. A. 75, (1971), 118317K, Black, et al.

*Primary Examiner*—Joseph Paul Brust
*Attorney, Agent, or Firm*—Joan S. Keps; Richard D. Foggio; Alan D. Lourie

[57] ABSTRACT

The compounds are substituted thioalkyl-, aminoalkyl- and oxyalkyl-guanidines which are inhibitors of histamine activity.

7 Claims, No Drawings

PHARMACOLOGICALLY ACTIVE GUANIDINE COMPOUNDS

This is a division of application Ser. No. 948,358 filed Oct. 4, 1978, now U.S. Pat. No. 4,228,291, which is a division of application Ser. No. 764,921 filed Feb. 2, 1977, now U.S. Pat. No. 4,137,237 which is a division of application Ser. No. 637,496 filed Dec. 4, 1975, now U.S. Pat. No. 4,022,797, which is a division of application Ser. No. 450,957 filed Mar. 14, 1974, now U.S. Pat. No. 3,950,333, which is a continuation-in-part of Ser. No. 290,584 filed Sept. 20, 1972, now abandoned, which is a continuation-in-part of Ser. No. 230,451 filed Feb. 29, 1972, now abandoned.

This application relates to pharmacologically active compounds, to pharmaceutical compositions comprising these compounds and to processes for their preparation. The compounds of the invention can exist as the addition salts but, for convenience, reference will be made throughout this specification to the parent compounds.

It has long been postulated that many of the physiologically active substances within the animal body, in the course of their activity, combine with certain specific sites known as receptors. Histamine is a compound which is believed to act in such a way but, since the actions of histamine fall into more than one type, it is believed that there is more than one type of histamine receptor. The type of action of histamine which is blocked by drugs commonly called "antihistamines" (of which mepyramine is a typical example) is believed to involve a receptor which has been designated by Ash and Schild (Brit. J. Pharmac. 1966, 27,427) as H-1. The substances of the present invention are distinguished by the fact that they act as histamine H-2 receptors which, as described by Black et al. (*Nature*, 1972, 236, 385), are histamine receptors other than the H-1 receptor. Thus they are of utility in inhibiting certain actions of histamine which are not inhibited by the above-mentioned "antihistamines". The substances of this invention may also be of utility as inhibitors of certain actions of gastrin.

The compounds with which the present invention is concerned may be represented by the following general formula; insofar as tautomerism affects the compounds mentioned in this specification, the numbering of the nucleus has been modified accordingly:

FORMULA I

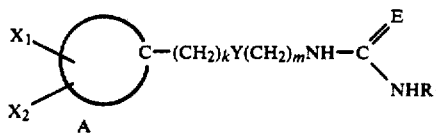

wherein A is such that there is formed together with the carbon atom shown an unsaturated heterocyclic nucleus, which comprises at least one nitrogen and may comprise a further hetero atom such as sulphur and oxygen, said unsaturated heterocyclic nucleus being an imidazole, pyrazole, pyrimidine, pyrazine, pyridazine, thiazole, isothiazole, oxazole, isoxazole, triazole, thiadiazole, benzimidazole or 5,6,7,8-tetrahydroimidazo[1,5-a]pyridine ring; $X_1$ is hydrogen, lower alkyl, hydroxyl, trifluoromethyl, benzyl, halogen, amino or

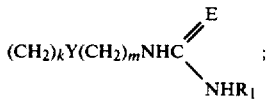

$X_2$ is hydrogen or when $X_1$ is lower alkyl, lower alkyl or halogen; k is 0 to 2 and m is 2 or 3, provided that the sum of k and m is 3 or 4; Y is oxygen, sulphur or NH; E is $NR_2$; $R_1$ is hydrogen, lower alkyl or di-lower alkylamino-lower alkyl; and $R_2$ is hydrogen, nitro or cyano or a pharmaceutically acceptable addition salt thereof. Y is preferably oxygen or sulphur, most advantageously sulphur. Preferably A is such that the nitrogen atom is adjacent to the carbon atom shown and, more preferably, such that it forms with the said carbon atom an imidazole, thiazole or isothiazole ring. Preferably, $X_1$ is hydrogen, methyl, bromo, amino or hydroxyl and $X_2$ is hydrogen. One group of preferred compounds within the present invention is that wherein Y is sulphur, k is 1, m is 2 and $R_1$ is methyl. Specific compounds which are found to be particularly useful are N-cyano-N'-methyl-N''-[2-((4-methyl-5-imidazolyl)methylthio)ethyl]guanidine, N-cyano-N'-ethyl-N''-[2-((4-methyl-5-imidazolyl)methylthio)ethyl]guanidine, N-cyano-N'-methyl-N''-[2-((4-bromo-5-imidazolyl)methylthio)ethyl]guanidine. N-cyano-N'-methyl-N''-[2-(2-thiazolylmethylthio)ethyl]guanidine and N-cyano-N'-methyl-N''-[2-(3-isothiazolylmethylthio)ethyl]guanidine.

The compounds with which the present invention is concerned wherein Y is sulphur and k is 1 or 2 may be produced by processes which commence with a substance of the following general formula:

FORMULA II

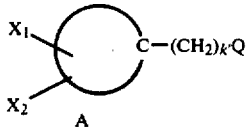

wherein A, $X_1$ and $X_2$ have the same significance as in formula I except that $X_1$ may not be

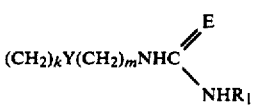

but may additionally be $(CH_2)_{k'}Q$; k' is 1 or 2 and Q is hydroxyl, halogen or methoxy. In the first stage of these processes, the compound of formula II is reacted with an amino-mercaptan of the following FORMULA III:

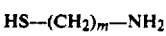

$$HS-(CH_2)_m-NH_2$$

wherein m has the same significance as in formula I. When Q is halogen, this reaction may be carried out under strongly basic conditions, for example in the presence of sodium ethoxide or sodium hydroxide. Since the substance of formula III is a primary amine it may be necessary to protect the amino group, for example by a phthalimido group which may subsequently be removed by acid hydrolysis or by hydrazinolysis. When Q is hydroxyl or halogen it is found that the reaction will take place under acidic conditions e.g. in the presence of a halogen acid such as 48% aqueous hydrogen bromide, or a halogen acid in the presence of glacial acetic acid. When Q is methoxy, the reaction will also take place in the presence of 48% hydrogen bromide.

When k is zero, the corresponding first stage of the reaction is between a nucleus directly substituted with a thiol or a thione and, under acidic conditions, 3-aminopropanol or, under alkaline conditions, a 3-halopropylamine, the amino group being protected if required in the latter case, e.g. by a phthalimido group which may be subsequently removed by acid hydrolysis or by hydrazinolysis.

The product produced by these processes is of the following formula IV, and may, of course, be in the form of the acid addition salt:

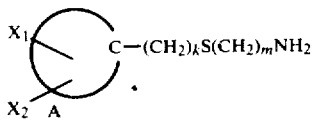

FORMULA IV wherein $X_1$ has the same significance as in formula II and A, $X_2$, k and m have the same significance as in formula I. The free base of formula IV may be obtained from the acid addition salt by treatment with an appropriate base e.g. an alkali metal alkoxide such as sodium ethoxide or an inorganic base such as potassium carbonate.

In the case of compounds of formula I wherein Y is oxygen, the process for their production commences with a compound of formula V (which may itself be formed by treatment with thionyl halide of the corresponding alcohol resulting from the reaction of a haloalkyl heterocyclic compound and the sodium salt of a diol)

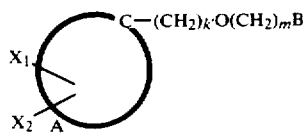

FORMULA V wherein A, $X_1$, $X_2$ and m have the same significance as in formula I, k' is 1 or 2, k'+m is 3 or 4 and B is halogen. This compound may be reacted with an alkali metal azide and the resulting product reduced, e.g. by hydrogenation over a platinum dioxide catalyst, to yield an amine of formula VI in which k is 1 or 2 and wherein A, $X_1$, $X_2$ and m have the same significance as in formula I.

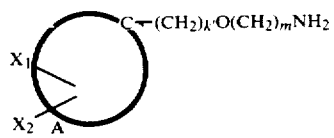

FORMULA VI

The amines of formula VI in which k is zero are prepared by reacting a halo-heterocycle under strongly basic conditions with 1,3-dihydroxypropane, converting the resultant 3-hydroxypropoxy compound with thionyl chloride to the 3-chloropropoxy compound which on reaction with sodium azide and reduction of the product yields the required amine.

The compounds of formula I wherein Y is NH are similarly formed from a compound of formula VII

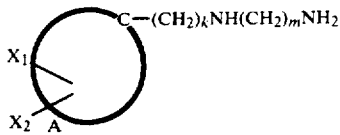

FORMULA VII wherein the amino group in the alkylene chain may be protected when k is 1 or 2 and optionally the terminal amino group may also be protected and A, $X_1$, $X_2$, k and m have the same significance as in formula I, except that $X_1$ may not be

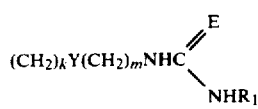

but may additionally be $(CH_2)_k Y(CH_2)_m NH_2$.

The intermediates of formula VII are prepared by a process which commences with a substance of the following general formula:

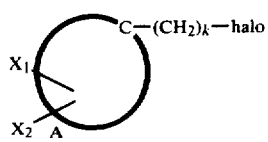

FORMULA VIII wherein A, $X_1$, $X_2$ and k have the same significance as in formula I, except that $X_1$ may not be

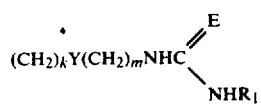

but may additionally be $(CH_2)_k$-halo. In this process, a compound of formula VIII is reacted with a diamine of the following FORMULA IX:

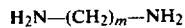

wherein m has the same significance as in formula I. This reaction may be carried out under strongly basic conditions, for example in the presence of sodium ethoxide or sodium hydroxide or in an anhydrous solvent such as dimethylformamide in the presence of sodium hydride.

The compounds of formula I are prepared from the amines of formula IV, formula VI or formula VII by treatment thereof with an isothiourea of formula X

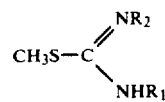

wherein $R_1$ and $R_2$ have the same significance as in formula I. The reaction is preferably carried out at elevated temperature in a solvent such as water, lower alkanol, acetonitrile or pyridine, or in the absence of a solvent when excess amine will preferably be present.

Alternatively, the compounds of formula I wherein $R_1$ is lower alkyl and $R_2$ is cyano, are prepared by reacting a thiourea of formula XI:

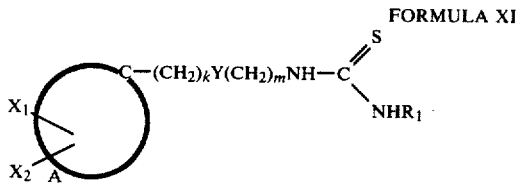

FORMULA XI wherein A, $X_1$, $X_2$, Y, k and m have the same significance as in formula I and $R_1$ is lower alkyl with a heavy metal salt of cyanamide such as the lead, mercury or cadmium salt. This process may be conveniently carried out in a solvent such as acetonitrile or dimethylformamide. In a modification of this process the thiourea of formula XI is first reacted with a desulphurising agent such as a heavy metal salt or oxide and then treated with cyanamide.

An advantageous method for the production of compounds of formula I in which $R_2$ is cyano is by the reaction of an amine of formulas IV, VI or VII with a cyanoimidodithiocarbonate or a cyanoimidocarbonate of formula XII:

$$(R_3Z)_2C=N-CN$$ FORMULA XII wherein $R_3$ is alkyl, preferably methyl, and Z is sulphur or oxygen, preferaly sulphur, to give an N-cyanoisothiourea or N-cyanoisourea of formula XIII:

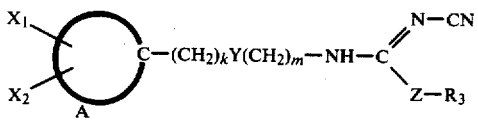

FORMULA XIII wherein A, $X_1$, $X_2$, k and m have the same significance as in formula I and Z and $R_3$ have the same significance as in formula XII. Subsequent reaction of the compounds of formula XIII with $R_1NH_2$ leads to the production of cyanoguanidines of formula I. Both stages of this reaction may be carried out in a solvent such as ethanol or isopropyl alcohol. In a modification of this method, the compound of formula XII, which in the preferred case is dimethyl-N-cyanoimidodithiocarbonate, may be reacted sequentially with an amine of formulas IV, VI or VII and with $R_1NH_2$ without isolation of the intermediate compound of formula XIII.

In an alternative method for the production of those compounds of formula I wherein $R_1$ is hydrogen and $R_2$ is cyano, an amine of formulas IV, VI or VII is reacted with a metal salt of dicyanamide of formula $MN(CN)_2$ wherein M is a metal, e.g. an alkali metal such as sodium, in an appropriate solvent and in the presence of an equivalent amount of a strong acid.

As stated above, the compounds represented by formula I have been found to have pharmacological activity in the animal body as antagonists to certain actions of histamine which are not blocked by "antihistamines" such as mepyramine. For example, they have been found to inhibit selectively the histamine-stimulated secretion of gastric acid from the perfused stomachs of rats anaesthetised with urethane, at doses of from 0.5 to 256 micromoles per kilogram intravenously. Similarly, the action of these compounds is demonstrated by their antagonism to the effects of histamine on other tissues which, according to the above-mentioned paper of Ash & Schild, are not H-1 receptors. Examples of such tissues are perfused isolated guinea-pig heart, isolated guinea-pig right atrium and isolated rat uterus. The compounds of the invention have also been found to inhibit the secretion of gastric acid stimulated by pentagastrin or by food. In addition to the above the compounds of the invention also show antiinflammatory activity in conventional tests such as the rat paw oedema test at doses of about 500 micromoles/kg. subcutaneously.

The level of activity found for the compositions comprising the compounds of the present invention is illustrated by the effective dose range in the anaesthetized rat, as mentioned above of from 0.5 to 256 micromoles per kilogram, given intravenously.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like.

A wide variety of pharmaceutical forms can be employed. Thus, if a solid carrier is used, the preparation can be tableted, placed in a hard gelatin capsule in powder or pellet form, or in the form of a troche or lozenge. The amount of solid carrier will vary widely but preferably will be from about 25 mg. to about 1 gm. If a liquid carrier is used, the preparation may be in the form of a syrup, emulsion, soft gelatin capsule, sterile injectable liquid such as an ampoule, or an aqueous or nonaqueous liquid suspension.

The pharamceutical compositions are prepared by conventional techniques involving procedures such as mixing, granulating and compressing or dissolving the ingredients as appropriate to the desired preparation.

The active ingredient will be present in the composition in an effective amount to inhibit histamine activity. The route of administration may be orally or parenterally.

Preferably, each dosage unit will contain the active ingredient in an amount of from about 50 mg. to about 250 mg., most preferably from about 100 mg. to about 200 mg.

The active ingredient will preferably be administered in equal doses one to four times per day. The daily dosage regimen will preferably be from about 150 mg. to about 1000 mg., most preferably from about 400 mg. to about 800 mg.

For therapeutic use, the pharmacologically active compounds of the present invention will normally be administered as a pharmaceutical composition comprising as the or an essential active ingredient at least one such compound in the basic form or in the form of an addition salt with a pharmaceutically acceptable acid and in association with a pharmaceutical carrier therefor. Such addition salts include those with hydrochloric hydrobromic, hydriodic, sulphuric and maleic acids.

Other pharmacologically active compounds may in certain cases be included in the composition. Advantageously the composition will be made up in a dosage unit form appropriate to the desired mode of administration, for example as a tablet, capsule, injectable solution or, when used as an anti-inflammatory agent, as a cream for topical administration.

The invention is illustrated but in no way limited by the following examples.

Compounds of formula I wherein A is such that there is formed together with the carbon atom shown a five membered unsaturated heterocyclic ring having two nitrogen atoms and three carbon atoms, said unsaturated heterocyclic ring being imidazole or pyrazole, and Y is oxygen or sulphur (sulphur is preferred) are exemplified by the following examples.

EXAMPLE 1

2-(4-Imidazolylmethylthio)ethylguanidine sulphate (i) (a) A solution of 4(5)-hydroxymethylimidazole hydrochloride (67 g.) and cysteamine hydrochloride (56.8 g.) in aqueous hydrobromic acid (1 liter 48%) was heated under reflux overnight. After cooling, the solution was evaporated to dryness and the residual solid washed with ethanol/ether to give 4(5)-[(2-aminoethyl)thiomethyl]imidazole dihydrobromide (156 g.), m.p. 178°–179°.

(b) Phthalimidoethanethiol (2 g.) was added portionwise with stirring to a solution of sodium ethoxide (prepared from 0.23 g. of sodium) in ethanol (20 ml.) at 0° under a nitrogen atmosphere. After stirring at 0° for a further 2.5 hours, the resulting yellow solution was cooled with an ice-salt bath and a solution of 4(5)-chloromethylimidazole hydrochloride (0.76 g.) in ethanol (5 ml.) was added dropwise over 10 minutes. After addition the mixture was stirred at room temperature overnight, then acidified with ethanolic hydrogen chloride and evaporated to dryness. Addition of water precipitated unreacted phthalimidoethanethiol (0.6 g.) which was removed by filtration. The filtrate was concentrated and basified with aqueous sodium bicarbonate solution to furnish a white precipitate which, on recrystallisation from aqueous ethanol, gave (4(5)-[(2-phthalimidoethyl)thiomethyl]imidazole (0.75 g.) m.p. 136°–137°. A stirred mixture of this phthalimido derivative (0.62 g.) in aqueous hydrobromic acid (40 ml. 18%) was heated under reflux overnight. After cooling to 0°, the resulting clear solution was filtered and the filtrate evaporated to dryness. Recrystallisation of the residue from ethanol gave 4(5)-[(2-aminoethyl)thiomethyl]imidazole dihydrobromide (0.52 g.), m.p. 178°–179°.

(c) A suspension of cysteamine hydrochloride (118.8 g.) in ethanol (200 ml., dried over molecular sieves) was added portionwise at 0° to a solution of sodium ethoxide (prepared from 48 g. of sodium) in ethanol (1 liter) under a nitrogen atmosphere. After stirring at 0°, for a further 2 hours, a solution of 4(5)-chloromethylimidazole hydrochloride (80 g.) in ethanol (400 ml.) was added dropwise over 45 minutes while the temperature was maintained at −1°±2°. After addition, the mixture was stirred at room temperature overnight, filtered, and the filtrate acidified with concentrated hydrochloric acid. The solution was then evaporated to dryness, the residue dissolved in ethanol (1 liter) and a solution of excess picric acid in hot ethanol added. The resulting crude picrate was dissolved in water (2.7 liters) and, after decantation from an insoluble oil, the solution was left to cool to give 4(5)-[(2-aminoethyl)thiomethyl]imidazole dipicrate, m.p. 194°–195°. Treatment of this picrate with aqueous hydrobromic acid followed by extraction with toluene gave the dihydrobromide, m.p. 178°–179°, after evaporation to dryness and recrystallisation of the crude residue from ethanol. (ii) A solution of 4(5)-[(2-aminoethyl)thiomethyl]imidazole dihydrobromide (10 g.) in water (25 ml.) was basified to pH 11 by the addition of a solution of potassium carbonate (8.7 g.) in water (25 ml.). The resulting solution was evaporated to dryness, extracted with isopropyl alcohol and the final traces of water removed by azeotroping with isopropyl alcohol. The residual amine was extracted from the inorganic material with isopropyl alcohol, the extracts concentrated to dryness to give 4-[(2-aminoethyl)thiomethyl]imidazole.

A solution of 4-[(2-aminoethyl)thiomethyl]imidazole (5.8 g.) and S-methylisothioronium sulphate (4.8 g.) in water (50 ml.) was heated under reflux for 3 hours. Following concentration to low bulk and acidification with dilute sulphuric acid, ethanol was added. The product obtained was recrystallised from aqueous methanol to give 2-(4-imidazolylmethylthio)ethylguanidine sulphate (5.2 g.), m.p. 211°–213°. (Found: C, 28.1; H, 5.1; N, 23.3; S, 21.3. $C_7H_{13}N_5S \cdot H_2SO_4$ requires: C, 28.3; H, 5.1; N, 23.6; S, 21.6).

EXAMPLE 2

(i) A solution of 4-hydroxymethyl-5-methylimidazole hydrochloride (30.0 g.) and cysteamine hydrochloride (23.0 g.) in acetic acid (200 ml.) was heated under reflux for 10 hours. Following cooling to 15°–20°, the solid which crystallised was collected and washed with isopropyl alcohol to give 4-methyl-5-[(2-aminoethyl)thiomethyl]imidazole dihydrochloride (45.5 g.), m.p. 189°–192°.

(b) A solution of 4-hydroxymethyl-5-methylimidazole hydrochloride (30.0 g.) and cysteamine hydrochloride (23.0 g.) in concentrated aqueous hydrochloride acid (450 ml.) was heated under reflux for 17 hours. Concentration followed by re-evaporation with water afforded a residue which was dissolved in isopropyl alcohol, concentrated to low bulk and cooled to afford 4-methyl-5-[(2-aminoethyl)thiomethyl]imidazole dihydrochloride (40.6 g.), m.p. 185°–191°.

(c) A mixture of 4-hydroxymethyl-5-methylimidazole hydrochloride (15.0 g.), cysteamine hydrochloride (11.5 g.) and a solution of hydrogen bromide in acetic acid (48%, 225 ml.) was heated under reflux for 7 hours. Cooling afforded 4-methyl-5-[(2-aminoethyl)thiomethyl]imidazole dihydrobromide (21.6 g.), m.p. 208°–211°.

(ii) Potassium carbonate (7.75 g.) was added to a solution of 4-methyl-5-[(2-aminoethyl)thiomethyl]imidazole dihydrochloride (14.6 g.) in water (120 ml.). The solution was stored at room temperature for 15 minutes, then evaporated to dryness, extracted with isopropyl alcohol and the extracts are concentrated to dryness to give 4-methyl-5-[(2-aminoethyl)thiomethyl]imidazole.

A solution of 4-methyl-5-[(2-aminoethyl)thiomethyl]imidazole (1.7 g.) and S-methyl-N-nitroisothiourea (1.45 g.) in methanol (35 ml.) was heated at 50°–60° for 2.5 hours and then set aside at room temperature for 48 hours. The crystalline product was filtered off and recrystallised from methanol to give N-[2-(4-methyl-5-imidazolyl)methylehio)ethyl]-N'-nitroguanidine, m.p. 184°–196°. (Found: C, 37.5; H, 5.7; N, 32.5; S, 12.5. $C_8H_{14}N_6O_2S$ requires: C, 37.2; H, 5.5; N, 32.5; S, 12.4).

(iii) Similarly reaction of N,S-dimethyl-N'-nitroisothiourea (1.6 g.) (m.p. 146°–147°, formed by the treatment of N,S-dimethylisothiouronium methosulphate with fuming nitric acid and concentrated sulphuric acid at −20°) with 4-methyl-5-[(2-aminoethyl)thiomethyl]imiazole by the above procedure followed by chromatographic purification on a column of silica gel with acetone as eluant, gives N-methyl-N'-[2-((4-methyl-5-imidazolyl)methylthio)ethyl]N''-nitroguanidine (1.23 g.), m.p. 112°–114°. (Found: C, 39.5; H, 6.2; N, 30.6; S, 11.5. $C_9H_{16}N_6O_2S$ requires: C, 39.7; H, 5.9; N, 30.9; S, 11.8).

EXAMPLE 3

(a) A solution of 4-methyl-5-[(2-aminoethyl)thiomethyl]imidazole (17.0 g.) and N-cyano-N',S-dimethylisothiourea (11.2 g.) in acetonitrile (500 ml.) was heated under reflux for 24 hours. Following concentration, the residue was chromatographed on a column of silica gel with acetonitrile as eluant and the product obtained was finally recrystallised from acetonitrile-ether to yield N-cyano-N'-methyl-N''-[2-((4-methyl-5-imidazolyl)methylthio)ethyl]guanidine, m.p. 141°–2°. (Found: C, 47.2; H, 6.4; N, 33.4; S, 12.4. $C_{10}H_{16}N_6S$ requires: C, 47.6; H, 6.4; N, 33.3; S, 12.7).

(b) (i) Potassium carbonate (7.75 g.) was added to a solution of 4-methyl-5-[(2-aminoethyl)thiomethyl]imidazole dihydrochloride (14.6 g.) in water (120 ml.). The solution was stirred at room temperature for 15 minutes and methyl isothiocyanate (5.15 g.) was added. After heating under reflux for 30 minutes, the solution was slowly cooled to 5°. The product (13.1 g.) was collected and recrystallised from water to give N-methyl-N'-[2-((4-methyl-5-imidazolyl)methylthio)ethyl]thiourea, m.p. 150°–152°.

(ii) Lead cyanamide (3.0 g.) was added to a solution of N-methyl-N'-[2-((4-methyl-5-imidazolyl)methylthio)ethyl]thiourea (2.44 g.) in acetonitrile (50 ml.). Dimethylformamide (20 ml.) was added subsequently and the suspension was heated under reflux, with stirring, for 24 hours. Filtration, followed by concentration under reduced pressure and purification of the product by chromatography on a column of silica gel with acetonitrile as eluant and recrystallisation from the same solvent afforded N-cyano-N'-methyl-N''-[2-((4-methyl-5-imidazolyl)methylthio)ethyl]guanidine, m.p. 139°–141°. (Found: C, 47.3; H, 6.6; N, 33.4; S, 12.6. $C_{10}N_{16}N_6S$ requires: C, 47.6; H, 6.4; N, 33.3; S, 12.7).

(c) (i) A solution of 4-methyl-5-[(2-aminoethyl)thiomethyl]imidazole (23.4 g.) in ethanol was added slowly to a solution of dimethyl-N-cyanoimidodithiocarbonate (20.0 g.) in ethanol, with stirring at room temperature. The mixture was set aside overnight at room temperature. Filtration afforded N-cyano-N'-[2-((4-methyl-5-imidazolyl)methylthio)ethyl]-S-methylisothiourea (10.0 g.), m.p. 148°–150°. The filtrate was concentrated under reduced pressure and the mixture was triturated with cold water and the solid obtained, filtered off and recrystallised twice from isopropyl alcohol/ether to yield further product (27 g.), m.p. 148°–150°. (Found: C, 44.4; H, 5.6; N, 26.0; S, 24.3. $C_{10}H_{14}N_5S_2$ requires: C, 44.6; H, 5.6; N, 26.0; S, 23.8).

(ii) A solution of methylamine in ethanol (33%, 75 ml.) was added to a solution of N-cyano-N'-]2-((4-methyl-5-imidazolyl)methylthio)ethyl]-S-methylisothiourea (10.1 g.) in ethanol (30 ml.). The reaction mixture was set aside at room temperature for 2.5 hours. Following concentration under reduced pressure, the residue was recrystallised twice from isopropyl alcohol/petroleum ether, affording N-cyano-N'-methyl-N''-[2-((4-methyl-5-imidazolyl)methylthio)ethyl]guanidine (8.6 g.), m.p. 141°–143°. (Found: C, 47.5; H, 6.3; N, 33.2; S, 12.9. $C_{10}H_{16}N_6S$ requires: C, 47.6; H, 6.4; N, 33.3; S, 12.7).

(d) A solution of 4-methyl-5-[(2-aminoethyl)thiomethyl]imidazole (1.93 g.) and dimethyl-N-cyanoimidodithiocarbonate (1.65 g.) in ethanol (33 ml.) was set aside overnight at room temperature. Ethanolic methylamine (33%, 22 ml.) was added and the solution was then set aside for 4 hours. Concentration and recrystallisation from isopropyl alcoholether yielded N-cyano-N'-methyl-N''-[2-((4-methyl-5-imidazolyl)methylthio)ethyl]guanidine (2.0 g.), m.p. 139°–140°. (Found: C, 47.5; H, 6.5; N, 33.3; S, 12.7. $C_{10}H_{16}N_6S$ requires: C, 47.6; H, 6.4; N, 33.3; S, 12.7).

(e) When N-cyano-N'-methyl-N''[2-((4-methyl-5-imidazolyl)methylthio)ethyl]guanidine is treated with concentrated hydrochloric acid at 100° for 4 hours, the product which is recrystallised from ethanol-ether is N-methyl-N'-[2-((4-methyl-5-imidazolyl)methylthio)ethyl]guanidine dihydrochloride, m.p. 204°–206°. (Found: C, 35.8; H, 6.5; N, 22.7; S, 10.8; Cl, 23.7. $C_9H_{17}N_5S.2HCl$ requires: C, 36.8; H, 6.4; N, 23.3; S, 10.7; Cl, 23.6).

EXAMPLE 4

N-Cyano-N'-ethyl-N''-[2-((4-methyl-5-imidazolyl)methylthio)ethyl]guanidine (a) Anhydrous ethylamine (9.0 g.) was added to a solution of N-cyano-N'-[2-((4-methyl-5-imidazolyl)methylthio)ethyl]-S-Methylisothiourea (Example 3(c), 5.0 g.) in ethanol. The solution was heated under reflux for 8 hours and concentrated under reduced pressure. The residue was dissolved in isopropyl alcohol, filtered, and diluted with water. The white solid obtained was recrystallised from isopropyl alcohol-ether to yield N-cyano-N'-ethyl-N''-[2-((4-methyl-5-imidazolyl)methylthio)ethyl]guanidine, m.p. 118°–120°. (Found: C, 49.6; H, 6.8; N, 31.2; S, 11.7. $C_{11}H_{18}N_6S$ requires: C, 49.6; H, 6.8; N, 31.6; S, 12.0).

(b) (i) A solution of 4-methyl-5-[(2-aminoethyl)thiomethyl]-imidazole (6.9 g.) and ethyl isothiocyanate (3.84 g.) in ethanol was heated under reflux for 2 hours. Concentration followed by recrystallisation of the residue from aqueous ethanol gave N-ethyl-N'-[2-((4-methyl-5-imidazolyl)methylthio)ethyl]thiourea (9.0 g.), m.p. 140°–141°. (Found: C, 46.5; H, 7.1; N, 21.7; S, 25.1. $C_{10}H_{18}N_4S_2$ requires: C, 46.5; H, 7.0; N, 21.7; S, 24.8).

(ii) Reaction of the thiourea with excess lead cyanamide by a procedure similar to that described in Example 3(b) afforded N-cyano-N'-ethyl-N''-[2-((4-methyl-5-imidazolyl)-methylthio)ethyl]guanidine, comparable with that described in Example 4(a).

EXAMPLE 5

N-Cyano-N'-[2-((4-methyl-5-imidazolyl)methylthio)ethyl]-guanidine

A solution of N-cyano-N'-[2-((4-methyl-5-imidazolyl)methylthio)ethyl]-S-methylisothiourea (2.69 g.) in saturated ammoniacal ethanol (100 ml.) was heated in a pressure vessel for 16 hours at 95°. Following concentration, the residue was chromatographed on a column of silica gel with ethyl acetate as eluant and finally recrystallised from acetonitrile to give N-cyano-N'-[2-((4-methyl-5-imidazolyl)methylthio)ethyl]guanidine (0.9 g.), m.p. 125°–127°. (Found: C, 45.2; H, 5.9; N, 35.1; S, 13.3. $C_9H_{14}N_6S$ requires: C, 45.4; H, 5.9; N, 35.3; S, 13.5).

EXAMPLE 6

N-[2-((4-Bromo-5-imidazolyl)methylthio)ethyl]-N'-cyano-N''-methylguanidine

The sequential reaction of dimethyl-N-cyanoimidodithiocarbonate (0.99 g.) with 4-bromo-5-[(2-aminoethyl)thiomethyl]imidazole (1.6 g.), prepared by the procedures of Example 1, and excess methylamine by the procedure described in Example 3(d) afforded N-[2-((4-bromo-5-imidazolyl)methylthio)ethyl]-N'-cyano-N''-methylguanidine (1.45 g.), m.p. 144°–146° (from nitromethane). (Found: C, 34.3; H, 4.2; N, 26.7; S, 10.1. $C_9H_{13}BrN_6S$ requires: C, 34.1; H, 4.1; N, 26.5; S, 10.2).

EXAMPLE 7

N-Cyano-N'-[2-(4-imidazolylmethylthio)ethyl]-N''-methylguanidine

A solution of 4(5)-[(2-aminoethyl)thiomethyl]imidazole dihydrobromide (10 g.) in water (25 ml.) was basified to pH 11 by the addition of a solution of potassium carbonate (8.7 g.) in water (25 ml.). The resulting solution was evaporated to dryness, extracted with isopropyl alcohol and the final traces of water removed by azeotroping with isopropyl alcohol. The residual amine was extracted from the inorganic material with isopropyl alcohol, the extracts concentrated to about 70 ml. and a solution of methyl isothiocyanate (2.3 g.) in isopropyl alcohol (5 ml.) added. The reaction mixture was then heated under reflux for 1.5 hours and, after cooling, evaporated to dryness. The residual oil was dissolved in acetone, the solution filtered to remove traces of inorganic material, and the filtrate concentrated to give N-methyl-N'-[2-(4-imidazolylmethylthio)ethyl]thiourea (4.1 g.), m.p. 96°–98°. A sample, recrystallised from acetone, had m.p. 98°–99°.

Lead cyanamide (24.7 g.) was added to a solution of N-methyl-N'-[2-(4-imidazolylmethylthio)ethyl]thiourea (11.5 g.) in acetonitrile (250 ml.) containing dimethylformamide. The stirred suspension was heated under reflux for 48 hours. Filtration followed by concentration under reduced pressure and purification of the product on a column of silica gel with ethyl acetate-isopropyl alcohol (2.1) as eluant gave N-cyano-N''-[2-(4-imidazolylmethylthio)ethyl]-N'-methylguanidine (3.7 g.), m.p. 138°–140° (from acetonitrile). (Found: C, 45.7; H, 5.9; N, 35.5; S, 13.5. $C_9H_{14}N_6S$ requires: C, 45.4; H, 5.9; N, 35.3; S, 13.5).

EXAMPLE 8

N-Cyano-N'-methyl-N''-[3-((4-methyl-5-imidazolyl)methylthio)propyl]guanidine (i) A solution of homocysteamine hydrochloride (22.0 g.) and 4-hydroxymethyl-5-methylimidazole hydrochloride (25.6 g.) in aqueous hydrobromic acid (500 ml.) was heated under reflux for one hour. Concentration under reduced pressure, followed by recrystallisation from methanol-isopropyl alcohol afforded 4-methyl-5-[(3-aminopropyl)thiomethyl]-imidazole dihydrobromide (24.5 g.), m.p. 200.5°–202.5°.

(ii) The reaction of 4-methyl-5-[(3-aminopropyl)thiomethyl]imidazole (from the dihydrobromide, 20.0 g.) with methyl isothiocyanate (4.5 g.) in isopropyl alcohol afforded N-methyl-N''-[3-((4-methyl-5-imidazolyl)methylthio)propyl]thiourea, m.p. 104.5°–105.5° (from methyl ethyl ketone). (Found: C, 46.6; H, 7.0; N, 21.7; S, 24.6. $C_{10}H_{18}N_4S_2$ requires: C, 46.5; H, 7.0; N, 21.7; S, 24.8).

(iii) The reaction of N-methyl-N'-[3-((4-methyl-5-imidazolyl)methylthio)propyl]thiourea (5.9 g.) with lead cyanamide (17.5 g.) by a procedure similar to that described in Example 3(b) afforded N-cyano-N'-methyl-N''- [3-((4-methyl-5-imidazolyl)methylthio)propyl]guanidine (0.91 g.), m.p. 156°–158°, following chromatography on silica gel with successive elution by chloroformethyl acetate (1:1), ethyl acetate and ethyl acetate isopropyl alcohol (5:1) and final recrystallisation from isopropyl alcohol-ether. (Found: C, 49.5; H, 7.0; S, 12.0. $C_{11}H_{18}N_6S$ requires: C, 49.6; H, 6.8; S, 12.0).

EXAMPLE 9

N-Cyano-N'-[2-((4-methyl-5-imidazolyl)methylthio)ethyl]-N''-propylguanidine

A solution of N-cyano-N'-[2-((4-methyl-5-imidazolyl)methylthio)ethyl]-S-methylisothiourea (2.69 g.) and n-propylamine (1.1 g.) in ethanol (50 ml.) was heated under reflux for 6 hours. Concentration, followed by chromatographic purification on a column of silica gel with ethyl acetate-isopropyl alcohol (4:1) as eluant and final recrystallisation from aqueous isopropyl alcohol afforded N-cyano-N'-[2-((4-methyl-5-imidazolyl)methylthio)ethyl]-N''-propylguanidine (2.0 g.) m.p. 108°–110°. (Found: C, 51.4; H, 7.4; N, 30.0; S, 11.4. $C_{12}H_{20}N_6S$ requires: C, 51.4: H, 7.2; N, 30.0; S, 11.4).

EXAMPLE 10

By the procedure of Example 1, the following amines were prepared:

2-[(2-aminoethyl)thiomethyl]imidazole
1-methyl-2-[(2-aminoethyl)thiomethyl]imidazole
2-methyl-4-[(2-aminoethyl)thiomethyl]imidazole
1-methyl-4-[(2-aminoethyl)thiomethyl]imidazole
1,5-dimethyl-2-[(2-aminoethyl)thiomethyl]imidazole
5-chloro-1-methyl-2-[(2-aminoethyl)thiomethyl]-imidazole.

The above amines were reacted with dimethyl-N-cyanoimidodithiocarbonate and then with methylamine by the procedure of Example 3(c) to give the following products, respectively:

N-cyano-N'-[2-(2-imidazolylmethylthio)ethyl]-N''-methylguanidine
N-cyano-N'-methyl-N''[2-((1-methyl-2-imidazolyl)methylthio)ethyl]guanidine
N-cyano-N'-methyl-N''-[2-((2-methyl-4-imidazolyl)methylthio)ethyl]guanidine
N-cyano-N'-methyl-N''-[2-((1-methyl-4-imidazolyl)methylthio)ethyl]guanidine
N-cyano-N'-[2-((1,5-dimethyl-2-imidazolyl)methylthio)ethyl]-N''-methylguanidine
N-[2-((5-chloro-1-methyl-2-imidazolyl)methylthio)ethyl]-N'-cyano-N''-methylguanidine.

EXAMPLE 11

N-Cyano-N'-methyl-N''-[2-(4-trifluoromethyl-5-imidazolylmethylthio)ethyl]guanidine A mixture of ethyl 2-chloro-4,4,4-trifluoroacetate (65.7 g.), distilled formamide (135 g.) and water (11 ml.) was heated at 128°–130° for 1.5 hours. After cooling, an equal volume of ice-cold water was added to give 4-trifluoromethyl-5-carbethoxyimidazole, m.p. 184°–186° (from aqueous methanol).

Reduction of the ester (9.4 g.) with lithium aluminium hydride (2.4 g.) in tetrahydrofuran gave 5-hydroxymethyl-4-trifluoromethylimidazole, isolated as its picrate, m.p. 135.5°–137.5° (from aqueous isopropyl alcohol).

The picrate (5.3 g.) was dissolved in 48% aqueous hydrobromic acid and extracted with toluene to remove picric acid. Cysteamine hydrochloride (1.52 g.) was added to the aqueous phase and the acidic solution heated under reflux for 12 hours. Concentration and trituration of the residue with ethanol-ether gave 4-trifluoromethyl-5-[(2-aminoethyl)thiomethyl]imidazole dihydrobromide (3.2 g.), m.p. 179°–182°. Basification followed by treatment with dimethyl-N-cyanoimidodithiocarbonate and then with methylamine by the procedure of Example 3(c) gives the title compound.

EXAMPLE 12

N-Cyano-N'-[2-(4-imidazolylmethoxy)ethyl]-N"-methylguanidine

A stirred suspension of 4-(2-chloroethoxymethyl)imidazole hydrochloride (14.7 g.) and sodium size azide (9.8 g.) in dry dimethylformamide (103 ml.) was maintained at 95° for 5 hours and then set aside overnight at room temperature. Following dilution with water and filtration, the filtrate was concentrated and the residue purified by chromatography on a dry column of alumina using ethanol. The product was basified with potassium carbonate (6.5 g.) in water (3 ml.) and the anhydrous residue was extracted with isopropyl alcohol (3×50 ml.). Concentration of the extracts afforded 4-(2-azidoethoxymethyl)imidazole (7.2 g.). Hydrogenation of the azido compound (7.2 g.) in isopropyl alcohol (142 ml.) over platinum oxide catalyst (3.0 g.) gave 4-(2-aminoethoxymethyl)imidazole (6.48 g.). A sample of the monopiocrate monohydrochloide had m.p. 139°–140° (from nitromethane). (Found: c, 35.4; H, 3.8; N, 20.5; Cl, 8.8. $C_{12}H_{15}ClN_6O_8$ requires: C, 35.4; H, 3.7; N, 20.7; Cl, 8.7).

Treatment of the above prepared amine with dimethyl-N-cyanoimidodithiocarbonate and then with methylamine by the procedure of Example 3(c) gives the title compound.

EXAMPLE 13

Sulphuryl chloride (286 g.) was added dropwise to a solution of ethyl 3-oxopentanoate (300 g.) in chloroform (250 ml.) at 10°–15°. Following addition the mixture was stirred overnight at room temperature, heated under reflux for 0.5 hour and cooled. After washing with water, sodium bicarbonate and water, the solution was dried (sodium sulphate), concentrated and fractionated to yield ethyl 2-chloro-3-oxopentanoate, b.p. 94°–96°/14 mm.

A mixture of ethyl 2-chloro-3-oxopentanoate (178 g.), freshly distilled formamide (450 g.) and water (38 ml.) was heated at 140°–148° and then cooled and added to dilute hydrochloric acid. After decanting from insoluble material, the solution was basified with ammonium hydroxide to give a solid which, following recrystallization from aqueous ethanol and ethanol - ethyl acetate, yielded 4-ethyl-5-carbethoxyimidazole (29 g.) m.p. 170°–172°. This ester (14.0 g.) was reduced with lithium aluminium hydride (4.6 g.) in tetrahydrofuran and then heated with hydrogen chloride to give 4-ethyl-5-hydroxymethylimidazole hydrochloride (10.6 g.) m.p. 141°–143° (from ispropyl alcohol-ether). This 5-hydroxymethyl compound is converted to 4-ethyl-5-[(2-aminoethyl)thiomethyl]imidazole by the procedure of Example 2.

Using the above prepared amine intermediate in the procedure of Example 3 gives N-cyano-N'-methyl-N"-[2-((4-ethyl-5-imidazolyl)methylthio)ethyl]guanidine.

Hydrolysis of the latter compound with concentrated hydrochloric acid by the method of Example 3(e) gives N-methyl-N'-[2-((4-ethyl-5-imidazolyl)methylthio)ethyl]guanidine dihydrochloride.

EXAMPLE 14

A solution of sodium nitrate (43.8 g.) in water (92 ml.) was added dropwise, with stirring, to a solution of ethyl isobutyrylacetate (100.3 g.) in acetic acid (80 ml.) at 0°. After stirring at 0° for 30 minutes then at room temperature for 3 hours, (100 ml.) was added and the mixture extracted with ether. The extracts were washed with water, saturated sodium bicarbonate solution and water. After drying (CaSO$_4$), the solution was evaporated to give ethyl 2-oximino-4-methyl-3-oxopentanoate (112 g.) as a crude oil.

A solution of this oximinoketone (219 g.) in ethanol (280 ml.) was added to a suspension of pre-reduced palladised charcoal (10 g., 10%) in ethanol (1 liter) and saturated ethanolic hydrogen chloride (512 ml.) and the mixture hydrogenated at room temperature and pressure until the theoretical amount of hydrogen was taken up. The mixture was filtered, the filtrate concentrated and ethyl acetate added to give ethyl 2-amino-4-methyl-3-oxopentanoate hydrochloride (230.6 g.) m.p. 129°–131° (dec.). This aminoketone (50.5 g.) was dissolved in redistilled formamide (180 ml.) and the solution was heated at 120° for two hours, 130° for one hour, and finally at 140° for two hours. After cooling, the mixture was filtered and the crystalline product washed with water to give ethyl 4-isopropyl-5-carbethoxy-imidazole (22 g.) m.p. 117°–178°.

This ester (108 g.) was placed in a soxhlet and reduced with lithium aluminum hydride (34.5 g.) in tetrahydrofuran to give 4-hydroxymethyl-5-isopropylimidazole (62.3 g.) m.p. 121°–123°. By the procedure of Example 2, this 4-hydroxymethyl compound was converted to the 4-[(2-aminoethyl)thiomethyl] intermediate.

Using the above prepared amine intermediate in the procedure of Example 2(iii) gives N-methyl-N'-[2-((5-isopropyl-4-imidazolyl)methylthio)ethyl]-N"-nitroguanidine.

EXAMPLE 15

N-[2-((4-Benzyl-5-imidazolyl)methylthio)ethyl]-N'-cyano-N"-methylguandine

Reaction of ethyl 3-oxo-4-phenylbutyrate (10.3 g.) with sodium nitrite followed by reduction of the crude ethyl 2-oximino-3-oxo-4-phenylbutyrate (10.8 g.) by hydrogenation gave ethyl 2-amino-3-oxo-4-phenylbutyrate hydrochloride (8.5 g.) m.p. 150°–153° C. An analytical sample, recrystallized from ethanol/ethyl acetate, had m.p. 154°–155°.

Reaction of this aminoketone (160 g.) with formamide (480 ml.) by heating at 120°–140° over five hours gave 4-benzyl-5-carbethoxyimidazole (75 g.) m.p. 168.5°–169.5°. Reduction of this ester (30 g.) with lithium aluminum hydride (6.4 g.) in tetrahydrofuran (600 ml.), followed by addition of water, filtration and acidification of the filtrate with ethanolic hydrogen chloride, gave 4-benzyl-5-hydroxymethylimidazole hydrochloride (22.9 g.), m.p. 149°–151°, after concentration and addition of ethyl acetate.

By the procedure of Example 1, the above prepared hydroxymethyl compound is converted to 5-[(2-aminoethyl)thiomethyl]-4-benzylimidazole.

Using the above prepared amine as the starting material in the procedure of Example 3(a) gives N-[2-((4-benzyl-5-imidazolyl)methylthio)ethyl]-N'-cyano-N''-methylguanidine.

EXAMPLE 16

N-Cyano-N'-(2-dimethylaminoethyl)-N''-[2-((4-methyl-5-imidazolyl)methylthio)ethyl]guanidine By the procedure of Example 4, 2-(dimethylamino)ethylamine is reacted with N-cyano-N'-[2-((4-methyl-5-imidazolyl)methylthio)ethyl]-S-methylisothiourea to give the title compound.

EXAMPLE 17

A solution of 4(5)-(2-chloroethyl)imidazole hydrochloride (13.6 g.) and cysteamine hydrochloride (9.3 g.) in distilled water (100 ml.) was added over 30 minutes to a stirred solution of potassium hydroxide (15.8 g., 85%) in water (40 ml.) at room temperature under a nitrogen atmosphere. After addition the solution was heated for 4 hours at 50°. From time to time it was necessary to add a few drops of potassium hydroxide solution to prevent the pH of the reaction mixture falling below 11. The reaction mixture was then acidified with 2 N hydrochloric acid, evaporated to dryness under reduced pressure and the final traces of water removed by azeotroping with n-propanol. The residue was extracted several times with isopropyl alcohol and the combined extracts added to a hot solution of picric acid in isopropyl alcohol. On cooling, this gave 4(5)-[2-(2-aminoethyl)thioethyl]imidazole dipicrate (42.3 g.) m.p. 225°–226°.

This dipicrate was converted to the dihydrochloride by addition of conentrated hydrochloric acid (200 ml.) followed by extraction with toluene (5×50 ml.). The aqueous solution was evaporated to dryness, the residue dissolved in water and the solution basified by the addition of aqueous potassium carbonate solution. This mixture was then evaporated to dryness and the residue extracted with n-propanol to give the crude base of 4(5)-[2-(2-aminoethyl)thioethyl]imidazole on removal of the n-propanol.

Using the above prepared amine as the starting material in the procedure of Example 3 gives N-cyano-N'-[2-(2-(4-imidazolyl)ethyl)thioethyl]-N''-methylguanidine.

Using the above prepared amine as the starting material in the procedure of Example 2(iii) gives N-methyl-N'-[2-(2-(4-imidazolyl)ethyl)thioethyl]-N''-nitroguanidine.

EXAMPLE 18

N-Cyano-N'-[2-(4-imidazolylmethylthio)ethyl]guanidine 4-((2-Aminoethyl)thiomethyl)imidazole is reacted with dimethyl-N-cyanoimidodithiocarbonate according to the procedure of Example 3(c)(i) and the resultant N-cyano-N'-[2-(4-imidazolylmethylthio)ethyl]-S-methylisothiourea treated with ammoniacal ethanol according to the procedure of Example 5 to give the title compound.

EXAMPLE 19

The reaction of 4,5-dihydroxymethylimidazole hydrochloride (1.6 g.) with cysteamine hydrochloride (2.2 g.) by the procedure described in Example 1(i)(a) afforded 4,5-bis-((2-aminoethyl)thiomethyl)imidazole trihydrobromide (3.8 g.), m.p. 223°–236° C.

Using the above prepared amine as starting material in the procedure of Example 3 gives 4,5-bis[2-(N-cyano-N'-methylguanidino)ethylthiomethyl]imidazole. Hydrolysis of this compound by the procedure of Example 3(e) gives 4,5-bis[2-(N-methylguanidino)ethylthiomethyl]imidazole trihydrochloride.

EXAMPLE 20

N-Cyano-N'-[3-(2-imidazolylthio)propyl]-N''-methylguanidine

A solution of 2-mercaptoimidazole (2 g.) and 3-aminopropanol (1.14 ml.) in hydrobromic acid (48%, 25 ml.) was heated under reflux for 25 hours. The reaction mixture was evaporated to dryness and the oily residual solid recrystallized twice from ethanol/ether to give 2-(3-aminopropylthio)imidazole dihydrobromide (3.55 g.), m.p. 160°–162°.

The above prepared dihydrobromide salt is converted to the free base and reacted with N-cyano-N',S-dimethylisothiourea by the procedure of Example 3(a) to give the title compound.

EXAMPLE 21

N-[2-((1,4-Dimethyl-2-imidazolyl)methylthio)ethyl]-N'-nitroguanidine

The reaction of 1,4-dimethylimidazole (5.65 g.) with n-butyl lithium followed by treatment with formaldehyde (according to the method described for the preparation of 3-hydroxymethyl-5,6,7,8-tetrahydroimidazo[1,5-a]pyridine in Example 243) gave 1,4-dimethyl-2-hydroxymethylimidazole (2.71 g.), m.p,. 125°–126° (ethyl acetate-petroleum ether).

The reaction of 1,4-dimethyl-2-hydroxymethylimidazole (2.5 g.) with cysteamine hydrochloride (2.5 g.) in aqueous hydrobromic acid by the method described in Example 1(i)(a) gave 1,4-dimethyl-2-[(2-aminoethyl)thiomethyl]imidazole dihydrobromide (6.2 g.), m.p. 161°–163° (from isopropyl alcohol-methanol).

Using the above prepared amine dihydrobromide as the starting material in the procedure of Example 2(ii) gives the title compound.

EXAMPLE 22

N-Cyano-N'-[3-(4-imidazolylmethoxy)propyl]-N''-methylguanidine

Sodium (13.5 g.) was added over 3 hours to propane-1,3-diol (450 ml.) under nitrogen at 70° with stirring. This solution was added over 20 minutes to a stirred solution of 4-chloromethylimidazole hydrochloride (50.0 g.) under nitrogen at 40°–60°. Subsequent heating at 60°–65° for 3 hours followed by overnight cooling, filtration and concentration gave 4-(3-hydroxypropoxy)methylimidazole. Subsequent reaction with thionyl chloride gave 4-(3-chloropropoxy)methylimidazole hydrochloride (38.3 g.).

The reaction of this chloride (36.2 g.) with sodium azide (22.4 g.) in the dry dimethylformamide at 95° for 3 hours followed by 'dry-column' chromatography on aluminium with ethanol as eluant gave 4-(3-azidopropoxy)methylimidazole which was further purified by the same method using chloroform as eluant. The azide (2.95 g.) in ethanol (200 ml.) was hydrogenated over platinum oxide catalyst to give 4-(3-aminopropoxy)methylimidazole (2.42 g.).

Using the above prepared amine as the starting material in the procedure of Example 3(c) gives the title compound.

EXAMPLE 23

N-[2-((2-Amino-4-imidazolyl)methylthio)ethyl]-N'-cyano-N''-methylguanidine

Freshly prepared sodium amalgam (90 g.) is added over 75 minutes to a stirred solution of serine ethyl ester dihydrochloride (3.0 g.) in water/ethanol (2:1), the temperature being maintained within the range of from $-20°$ to $-10°$ and the pH at about 2.5 by the addition of 5 N hydrochloric acid. After a further 45 minutes the mixture is allowed to warm to 10° and the precipitated free mercury is removed. Cyanamide is added and the mixture warmed to 50° for 30 minutes, left at 0° for 18 hours and evaporated to dryness. After washing with ether to remove any unchanged cyanamide, the residue is extracted with hot ethanol and heated with hot ethanolic picric acid. Concentration and cooling of the solution gives 2-amino-4-hydroxymethylimidazole picrate.

Reaction of 2-amino-4-hydroxymethylimidazole hydrochloride (which is obtained by treating the picrate salt with hydrochloric acid) with cysteamine hydrochloride by the procedure of Example 1 gives 2-amino-4-[(2-aminoethyl)thiomethyl]imidazole.

By the procedure of Example 3(a), 2-amino-4-[(2-aminoethyl)thiomethyl]imidazole is reacted with N-cyano-N',S-dimethylisothiourea to give the title compound.

EXAMPLE 24

| Ingredients | Amounts |
| --- | --- |
| N-Cyano-N'-methyl-N''-[2-((4-methyl-5-imidazolyl)methylthio)ethyl]guanidine | 150 mg. |
| Sucrose | 75 mg. |
| Starch | 25 mg. |
| Talc | 5 mg. |
| Stearic acid | 2 mg. |

The ingredients are screened, mixed and filled into a hard gelatin capsule.

EXAMPLE 25

| Ingredients | Amounts |
| --- | --- |
| N-[2-((4-Methyl-5-imidazoyl)methylthio)ethyl]-N'-nitroguanidine | 200 mg. |
| Lactose | 100 mg. |

The ingredients are screened, mixed and filled into a hard gelatin capsule.

EXAMPLE 26

By the procedure of Example 1, using 3-hydroxymethylpyrazole as the starting material, 2-(3-pyrazolylmethylthio)ethylguanidine sulphate is obtained.

Also, using 3-hydroxymethylpyrazole as the starting material, the procedure of Example 2(i) and (ii) gives N[2-(3-pyrazolylmethylthio)ethyl]-N'-nitroguanidine, and the procedure of Example 2(iii) gives N-methyl-N'-[2-(3-pyrazolylmethylthio)ethyl]-N''-nitroguanidine.

Using 3-[(2-aminoethyl)thiomethyl]pyrazole, prepared from 3-hydroxymethylpyrazole by the procedure of Example 1, as the starting material in the procedure of Example 3(c) gives N-cyano-N'-methyl-N''-[2-(3-pyrazolylmethylthio)ethyl]guanidine. Hydrolysis by the method of Example 3(e) gives N-methyl-N'-[2-(3-pyrazolylmethylthio)ethyl]guanidine dihydrochloride.

Reacting 3-hydroxymethylpyrazole and 3-mercaptopropylamine by the procedure of Example 1 and using the resulting 3-[(3-aminopropyl)thiomethyl]pyrazole as the starting material in the procedure of Example 3(a) gives N-cyano-N'-methyl-N''-[3-(3-pyrazolylmethylthio)propyl]guanidine.

EXAMPLE 27

Reaction of 3-[(2-aminoethyl)thiomethyl]pyrazole with dimethyl-N-cyanoimidodithiocarbonate by the procedure of Example 3(c)(i) gives N-cyano-N'-[2-(3-pyrazolylmethylthio)ethyl]-S-methylisothiourea.

Reaction of the above prepared isothiourea with anhydrous ethylamine by the procedure of Example 4(a) gives N-cyano-N'-ethyl-N''-[2-(3-pyrazolylmethylthio)ethyl]guanidine.

By the same procedure, using propylamine, N-cyano-N'-propyl-N''-[2-(3-pyrazolylmethylthio)ethyl]guanidine is prepared.

Also, by the same procedure, using 2-(dimethylamino)ethylamine, the product is N-cyano-N'-(2-dimethylaminoethyl)-N''-[2-(3-pyrazolylmethylthio)ethyl]guanidine.

EXAMPLE 28

Using, in the procedure of Example 3, the following aminoethylthiomethylpyrazoles, prepared by the procedure of Example 1 from the corresponding hydroxymethylpyrazoles:

3-[(2-aminoethyl)thiomethyl]-5-methylpyrazole
4-[(2-aminoethyl)thiomethyl]-3,5-dimethylpyrazole
3-[(2-aminoethyl)thiomethyl]-5-hydroxypyrazole
3,4-di-[(2-aminoethyl)thiomethyl]pyrazole the products are, respectively:

N-cyano-N'-methyl-N''-[2-((5-methyl-3-pyrazolyl)methylthio)ethyl]guanidine
N-cyano-N'-methyl-N''-[2-((3,5-dimethyl-4-pyrazolyl)methylthio)ethyl]guanidine
N-cyano-N'-methyl-N''-[2((5-hydroxy-3-pyrazolyl)methylthio)ethyl]guanidine
3,4-bis-[2-(N-cyano-N'-methylguanidino)ethylthiomethyl]pyrazole.

EXAMPLE 29

Using 4-hydroxy-3-hydroxymethylpyrazole (which is prepared by converting 4-hydroxy-3-pyrazolecarboxylic acid to the corresponding ethyl ester and reducing the ester with lithium aluminium hydride in tetrahydrofuran) as the starting material in the procedure of Example 3 gives N-cyano-N'-methyl-N''-[2-((4-hydroxy-3-pyrazolyl)methylthio)ethyl]guanidine. Hydrolysis of this compound by the procedure of Example 3(e) gives N-methyl-N'-[2-((4-hydroxy-3-pyrazolyl)methylthio)ethyl]guanidine hydrochloride.

EXAMPLE 30

N-Cyano-N'-methyl-N''-[2-(2-(3-pyrazolyl)ethyl)thioethyl]guanidine

By the procedure of Example 17 using 3-(2-chloroethyl)pyrazole (which is prepared by treating 3-(2-hydroxyethyl)pyrazole with thionyl chloride) as the starting material, the title compound is prepared.

EXAMPLE 31

N-Cyano-N'-methyl-N''-[3-(3-pyrazolylmethoxy)-propyl]guanidine

By the procedure of Example 22, using 3-bromomethylpyrazole (prepared by reacting 3-hydroxymethylpyrazole with thionyl bromide) as the starting material, the title compound is prepared.

EXAMPLE 32

By the procedure of Example 18, reacting 3-[(2-aminoethyl)thiomethyl]pyrazole with dimethyl-N-cyanoimidodithiocarbonate and reacting the resulting N-cyano-N'-[2-(3-pyrazolylmethylthio)ethyl]-S-methylisothiourea with ammoniacal ethanol gives N-cyano-N'-[2-(3-pyrazolylmethylthio)ethyl]guanidine.

EXAMPLE 33

| Ingredients | Amounts |
| --- | --- |
| N-Cyano-N'-methyl-N''-[2-(3-pyrazolymethylthio)ethyl]guanidine | 200 mg. |
| Lactose | 100 mg. |

The ingredients are mixed and filled into a hard gelatin capsule.

Compounds of formula I wherein A is such that there is formed together with the carbon atom shown a five membered unsaturated heterocyclic ring having two nitrogen atoms and three carbon atoms, said unsaturated heterocyclic ring being imidazole or pyrazole, and Y is NH are exemplified by the following examples.

EXAMPLE 34

2-(4(5)-Imidazolylmethylamino)ethylguanidine sulphate

4(5)-Chloromethylimidazole (1.16 g., 0.01 m.) in 10 ml. of ethanol is added slowly to excess ethylenediamine (6.0 g.) in 25 ml. of ethanol. The mixture is heated at 55° for one hour, then concentrated under reduced pressure and basified with sodium hydroxide. Evaporation under high vacuo and steam distillation followed by concentration to dryness, extraction with ethanol and acidification with ethanolic hydrogen chloride gives N-(4(5)-imidazolylmethyl)ethylenediamine.

The above prepared compound is heated under reflux with S-methylisothiouronium sulphate in water for 3 hours by the procedure of Example 1 to give the title compound.

EXAMPLE 35

Reaction of N-(4(5)-imidazolylmethyl)ethylenediamine with S-methyl-N-nitroisothiourea by the procedure of Example 2(ii) gives N-[2-(4(5)-imidazolylmethylamino)ethyl]-N'-nitroguanidine, and in the procedure of Example 2(iii) gives N-methyl-N'-[2-(4-imidazolylmethylamino)ethyl]-N''-nitroguanidine.

EXAMPLE 36

Reacting 4(5)-chloromethylimidazole with ethylenediamine by the procedure of Example 34, then reacting the resulting N-(4(5)-imidazolylmethyl)ethylenediamine with N-cyano-N',S-dimethylisothiourea in pyridine by the procedure of Example 3 gives N-cyano-N'-[2-(4(5)-imidazolylmethylamino)ethyl]-N''-methylguanidine. Hydrolysis of this compound by the procedure of Example 3(e) gives N-methyl-N'-[2-(4-imidazolylmethylamino)ethyl]guanidine trihydrochloride.

EXAMPLE 37

Ethylenediamine is reacted with 4(5)-chloromethylimidazole by the procedure of Example 34 and the resulting N-(4(5)-imidazolylmethyl)ethylenediamine is reacted with ethyl isothiocyanate by the procedure of Example 3(b) to give, after concentrating and chromatographing, N-ethyl-N'-[2-(4(5)-imidazolylmethylamino)ethyl]-thiourea. This thiourea is reacted with lead cyanamide by the procedure of Example 3(b) to give N-cyano-N'-ethyl-N''-[2-(4(5)-imidazolylmethylamino)ethyl]guanidine.

By the same procedure, using propyl isothiocyanate, N-cyano-N'-[2-(4(5)-imidazolylmethylamino)ethyl]-N''-propylguanidine is prepared.

In the same manner, using 2-dimethylaminoethyl isothiocyanate, the product is N-cyano-N'-(2-dimethylaminoethyl)-N''-[2-(4(5)imidazolylmethylamino)ethyl]guanidine.

EXAMPLE 38

N-Cyano-N'-[2-(2-(4(5)-imidazolyl)ethylamino)ethyl]-N''-methylguanidine

By the procedure of Example 34, reacting 4(5)-(2-chloroethyl)imidazole with ethylenediamine gives N-[2-(4(5)-imidazolyl)ethyl]ethylenediamine.

Reacting the above prepared intermediate with N-cyano-N',S-dimethylisothiourea by the procedure of Example 3 gives the title compound.

EXAMPLE 39

Using, in the procedure of Example 36, in place of 4(5)-chloromethylimidazole the following compounds (which may be prepared from the corresponding hydroxymethyl imidazoles by treatment with thionyl chloride):

4-chloromethyl-5-methylimidazole
4-chloromethyl-5-ethylimidazole
4-chloromethyl-5-isopropylimidazole
4-chloromethyl-5-benzylimidazole
4-chloromethyl-5-bromoimidazole
4-chloromethyl-2-methylimidazole
4-chloromethyl-1-methylimidazole
2-chloromethylimidazole
2-chloromethyl-1,5-dimethylimidazole
5-chloro-2-chloromethyl-1-methylimidazole
5-chloromethyl-4-trifluoromethylimidazole
2-amino-4-chloromethylimidazole
4,5-di(chloromethyl)imidazole
the products are, respectively:
N-cyano-N'-methyl-N''-[2-((5-methyl-4-imidazolyl)methylamino)ethyl]guanidine
N-cyano-N'-[2-((5-ethyl-4-imidazolyl)methylamino)ethyl]-N''-methylguanidine N-cyano-N'-[2-((5-isopropyl-4-imidazolyl)methylamino)ethyl]-N"-methylguanidine
N-cyano-N'-[2-((5-benzyl-4-imidazolyl)methylamino)ethyl]-N"-methylguanidine
N-cyano-N'-[2-((5-bromo-4-imidazolyl)methylamino)ethyl]-N"-methylguanidine
N-cyano-N'-methyl-N"-[2-((2-methyl-4-imidazolyl)methylamino)ethyl]]guanidine
N-cyano-N'-methyl-N"-[2-((1-methyl-4-imidazolyl)methylamino)ethyl]]guanidine
N-cyano-N'-[2-(2-imidazolylmethylamino)ethyl]-N"-methylguanidine
N-cyano-N'-methyl-N"-[2-((1,5-dimethyl-2-imidazolyl)methylamino)ethyl]guanidine
N-cyano-N'-[2-((5-chloro-1-methyl-2-imidazolyl)methylamino)ethyl]-N"-methylguanidine
N-cyano-N'-methyl-N"-[2-((4-trifluoromethyl-5-imidazolyl)methylamino)ethyl]guanidine
N-[2-((2-amino-4-imidazolyl)methylamino)ethyl]-N'-cyano-N"-methylguanidine
4,5-bis-[2-(N-cyano-N'-methylguanidino)ethylaminomethyl]imidazole.

EXAMPLE 40

The reaction of 8.3 g. (0.1 m.) of 2-aminoimidazole and 13.3 g. (0.1 m.) of β-azidopropionyl chloride in pyridine gives 2-(β-azidopropionyl)imidazole. Reduction of this compound with diborane in ethylene glycol/dimethyl ether yields 2-(3-aminopropylamino)imidazole.

Using 2-(3-aminopropylamino)imidazole as the starting material in the procedure of Example 3(b) gives N-cyano-N'-[3-(2-imidazolylamino)propyl]-N"-methylguanidine.

Reacting the above prepared compound with hydriodic acid gives the hydroiodide salt.

EXAMPLE 41

Using 2-(3-aminopropylamino)imidazole as the starting material in the procedure of Example 18 gives N-cyano-N'-[3-(2-imidazolylamino)propyl]-S-methylisothiourea. Treating this compound with ammoniacal ethanol by the procedure of Example 18 gives N-cyano-N'-[3-(2-imidazolylamino)propyl]guanidine.

EXAMPLE 42

| Ingredients | Amounts |
|---|---|
| N-Cyano-N'-methyl-N"-[2-((5-methyl-4-imidazolyl)methylamino)ethyl]guanidine | 150 mg. |
| Lactose | 100 mg. |

The ingredients are screened and filled into a hard gelatin capsule.

EXAMPLE 43

Reaction of 3-bromomethylpyrazole, prepared by treatment of 3-hydroxymethylpyrazole with thionyl bromide, with ethylenediamine by the procedure of Example 34 gives N-(3-pyrazolylmethyl)ethylenediamine.

The above prepared compound is heated under reflux with S-methylisothiouronium sulphate in water for 3 hours by the procedure of Example 1 to give 2-(3-pyrazolylmethylamino)ethylguanidine sulphate.

EXAMPLE 44

Reaction of N-(3-pyrazolylmethyl)ethylenediamine with S-methyl-N-nitroisothiourea by the procedure of Example 2(ii) gives N-nitro-N'-[2-(3-pyrazolylmethylamino)ethyl]guanidine, and in the procedure of Example 2(iii) gives N-methyl-N'-[2-(3-pyrazolylmethylamino)ethyl]-N"-nitroguanidine.

EXAMPLE 45

Reacting 3-bromomethylpyrazole with ethylenediamine by the procedure of Example 34 and reacting the resulting N-(3-pyrazolylmethyl)ethylenediamine with N-cyano-N',S-dimethylisothiourea by the procedure of Example 3(d) gives N-cyano-N'-methyl-N"-[2-(3-pyrazolylmethylamino)ethyl]guanidine. Hydrolysis of this compound by the procedure of Example 3(e) gives N-methyl-N'-[2-(3-pyrazolylmethylamino)ethyl]guanidine trihydrochloride.

By the procedure of Example 3(b), reacting N-(3-pyrazolylmethyl)ethylenediamine with ethyl isothiocyanate, then reacting the resulting N-ethyl-N'-[2-(3-pyrazolylmethylamino)ethyl]thiourea with lead cyanamide gives N-cyano-N'-ethyl-N"-[2-(3-pyrazolylmethylamino)ethyl]guanidine. By the same procedure, using propyl isothiocyanate the corresponding N'-propyl compound is prepared. Also, by the same procedure, using 2-dimethylaminoethyl isothiocyanate, the product is N-cyano-N'-(2-dimethylaminoethyl)-N"-[2-(3-pyrazolylmethylamino)ethyl]guanidine.

EXAMPLE 46

Using, in the procedure of Example 45, the following bromoalkylpyrazoles (which may be prepared by treating the hydroxyalkylpyrazoles with thionyl bromide):
5-methyl-3-bromomethylpyrazole
3,5-dimethyl-4-bromomethylpyrazole
5-hydroxy-3-bromomethylpyrazole
3,4-di(bromomethyl)pyrazole
3-(2-bromomethyl)pyrazole
the products are, respectively:
N-cyano-N'-methyl-N"-[2-((5-methyl-3-pyrazolyl)methylamino)ethyl]guanidine
N-cyano-N'-methyl-N"-[2-((3,5-dimethyl-4-pyrazolyl)methylamino)ethyl[guanidine
N-cyano-N'-methyl-N"-[2-((5-hydroxy-3-pyrazolyl)methylamino)ethyl]guanidine
3,4-bis-[2-(N-cyano-N'-methylguanidino)ethylaminomethyl]pyrazole
N-cyano-N'-methyl-N"-[2-(2-(3-pyrazolyl)ethylamino)ethyl]guanidine.

EXAMPLE 47

2-[(4-Hydroxy-3-pyrazolyl)methylamino]ethylguanidine sulphate

4-Hydroxy-3-hydroxymethylpyrazole (which is prepared by converting 4-hydroxy-3-pyrazolecarboxylic acid to the methyl ester and reducing the ester with lithium aluminium hydride in tetrahydrofuran) is treated with thionyl bromide at room temperature to give 3-bromomethyl-4-hydroxypyrazole.

Using 3-bromomethyl-4-hydroxypyrazole as the starting material in the procedure of Example 43 gives the title compound.

EXAMPLE 48

Reaction of 3-aminopyrazole with β-azidopropionyl chloride by the procedure of Example 40 gives 3-(3-aminopropylamino)pyrazole.

Using 3-(3-aminopropylamino)pyrazole as the intermediate in the procedure of Example 36 gives N-cyano-N'-methyl-N''-[3-(3-pyrazolylamino)propyl]guanidine. Treatment with hydrobromic acid gives the hydrobromide salt.

Also, reacting 3-bromomethylpyrazole with 1,3-diaminopropane by the procedure of Example 34 and using the resulting 3-(3-aminopropylamino)methylpyrazole as the intermediate in the procedure of Example 36 gives N-cyano-N'-methyl-N''-[3-(3-pyrazolylmethylamino)propyl]guanidine.

EXAMPLE 49

Using 3-(3-aminopropylamino)pyrazole as the starting material in the procedure of Example 18 gives N-cyano-N'-[3-(3-pyrazolylamino)propyl]-S-methylisothiourea. Treating this compound with ammoniacal ethanol by the procedure of Example 18 gives N-cyano-N'-[3-(3-pyrazolylamino)propyl]guanidine.

EXAMPLE 50

| Ingredients | Amounts |
| --- | --- |
| N-Cyano-N'-methyl-N''-[2-(3-pyrazolylmethylamino)ethyl]guanidine | 200 mg. |
| Sucrose | 75 mg. |
| Starch | 25 mg. |
| Talc | 5 mg. |
| Stearic acid | 2 mg. |

The ingredients are mixed and filled into a hard gelatin capsule.

Compounds of formula I wherein A is such that there is formed together with the carbon atom shown a six membered unsaturated heterocyclic ring having two nitrogen atoms and four carbon atoms, said unsaturated heterocyclic ring being pyrimidine, pyrazine or pyridazine, and Y is oxygen or sulphur (sulphur is preferred) are exemplified by the following examples.

EXAMPLE 51

2-(2-Pyrimidylmethylthio)ethylguanidine sulphate

A mixture of 5-bromo-2-hydroxymethylpyrimidine (5.6 g.) and magnesium oxide (5.6 g.) in water/ethanol (2:1) was submitted to hydrogenolysis over 10% palladised charcoal for 0.5 hour. Filtration, concentration and ether extraction from an aqueous solution of the residue afforded 2-hydroxymethylpyrimidine (1.85 g.) as a mobile liquid. Reaction of this compound with thionyl chloride gives 2-chloromethylpyrimidine.

By the procedure of Example 1(i)(b), 2-chloromethylpyrimidine is reacted with phthalimidoethanethiol and the product subjected to hydrazinolysis. The resulting 2-[(2-aminoethyl)thiomethyl]pyrimidine is reacted with S-methylisothiouronium sulphate to give the title compound.

EXAMPLE 52

Using 2-[(2-aminoethyl)thiomethyl]pyrimidine as the starting material in the procedure of Example 2 (ii) gives N-nitro-N'-[2-(2-pyrimidylmethylthio)ethyl]guanidine. Similarly, from the same starting material, according to the procedure of Example 2(iii), there is produced N-methyl-N'-nitro-N''-[2-(2-pyrimidylmethylthio)ethyl]guanidine.

EXAMPLE 53

Reacting 2-chloromethylpyrimidine with phthalimidoethanethiol by the procedure of Example 1(i)(b) and then reacting the resulting 2-[(2-aminoethyl)thiomethyl]pyrimidine with dimethyl-N-cyanoimidodithiocarbonate and methylamine by the procedure of Example 3(d) gives N-cyano-N'-methyl-N''-[2-(2-pyrimidylmethylthio)ethyl]guanidine.

Also, reacting 2-hydroxymethylpyrimidine with 3-mercaptopropylamine by the procedure of Example 1 and then reacting the resulting 2-[(3-aminopropyl)thiomethyl]pyrimidine with dimethyl-N-cyanoimidodithiocarbonate and methylamine by the procedure of Example 3(d) gives N-cyano-N'-methyl-N''-[3-(2-pyrimidylmethylthio)propyl]guanidine.

EXAMPLE 54

Using the following chloromethylpyrimidine compounds (prepared where necessary from the corresponding hydroxyethyl compounds and thionyl chloride) in the procedure of Example 53:
4-chloromethyl-6-methylpyrimidine
2-chloromethyl-5-methylpyrimidine
4-hydroxy-2-chloromethylpyrimidine
5-bromo-2-chloromethylpyrimidine
2-chloro-4-chloromethylpyrimidine
2-amino-4-chloromethylpyrimidine
5-chloromethyl-2,4-dimethylpyrimidine
4-chloro-5-chloromethyl-2-methylpyrimidine
the products are, respectively:
N-cyano-N'-methyl-N''-[2-((6-methyl-4-pyrimidyl)methylthio)ethyl]guanidine
N-cyano-N'-methyl-N''-[2-((5-methyl-2-pyrimidyl)methylthio)ethyl]guanidine
N-cyano-N'-[2-((4-hydroxy-2-pyrimidyl)methylthio)ethyl]-N'-methylguanidine
N-[2-((5-bromo-2-pyrimidyl)methylthio)ethyl]-N'-cyano-N''-methylguanidine
N-[2-((2-chloro-4-pyrimidyl)methylthio)ethyl]-N'-cyano-N''-methylguanidine
N-[2-((2-amino-4-pyrimidyl)methylthio)ethyl]-N'-cyano-N''-methylguanidine
N-cyano-N'-[2-((2,4-dimethyl-5-pyrimidyl)methylthio)ethyl]-N''-methylguanidine
N-[2-((4-chloro-2-methyl-5-pyrimidyl)methylthio)ethyl]-N'-cyano-N''-methylguanidine.

EXAMPLE 55

Reaction of 2-[(2-aminoethyl)thiomethyl]pyrimidine with dimethyl-N-cyanoimidodithiocarbonate by the procedure of Example 3(c)(i) gives N-cyano-N'-[2-(2-pyrimidylmethylthio)ethyl]-S-methylisothiourea.

Reaction of the above prepared isothiourea with anhydrous ethylamine by the procedure of Example 4 gives N-cyano-N'-ethyl-N''-[2-(2-pyrimidylmethylthio)ethyl]guanidine.

By the same procedure using propylamine the corresponding N'-propyl guanidine is prepared.

Also, by the same procedure using 2-(dimethylamino)ethylamine, the product is N-cyano-N'-(2-dimethylaminoethyl)-N''-[2-(2-pyrimidylmethylthio)ethyl]guanidine.

EXAMPLE 56

4,6-bis-[2-(N-Cyano-N'-methylguanidino)ethylthiomethyl]pyrimidine 4,6-Pyrimidinecarboxylic acid is converted to the dimethyl ester and the ester is reduced with lithium aluminium hydride in tetrahydrofuran to give 4,6-di(hydroxymethyl)pyrimidine, which on treatment with thionyl chloride gives 4,6-di(chloromethyl)pyrimidine.

Using 4,6-di(chloromethyl)pyrimidine in the procedure of Example 53 gives the title compound.

EXAMPLE 57

N-Cyano-N'-methyl-N''-[2-(2-(2-pyrimidyl)ethyl)thioethyl]guanidine

By the procedure of Example 17 using 2-(2-chloroethyl)pyrimidine, prepared by treating 2-(2-hydroxyethyl)pyrimidine with thionyl chloride, as the starting material, 2-[2-(2-aminoethyl)thioethyl]pyrimidine is prepared, which when treated with N-cyano-N', S-dimethylisothiourea by the procedure of Example 3(a) gives the title compound.

EXAMPLE 58

N-Cyano-N'-methyl-N''-[3-(2-pyrimidylmethoxy)propyl]guanidine

By the procedure of Example 22 using 2-chloromethylpyrimidine, prepared by treating 2-hydroxymethylpyrimidine with thionyl chloride, the title compound is prepared.

EXAMPLE 59

A mixture of 2-mercaptopyrimidine (5.6 g.) and 3-bromopropylphthalimide (13.4 g.) in ethanol (100 ml.) containing sodium (1.15 g.) was heated under reflux for 20 hours to give 2-(3-phthalimidopropylthio)pyrimidine, m.p. 81.5°–82.5° (from ethanol-water). Reaction of the phthalimido compound (3.7 g.) and hydrazine (1.86 g.) followed by reaction of the product directly with N-cyano-N', S-dimethylisothiourea by the procedure of Example 3(a) gives N-cyano-N'-methyl-N''-[3-(2-pyrimidylthio)propyl]guanidine.

By the same procedure, using 4-mercapto-2-trifluoromethylpyrimidine (prepared by reacting 4-hydroxy-2-trifluoromethylpyrimidine with phosphorus pentasulfide), N-cyano-N'-methyl-N''-[3-(2-trifluoromethyl-4-pyrimidylthio)propyl]guanidine is prepared.

EXAMPLE 60

Reaction of 2-(3-aminopropylthio)pyrimidine with dimethyl-N-cyanoimidodithiocarbonate and then with ammonia by the procedure of Example 18 gives N-cyano-N'-[3-(2-pyrimidylthio)propyl]guanidine.

EXAMPLE 61

| Ingredients | Amounts |
|---|---|
| N-Cyano-N'-methyl-N''-[2-(2-pyrimidylmethylthio)ethyl]guanidine | 150 mg. |
| Lactose | 100 mg. |

The ingredients are mixed and filled into a hard gelatin capsule.

EXAMPLE 62

2-(2-Pyrazinylmethylthio)ethylguanidine sulphate

2-Chloromethylpyrazine (6.4 g.) was added over 20 minutes to a solution freshly prepared from sodium (0.23 g.) in ethanol (50 ml.) to which cysteamine hydrochloride (5.7 g.) had been added gradually at 0° and stirred at this temperature for 2 hours. The suspension finally obtained was stirred at room temperature overnight, acidified with hydrochloric acid (pH 5) and concentrated under reduced pressure. The dry residue was extracted with ethanol and the extracts filtered and concentrated to give the crude product. Extraction with isopropyl alcohol, with the removal of some polymeric material and the addition of ether gave a cream coloured solid (3.5 g.), which was recrystallised from ethanol-ether to furnish 2-[(2-aminoethyl)thiomethyl]pyrazine hydrochloride m.p. 144°–146°.

The amine hydrochloride (1.6 g.) was converted into the free base and reacted with S-methylisothiouronium sulphate by the procedure of Example 1 to give the title compound.

EXAMPLE 63

Reaction of 2-[(2-aminoethyl)thiomethyl]pyrazine with S-methyl-N-nitroisothiourea by the procedure of Example 2(ii) gives N-nitro-N'-[2-(2-pyrazinylmethylthio)ethyl]guanidine. Similarly by the procedure of Example 2 (iii), there is prepared N-methyl-N'-nitro-N''-[2-(2-pyrazinylmethylthio)ethyl]guanidine.

EXAMPLE 64

N-Cyano-N'-methyl-N''-[2-(2-pyrazinylmethylthio)ethyl]guanidine

Reaction of 2-[(2-aminoethyl)thiomethyl[pyrazine with dimethyl-N-cyanoimidodithiocarbonate by the procedure of Example 3(c)(i) gives N-cyano-N'-[2-(2-pyrazinylmethylthio)ethyl]-S-methylisothiourea.

Reaction of this isothiourea with methylamine by the procedure of Example 3(c)(ii) gives the title compound.

EXAMPLE 65

Anhydrous ethylamine is reacted with N-cyano-N'-[2-(2-pyrazinylmethylthio)ethyl]-S-methylisothiourea by the procedure of Example 4 to give N-cyano-N'-ethyl-N''-[2-(2-pyrazinylmethylthio)ethyl]guanidine.

By the same procedure, using propylamine the corresponding N'-propyl guanidine is prepared. Using 2-(dimethylamino)ethylamine the corresponding N'-(2-dimethylaminoethyl) guanidine is prepared.

EXAMPLE 66

By the procedure of Example 62, the following chloromethylpyrazines:
2-chloromethyl-5-methylpyrazine
2-chloromethyl-3-methylpyrazine
3-chloro-2-chloromethylpyrazine
3-amino-2-chloromethylpyrazine
2,3-di(chloromethyl)pyrazine
are converted to the corresponding 2-[(2-aminoethyl)thiomethyl]pyrazines and these intermediates are used as starting materials in the procedure of Example 3 to give the following products:
N-cyano-N'-methyl-N''-[2-((5-methyl-2-pyrazinyl)methylthio)ethyl]guanidine.
N-cyano-N'-methyl-N''-[2-((3-methyl-2-pyrazinyl)methylthio)ethyl]guanidine N-cyano-N'-methyl-N''-[2-((3-chloro-2-pyrazinyl)methylthio)ethyl]guanidine
N-cyano-N'-methyl-N''-[2-((3-amino-2-pyrazinyl)methylthio)ethyl]guanidine
2,3-bis-[2-(N-cyano-N'-methylguanidino)ethylthiomethyl]pyrazine.

EXAMPLE 67

3-Hydroxypyrazine-2-carboxylic acid is converted to the methyl ester and the ester is reduced with lithium aluminium hydride in tetrahydrofuran to give 3-hydroxy-2-hydroxymethylpyrazine. Treatment of 3-hydroxy-2-hydroxymethylpyrazine at room temperature with thionyl chloride gives 3-hydroxy-2-chloromethylpyrazine and reacting this intermediate with cysteamine by the procedure of Example 62 gives 2-[(2-aminoethyl)thiomethyl]-3-hydroxypyrazine.

Using 2-[(2-aminoethyl)thiomethyl]-3-hydroxypyrazine as the starting material in the procedure of Example 3(c) gives N-cyano-N'-[2-((3-hydroxy-2-pyrazinyl)methylthio)ethyl[-N''-methylguanidine.

By the same procedure, using 3,6-dimethylpyrazine-2-carboxylic acid as the starting material, the product is N-cyano-N'-[2-((3,6-dimethyl-2-pyrazinyl)methylthio)ethyl]-N''-methylguanidine.

Reduction of 3-chloro-5-methyl-2-pyrazinecarboxylic acid with diborane gives 3-chloro-2-hydroxymethyl-5-methylpyrazine which, using the above procedure, yields N-[2-((3-chloro-5-methyl-2-pyrazinyl)methylthio)ethyl]-N'-cyano-N''-methylguanidine.

By the above procedure, using 3-hydroxy-2-chloromethylpyrazine and, instead of cysteamine, using 3-mercaptopropylamine, the product obtained is N-cyano-N'-[3-((3-hydroxy-2-pyrazinyl)methylthio)-propyl]-N''-methylguanidine.

EXAMPLE 68

N-Cyano-N'-methyl-N''-[2-(2-(2-pyrazinyl)ethyl)thioethyl]guanidine

Using 2-(2-chloroethyl)pyrazine, prepared by reacting 2-(2-hydroxyethyl)pyrazine with thionyl chloride, as the starting material in the procedure of Example 57 gives the title compound.

EXAMPLE 69

N-Cyano-N'-methyl-N''-[3-(2-pyrazinylthio)propyl]guanidine

Using 2-mercaptopyrazine as the starting material in the procedure of Example 59 gives the title compound.

EXAMPLE 70

N-Cyano-N'-methyl-N''-[2-(2-pyrazinylmethoxy)ethyl]guanidine

2-Chloromethylpyrazine is reacted with the sodium salt of ethylene glycol to give 2-(2-hydroxyethoxymethyl)pyrazine which is treated with thionyl chloride to give 2-(2-chloroethoxymethyl)pyrazine. Using this intermediate in place of 4-(3-chloropropoxy)methylimidazole in the procedure of Example 22 gives the title compound.

EXAMPLE 71

Using 2-[(2-aminoethyl)thiomethyl]pyrazine as the starting material in the procedure of Example 18 gives N-cyano-N'-[2-(2-pyrazinylmethylthio)ethyl]guanidine.

EXAMPLE 72

| Ingredients | Amounts |
| --- | --- |
| N-Cyano-N'-methyl-N''-[2-(2-pyrazinylmethylthio)ethyl]guanidine | 200 mg. |
| Lactose | 100 mg. |

The ingredients are mixed and filled into a hard gelatin capsule.

EXAMPLE 73

2-(3-Pyridazinylmethylthio)ethylguandine sulphate

By the procedure of Example 1, using 3-hydroxymethylpyridazine, the intermediate 3-[(2-aminoethyl)thiomethyl]pyridazine dipicrate, m.p. 145°–148° is prepared. Converting this picrate to the dihydrobromide, then to the free base by the procedure of Example 1 and reacting the 3-[(2-aminoethyl)thiomethyl]pyridazine with S-methylisothiouronium sulphate by the procedure of Example 1 gives the title compound.

EXAMPLE 74

Reaction of 3-[(2-aminoethyl)thiomethyl]pyridazine with S-methyl-N-nitroisothiourea by the procedure of Example 2(ii) gives N-nitro-N'-[2-(3-pyridazinylmethylthio)ethyl]guanidine. Similarly, by the procedure of Example 2(iii), there is obtained N-methyl-N'-nitro-N''-[2-(3-pyridazinylmethylthio)ethyl]guanidine.

EXAMPLE 75

Reacting 3-hydroxymethylpyridazine with cysteamine by the procedure of Example 1 and then reacting the resulting 3-[(2-aminoethyl)thiomethyl]pyridazine with dimethyl-N-cyanoimidodithiocarbonate by the procedure of Example 3(c)(i) gives N-cyano-N'-[2-(3-pyridazinylmethylthio)ethyl]-S-methylisothiourea.

Reacting this isothiourea with methylamine by the procedure of Example 3(c)(ii) gives N-cyano-N'-methyl-N''-[2-(3-pyridazinylmethylthio)ethyl]guanidine.

Treating this procedure with hydrobromic acid gives the hydrobromide salt.

Hydrolysis of N-cyano-N'-methyl-N''-[2-(3-pyridazinylmethylthio)ethyl]guanidine by the procedure of Example 3(e) gives N-methyl-N'-[2-(3-pyridazinylmethylthio)ethyl]guanidine.

EXAMPLE 76

Anhydrous ethylamine is reacted with N-cyano-N'-[2-(3-pyridazinylmethylthio)ethyl]-S-methylisothiourea by the procedure of Example 4 to give N-cyano-N'-ethyl-N''-[2-(3-pyridazinylmethylthio)ethyl]guanidine.

Using 2-(dimethylamino)ethylamine, the product is N-cyano-N'-(2-dimethylaminoethyl)-N''-[2-(3-pyridazinylmethylthio)ethyl]guanidine.

EXAMPLE 77

Using in the procedure of Example 75 the following hydroxymethylpyridazines:
4-hydroxymethyl-6-methylpyridazine
4-hydroxymethyl-3,6-dimethylpyridazine
3-chloro-4-hydroxymethyl-6-methylpyridazine
4,5-di(hydroxymethyl)pyridazine
the products are, respectively:
N-cyano-N'-methyl-N''-[2-((6-methyl-4-pyridazinyl)methylthio)ethyl]guanidine N-cyano-N'-[2-((3,6-dimethyl-4-pyridazinyl)methylthio)ethyl]-N''-methylguanidine N-[2-((3-chloro-6-methyl-4-pyridazinyl)methylthio)ethyl]-N'-cyano-N''-methylguanidine 4,5-bis-[2-(N-cyano-N'-methylguanidino)ethylthiomethyl]pyridazine.

Using in the procedure of Example 75, 3-mercaptopropylamine in place of cysteamine, the product is N-cyano-N'-methyl-N''-[3-(3-pyridazinylmethylthio)propyl]guanidine.

EXAMPLE 78

6-Amino-3-pyridazinecarboxylic acid is converted to the ethyl ester and the ester is reduced with lithium aluminium hydride in tetrahydrofuran to give 6-amino-3-hydroxymethylpyridazine.

Using 6-amino-3-hydroxymethylpyridazine as the starting material in the procedure of Example 75 gives N-[2-((6-amino-3-pyridazinyl)methylthio)ethyl]-N'-cyano-N''-methylguanidine.

By the same procedure, using 6-hydroxy-3-pyridazinecarboxylic acid as the starting material, N-cyano-N'-[2-((6-hydroxy-3-pyridazinyl)methylthio)ethyl]-N''-methylguanidine is prepared.

Reduction of 6-chloro-3-pyridazinecarboxylic acid with diborane gives 6-chloro-3-hydroxymethylpyridazine which, in the procedure of Example 75, gives N-[2-((6-chloro-3-pyridazinyl)methylthio)ethyl]-N'-cyano-N''-methylguanidine.

EXAMPLE 79

N-Cyano-N'-methyl-N''-[2-(2-(3-pyridazinyl)ethyl)thioethyl]guanidine

3-Cyanomethylpyridazine is treated with aqueous sodium hydroxide to give 3-pyridazineacetic acid.

3-Pyridazineacetic acid is esterified with anhydrous ethanolic hydrogen chloride and the resulting ethyl ester is reduced with lithium aluminium hydride in tetrahydrofuran to give 3-(2-hydroxyethyl)pyridazine. Treating this hydroxyethyl compound with thionyl chloride gives 3-(2-chloroethyl)pyridazine.

Using 3-(2-chloroethyl)pyridazine as the starting material in the procedure of Example 17 gives the title compound.

EXAMPLE 80

N-Cyano-N'-methyl-N''-[3-(3-pyridazinylthio)propyl]guanidine

Using 3-mercaptopyridazine as the starting material in the procedure of Example 20 gives the title compound.

EXAMPLE 81

N-Cyano-N'-methyl-N''-[3-(3-pyridazinylmethoxy)propyl]guanidine

Using 3-chloromethylpyridazine, prepared by reacting 3-hydroxymethylpyridazine with thionyl chloride, as the starting material in the procedure of Example 22 gives the title compound.

EXAMPLE 82

Using 3-[(2-aminoethyl)thiomethyl]pyridazine as the starting material in the procedure of Example 18 gives N-cyano-N'-[2-(3-pyridazinylmethylthio)ethyl]guanidine.

EXAMPLE 83

| Ingredients | Amounts |
| --- | --- |
| N-Cyano-N'-methyl-N''-[2-(3-pyridazinylmethylthio)ethyl]guanidine | 200 mg. |
| Lactose | 100 mg. |

The ingredients are mixed and filled into a hard gelatin capsule.

Compounds of formula I wherein A is such that there is formed together with the carbon atom shown a six membered unsaturated heterocyclic ring having two nitrogen atoms and four carbon atoms, said unsaturated heterocyclic ring being pyrimidine, pyrazine or pyridazine, and Y is NH are exemplified by the following examples.

EXAMPLE 84

2-(2-Pyrimidylmethylamino)ethylguanidine sulphate

By the procedure of Example 34, ethylenediamine is reacted with 2-chloromethylpyrimidine, prepared by treating 2-hydroxymethylpyrimidine with thionyl chloride, to give N-(2-pyrimidylmethyl)ethylenediamine.

The above prepared compound is heated under reflux with S-methylisothiouronium sulphate in water for 3 hours by the procedure of Example 1 to give 2-(2-pyrimidylmethylamino)ethylguanidine sulphate.

EXAMPLE 85

Reaction of N-(2-pyrimidylmethyl)ethylenediamine with S-methyl-N-nitroisothiourea by the procedure of Example 2(ii) gives N-nitro-N'-[2-(2-pyrimidylmethylamino)ethyl]guanidine. Similarly, from the same starting material, according to the procedure of Example 2(iii), there is produced N-methyl-N'-nitro-N''-[2-(2-pyrimidylmethylamino)ethyl]guanidine.

EXAMPLE 86

N-Cyano-N'-methyl-N''-[2-(2-pyrimidylmethylamino)ethyl]guanidine

Reaction of 2-chloromethylpyrimidine with ethylenediamine by the procedure of Example 34 and reaction of the resulting N-(2-pyrimidylmethyl)ethylenediamine with methyl isothiocyanate by the procedure of Example 3(b) gives, after concentrating and chromatographing, N-methyl-N'-[2-(2-pyrimidylmethylamino)ethyl]thiourea. This thiourea is reacted with lead cyanamide by the procedure of Example 3(b) to give the title compound.

EXAMPLE 87

Using ethyl isothiocyanate in place of methyl isothiocyanate in the procedure of Example 86 gives N-cyano-N'-ethyl-N''-[2-(2-pyrimidylmethylamino)ethyl]guanidine.

By the same procedure, using propyl isothiocyanate, the product is N-cyano-N'-propyl-N''-[2-(2-pyrimidylmethylamino)ethyl]guanidine.

Also, using 2-dimethylaminoethyl isothiocyanate, the product is N-cyano-N'-(2-dimethylaminoethyl)-N''-[2-(2-pyrimidylmethylamino)ethyl]guanidine.

EXAMPLE 88

Using, in the procedure of Example 86, the following haloalkylpyrimidines (which may be prepared by treating the corresponding hydroxyalkylpyrimidines with a thionyl halide):
5-bromomethylpyrimidine
2-chloromethyl-5-methylpyrimidine
5-bromo-2-bromomethylpyrimidine
2-bromomethyl-4-hydroxypyrimidine
4-amino-5-bromomethylpyrimidine
5-bromomethyl-2,4-dimethylpyrimidine
4-chloro-5-chloromethyl-2-methylpyrimidine
4-(2-bromoethyl)pyrimidine
4,6-di(bromomethyl)pyrimidine
the products are, respectively:
N-cyano-N'-methyl-N''-[2-(5-pyrimidylmethylamino)ethyl]guanidine
N-cyano-N'-methyl-N''-[2-((5-methyl-2-pyrimidyl)methylamino)ethyl]guanidine
N-[2-((5-bromo-2-pyrimidyl)methylamino)ethyl]-N'-cyano-N''-methylguanidine
N-cyano-N'-[2-((4-hydroxy-2-pyrimidyl)methylamino)ethyl]-N''-methylguanidine
N-[2-((4-amino-5-pyrimidyl)methylamino)ethyl]-N'-cyano-N''-methylguanidine
N-cyano-N'-methyl-N''-[2-((2,4-dimethyl-5-pyrimidyl)methylamino)ethyl]guanidine
N-[2-((4-chloro-2-methyl-5-pyrimidyl)methylamino)ethyl]-N'-cyano-N''-methylguanidine
N-cyano-N'-methyl-N''-[2-(2-(2-pyrimidyl)ethylamino)ethyl]guanidine
4,6-bis-[2-(N-cyano-N'-methylguanidino)ethylaminomethyl]pyrimidine.

Using, in the procedure of Example 86, 1,3-diaminopropane in place of ethylenediamine, the product is N-cyano-N'-methyl-N''-[3-(2-pyrimidylmethylamino)propyl]guanidine.

EXAMPLE 89

Reaction of 2-bromopyrimidine with 1,3-diaminopropane in ethanol containing sodium ethoxide gives 2-(3-aminopropylamino)pyrimidine.

Using 2-(3-aminopropylamino)pyrimidine as the starting material in the procedure of Example 3(a) gives N-cyano-N'-methyl-N''-[3-(2-pyrimidylamino)propyl]guanidine.

By the same procedure, using 4-chloro-2-trifluoromethylpyrimidine (prepared by treating 4-hydroxy-2-trifluoromethylpyrimidine with phosphorus oxychloride and dimethylaniline), the product is N-cyano-N'-methyl-N''-[3-(2-trifluoromethyl-4-pyrimidylamino)propyl]guanidine.

EXAMPLE 90

Using 2-(3-aminopropylamino)pyrimidine as the starting material in the procedure of Example 18 gives N-cyano-N'-[3-(2-pyrimidylamino)propyl]guanidine.

EXAMPLE 91

| Ingredients | Amount |
| --- | --- |
| N-Cyano-N'-methyl-N''-[2-(2-pyrimidylmethylamino)ethyl]guanidine | 200 mg. |
| Lactose | 100 mg. |

The ingredients are mixed and filled into a hard gelatin capsule.

EXAMPLE 92

Ethylenediamine is reacted with 2-chloromethylpyrazine by the procedure of Example 34 to give N-(2-pyrazinylmethyl)ethylenediamine. Heating this compound with S-methylisothiourea in water under reflux for 3 hours by the procedure of Example 1 gives 2-(2-pyrazinylmethylamino)ethylguanidine.

EXAMPLE 93

Reacting N-(2-pyrazinylmethyl)ethylenediamine with S-methyl-N-nitroisothiourea by the procedure of Example 2(ii) gives N-nitro-N'-[2-(2-pyrazinylmethylamino)ethyl]guanidine. Similarly, from the same starting material, according to the procedure of Example 2(iii), there is produced N-methyl-N'-nitro-N''-[2-(2-pyrazinylmethylamino)ethyl]guanidine.

EXAMPLE 94

N-Cyano-N'-methyl-N''-[2-(2-pyrazinylmethylamino)ethyl]guanidine

Reacting 2-chloromethylpyrazine with ethylenediamine by the procedure of Example 34 and reacting the resulting N-(2-pyrazinylmethyl)ethylenediamine with N-cyano-N',S-dimethylisothiourea by the procedure of Example 3 gives the title compound.

EXAMPLE 95

Reacting N-(2-pyrazinylmethyl)ethylenediamine with ethyl isothiocyanate by the procedure of Example 3 and chromatographing gives N-ethyl-N'-[2-(2-pyrazinylmethylamino)ethyl]thiourea. Reacting this thiourea with lead cyanamide by the procedure of Example 3 gives N-cyano-N'-ethyl-N''-[2-(2-pyrazinylmethylamino)ethyl]guanidine.

By the same procedure, using 2-dimethylaminoethyl isothiocyanate, the product is N-cyano-N'-(2-dimethylaminoethyl)-N''-[2-(2-pyrazinylmethylamino)ethyl]guanidine.

EXAMPLE 96

2-[(5-Methyl-2-pyrazinyl)methylamino]ethylguanidine

Using 2-chloromethyl-5-methylpyrazine as the starting material in the procedure of Example 34 gives the title compound.

EXAMPLE 97

Using in the procedure of Example 94, the following haloalkylpyrazines (which may be prepared by treating the corresponding hydroxyalkylpyrazines with a thionyl halide):
2-chloromethyl-3-methylpyrazine
3-chloro-2-chloromethylpyrazine
3-amino-2-chloromethylpyrazine
2,3-di(chloromethyl)pyrazine
2-chloromethyl-3-hydroxypyrazine
2-chloromethyl-3,6-dimethylpyrazine
3-chloro-2-chloromethyl-5-methylpyrazine
2-(2-chloroethyl)pyrazine
the products are, respectively:
N-cyano-N'-methyl-N''-[2-((3-methyl-2-pyrazinyl)methylamino)ethyl]guanidine
N-[2-((3-chloro-2-pyrazinyl)methylamino)ethyl]N'-cyano-N''-methylguanidine
N-[2-((3-amino-2-pyrazinyl)methylamino)ethyl]-N''-cyano-N''-methylguanidine
2,3-bis-[2-(N-cyano-N'-methylguanidino)ethylaminomethyl]pyrazine
N-cyano-N'-[2-((3-hydroxy-2-pyrazinyl)methylamino)ethyl]-N''-methylguanidine N-cyano-N'-methyl-N''-[2-((3,6-dimethyl-2-pyrazinyl)-methylamino)ethyl]guanidine N-[2-((3-chloro-5-methyl-2-pyrazinyl)methylamino)ethyl]-N'-cyano-N''-methylguanidine N-cyano-N'-methyl-N''-[2-(2-(2-pyrazinyl)ethylamino)ethyl]guanidine.

Using in the procedure of Example 94, 1,3-diaminopropane in place of ethylenediamine gives, as the product, N-cyano-N'-methyl-N''-[3-(2-pyrazinylmethylamino) propyl]guanidine.

EXAMPLE 98

N-Cyano-N'-methyl-N''-[3-(2-pyrazinylamino)propyl]-guanidine

Reacting 2-chloropyrazine with 1,3-diaminopropane in ethanol containing sodium ethoxide by the procedure of Example 89 gives 2-(3-aminopropylamino)pyrazine.

Using 2-(3-aminopropylamino)pyrazine as the starting material in the procedure of Example 3(a) gives the title compound.

EXAMPLE 99

Using 2-(3-aminopropylamino)pyrazine as the starting material in the procedure of Example 18 gives N-cyano-N'-[3-(2-pyrazinylamino)propyl]guanidine.

EXAMPLE 100

| Ingredients | Amounts |
| --- | --- |
| N-Cyano-N'-methyl-N''-[2-(2-pyrazinyl-methylamino)ethyl]guanidine | 200 mg. |
| Sucrose | 75 mg. |
| Starch | 25 mg. |
| Talc | 5 mg. |
| Stearic acid | 2 mg. |

The ingredients are mixed and filled into a hard gelatin capsule.

EXAMPLE 101

2-(3-Pyridazinylmethylamino)ethylguanidine sulphate

Reacting ethylenediamine with 3-chloromethylpyridazine by the procedure of Example 34 gives N-(3-pyridazinylmethyl)ethylenediamine. This intermediate is reacted with S-methylisothiouronium sulphate by the procedure of Example 1 to give the title compound.

EXAMPLE 102

Reacting N-(3-pyridazinylmethyl)ethylenediamine with S-methyl-N-nitroisothiourea by the procedure of Example 2(ii) gives N-nitro-N'-[2-(3-pyridazinylmethylamino)ethyl]quanidine. Treatment with hydrobromic acid gives the hydrobromide salt.

Similarly, by the procedure of Example 2(iii), there is produced N-methyl-N'-nitro-N''-[2-(3-pyridazinylmethylamino)ethyl]guanidine.

EXAMPLE 103

Reacting 3-chloromethylpyridazine with ethylenediamine by the procedure of Example 34 and reacting the resulting N-(3-pyridazinylmethyl)ethylenediamine with methyl isothiocyanate by the procedure of Example 3(b), then chromatographing gives N-methyl-N'-[2-(3-pyridazinylmethylamino)ethyl]thiourea. This intermediate is reacted with lead cyanamide by the procedure of Example 3(b) to give N-cyano-N'-methyl-N''-[2-(3-pyridazinylmethylamino)ethyl]guanidine. Hydrolysis of this compound by the procedure of Example 3(e) gives N-methyl-N'-[2-(3-pyridazinylmethylamino)ethyl]guanidine dihydrochloride.

EXAMPLE 104

Using ethyl isothiocyanate in place of methyl isothiocyanate in the procedure of Example 103 gives N-cyano-N'-ethyl-N''-[2-(3-pyridazinylmethylamino)ethyl]guanidine.

Using 2-dimethylaminoethyl isothiocyanate in the above procedure gives N-cyano-N'-(2-dimethylaminoethyl)-N''-[2-(3-pyridazinylmethylamino)ethyl]guanidine.

EXAMPLE 105

Using, in the procedure of Example 103, the following chloroalkylpyridazines (which may be prepared by treating the hydroxyalkylpyridazines with thionyl chloride):

4-chloromethyl-6-methylpyridazine
4-chloromethyl-3,6-dimethylpyridazine
3-chloro-4-chloromethyl-6-methylpyridazine
4,6-di(chloromethyl)pyridazine
6-amino-3-chloromethylpyridazine
6-chloro-3-chloromethylpyridazine
3-chloromethyl-6-hydroxypyridazine
3-(2-chloroethyl)pyridazine the products are, respectively:

N-cyano-N'-methyl-N''-[2-((6-methyl-4-pyridazinyl)methylamino)ethyl]guanidine.

N-cyano-N'-methyl-N''-[2-((3,6-dimethyl-4-pyridazinyl)methylamino)ethyl]guanidine N-[2-((3-chloro-6-methyl-4-pyridazinyl)methylamino)ethyl]-N'-cyano-N''-methylguanidine 4,6-bis-[2-(N-cyano-N'-methylguanidino)ethylaminomethyl]pyridazine N-[2-((6-amino-3-pyridazinyl)methylamino)ethyl]-N'-cyano-N''-methylguanidine N-[2-((6-chloro-3-pyridazinyl)methylamino)ethyl]-N'-cyano-N''-methylguanidine N-cyano-N'-[2-((6-hydroxy-3-pyridazinyl)methylamino)ethyl]-N''-methylguanidine N-cyano-N'-methyl-[2-(2-(3-pyridazinyl)ethyl)aminoethyl]guanidine.

Using 1,3-diaminopropane in place of ethylenediamine in the procedure of Example 103 gives N-cyano-N'-methyl-N''-[3-(3-pyridazinylmethylamino)propyl]guanidine.

EXAMPLE 106

Reacting 3-chloropyridazine with 1,3-diaminopropane in ethanol containing sodium ethoxide according to the procedure of Example 89 gives 3-(3-aminopropylamino)pyridazine. Using this intermediate as the starting material in the procedure of Example 18 gives N-cyano-N'-[3-(3-pyridazinylamino)propyl]guanidine.

EXAMPLE 107

| Ingredients | Amounts |
| --- | --- |
| N-Cyano-N'-methyl-N''-[2-(3-pyridazinylmethylamino)ethyl]guanidine | 150 mg. |
| Lactose | 100 mg. |

The ingredients are mixed and filled into a hard gelatin capsule.

Compounds of formula I where A is such that there is formed together with the carbon atom shown a five membered unsaturated heterocyclic ring having one nitrogen atom, one sulphur or oxygen atom and three carbon atoms, said unsaturated heterocyclic ring being thiazole, isothiazole, oxazole or isoxazole, and Y is oxygen or sulphur (sulphur is preferred) are exemplified by the following examples.

EXAMPLE 108

By the procedure of Example 1, using as the starting materials 2-hydroxymethylthiazole and 4-hydroxymethylthiazole, were produced the following intermediate amine salts:

2-](2-aminoethyl)thiomethyl]thiazole dihydrobromide, m.p. 144°–147.5° C. 4-[(2-aminoethyl)thiomethyl]-thiazole dihydrobromide, m.p. 197°–203° C.

These amine salts were converted to the free bases and reacted with S-methylisothiouronium sulphate by the procedure of Example 1 to give the following products:

2-(2-thiazolylmethylthio)ethylguanidine sulphate
2-(4-thiazolylmethylthio)ethylguanidine sulphate.

EXAMPLE 109

Reaction of 2-[(2-aminoethyl)thiomethyl]thiazole with S-methyl-N-nitroisothiourea by the procedure of Example 2(ii) gives N-nitro-N'-[2-(2-thiazolylmethylthio)ethyl]guanidine.

Also, reaction of the same starting material with N,S-dimethyl-N'-nitroisothiourea by the procedure of Example 2(iii) gives N-methyl-N'-nitro-N''-[2-(2-thiazolylmethylthio)ethyl]guanidine.

EXAMPLE 110

N-Cyano-N'-methyl-N''-[2-(2-thiazolylmethylthio)ethyl]guanidine (a) Reaction of [(2-aminoethyl)thiomethyl]thiazole (from the dihydrobromide 20.2 g.) with N-cyano-N',S-dimethylisothiourea (7.75 g.) by a procedure similar to that described in Example 3(a) afforded N-cyano-N'-methyl-N''-[2-(2-thiazolylmethylthio)ethyl]guanidine, m.p. 120°–122.5°, following chromatography on silica gel with acetonitrile as eluant, and recrystallisation from isopropyl alcohol. (Found: C, 42.3; H, 5.1; N, 27.2; S, 25.3. $C_9H_{13}N_5S_2$ requires: C, 42.3; H, 5.1; N, 27.4; N, 27.4; S, 25.1).

(b) The sequential reaction of dimethyl-N-cyanoimidodithiocarbonate (5.5 g.) with 2-[(2-aminoethyl)thiomethyl]thiazole (from the dihydrobromide) (12.0 g.) and excess methylamine by the procedure described in Example 3(d) afforded N-cyano-N'-methyl-N''-[2-(2-thiazolylmethylthio) ethyl]guanidine (8.46 g.), m.p. 121°–123° (from isopropyl alcohol).

Hydrolysis of N-cyano-N'-methyl-N''-[2-(2-thiazolylmethylthio)ethyl]guanidine by the procedure of Example 3(e) gives N-methyl-N'-[2-(2-thiazolylmethylthio)ethyl]guanidine dihydrochloride.

EXAMPLE 111

Reaction of N-cyano-N'-[2-(2-thiazolylmethylthio)ethyl]-S-methylisothiourea, prepared from 2-[(2-aminoethyl)thiomethyl]thiazole by the procedure of Example 3(c)(i), with ethylamine by the procedure of Example 4 gives N-cyano-N'-ethyl-N''-[2-(2-thiazolylmethylthio)ethyl]guanidine.

Similarly, using propylamine and 2-(dimethylamino)ethylamine, the products are respectively:

N-cyano-N'-propyl-N''-[2-(2-thiazolylmethylthio)ethyl]guanidine
N-cyano-N'-(2-dimethylaminoethyl)-N'-[2-(2-thiazolylmethylthio)ethyl]guanidine.

EXAMPLE 112

N-Cyano-N'-methyl-N''-[3-(2-thiazolylthio)propyl]-guanidine

By the procedure of Example 20, using 2-mercaptothiazole as the starting material, the intermediate amine salt, 2-(3-aminopropylthio)thiazole dihydrobromide, m.p. 175°–178° C., was prepared.

The above prepared amine salt is converted to the free base and reacted with N-cyano-N,S-dimethylisothiourea by the procedure of Example 3(a) to give the title compound.

EXAMPLE 113

N-Cyano-N'-methyl-N''-[2-(5-thiazolylmethylthio)ethyl]guanidine (i) The reaction of 5-hydroxymethylthiazole (2.01 g.) with cysteamine hydrochloride (1.99 g.) in aqueous hydrobromic acid by the method described in Example 1(i)(a) gave 5-((2-aminoethyl)thiomethyl)thiazole dihydrobromide (4.85 g.) m.p. 191°–4° (from methanol).

(ii) The reaction of 5-((2-aminoethyl)thiomethyl)-thiazole (2.24 g.) with methyl isothiocyanate (0.94 g.) in ethanol (10 ml.) gave a thiourea which was purified by chromatography on a column of silica gel with ethyl acetate as eluant. Recrystallisation from isopropyl acetate-methyl ethyl ketone-ether gave N-methyl-N'-[2-(5-thiazolylmethylthio)ethyl]thiourea (2.1 g.) m.p. 86°–88°.

(iii) The reaction of N-methyl-N'-[2-(5-thiazolylmethylthio)ethyl]thiourea with lead cyanamide by the procedure of Example 3(b) gives the title compound.

EXAMPLE 114

N-Cyano-N'-methyl-N''-[2-((2-amino-4-thiazolyl)methylthio)ethyl]guanidine (i) A mixture of 2-amino-4-chloromethylthiazole hydrochloride (9.0 g.) and cysteamine hydrochloride (5.53 g.) in acetic acid (100 ml.) was heated under reflux for 18 hours. The crude product obtained after concentration was treated with picric acid in ethanol to afford 2-amino-4-[(2-aminoethyl)thiomethyl]thiazole dipicrate, m.p. aproximately 200°–210° (from ethanol).

(ii) The picrate was converted into the free base by addition of hydrochloric acid, removal of picric acid by toluene extraction, basification with potassium carbonate and extraction of the aqueous residue with ethanol-ether. Reaction of the base (1.89 g.) with methyl isothiocyanate (0.73 g.) in ethanol (10 ml.) in the usual way gave the crude thiourea. Chromatography on a column of silica gel with ethyl acetate as eluant, followed by recrystallisation from isopropyl alcoholisopropyl acetate gave N-methyl-N'-[2-((2-amino-4-thiazolyl)methylthio)ethyl]thiourea (1.0 g.), m.p. 136°–140°.

(iii) Reaction of N-methyl-N'-[2-((2-amino-4-thiazolyl)methylthio)ethyl]thiourea with lead cyanamide by the procedure of Example 3(b) gives the title compound.

EXAMPLE 115

The following hydroxymethyl and halomethyl thiazoles are converted to the corresponding (2-aminoethyl)thiomethylthiazoles by the procedure of Example 1:

2-hydroxymethyl-4-methylthiazole
4-chloromethyl-2-methylthiazole
2-chloro-4-chloromethylthiazole
2-bromomethyl-4,5-dimethylthiazole
4-ethyl-2-hydroxymethyl-5-methylthiazole and using the (2-aminoethyl)thiomethylthiazoles as starting materials in the procedure of Example 3 gives the following products, respectively:

N-cyano-N'-methyl-N''-[2-((4-methyl-2-thiazolyl)methylthio)ethyl]guanidine
N-cyano-N'-methyl-N''-[2-((2-methyl-4-thiazolyl)methylthio)ethyl]guanidine
N-[2-((2-chloro-4-thiazolyl)methylthio)ethyl]-N'-cyano-N''-methylguanidine
N-cyano-N'-methyl-N''-[2-((4,5-dimethyl-2-thiazolyl)methylthio)ethylguanidine
N-cyano-N'-[2-((4-ethyl-5-methyl-2-thiazolyl)methylthio)ethyl]-N''-methylguanidine.

Reacting 2-hydroxymethylthiazole with 3-mercaptopropylamine by the procedure of Example 1 and using the resulting 2-[(3-aminopropyl)thiomethyl]thiazole as the starting material in the procedure of Example 3(a) gives N-cyano-N'-methyl-N''-[3-(2-thiazolymethylthio)propyl]guanidine.

EXAMPLE 116

2-Benzyl-4-thiazolecarboxylic acid is converted to the methyl ester and the ester is reduced with lithium aluminum hydride in tetrahydrofuran to give 2-benzyl-4-hydroxymethylthiazole. By the procedure of Example 1 this compound is converted to 4-[(2-aminoethyl)thiomethyl]-2-benzylthiazole. Using this compound as the starting material in the procedure of Example 110 gives N -[2-((2-benzyl-4-thiazolyl)methylthio)ethyl]-N'-cyano-N''-methylguanidine.

By the same procedure, from the following compounds:

2,4-thiazoledicarboxylic acid
2-hydroxy-4-thiazolecarboxylic acid the following products are obtained, respectively:

2,4-bis-[2-(N-cyano-N'-methylguanidino)ethylthiomethyl]thiazole
N-cyano-N'-[2-((2-hydroxy-4-thiazolyl)methylthio)ethyl]-N''-methylguanidine.

Reduction of 5-bromo-4-methyl-2-thiazolecarboxylic acid with diborane yields 5-bromo-4-methyl-2-hydroxymethylthiazole which by the above procedures may be converted to N-[2-(5-bromo-4-methyl-2-thiazolyl)methylthio)ethyl]-N'-cyano-N''-methylguanidine.

EXAMPLE 117

N-Cyano-N'-methyl-N''-[3-(4-thiazolylmethoxy)propyl]guanidine

Using 4-chloromethylthiazole, prepared by reacting 4-hydroxymethylthiazole with thionyl chloride, as the starting material in the procedure of Example 22 gives the title compound.

EXAMPLE 118

N-Cyano-N'-methyl-N''-[2-(2-(4-thiazolyl)ethyl)thioethyl)guanidine

Using 4-(2-chloroethyl)thiazole as the starting material in the procedure of Example 17 gives the title compound.

EXAMPLE 119

Using 2-[(2-aminoethyl)thiomethyl]thiazole as the starting material in the procedure of Example 18 gives N-cyano-N''-[2-(2-thiazolylmethylthio)ethyl]guanidine.

Treatment of the product with maleic acid in ethanol gives the maleate salt.

EXAMPLE 120

| Ingredients | Amounts |
| --- | --- |
| N-Cyano-N'-methyl-N''-[2-(2-thiazolylmethylthio)ethyl]guanidine | 150 mg. |
| Sucrose | 75 mg. |
| Starch | 25 mg. |
| Talc | 5 mg. |
| Stearic acid | 2 mg. |

The ingredients are mixed and filled into a hard gelatin capsule.

EXAMPLE 121

N-Cyano-N'-[2-(3-isothiazolylmethylthio)ethyl]-N''-methylguanidine (a) (i) A solution was prepared by the gradual addition of cysteamine hydrochloride (2.03 g.) to sodium (0.83 g.) dissolved in ethanol (50 ml.) with stirring at 0° under a nitrogen atmosphere. After stirring for 2 hours at 0°, 3-bromomethylisothiazole (3.2 g.) was added dropwise over 15 minutes at 0°, the reaction mixture subsequently being set aside overnight at room temperature. Following acidifcation to pH 3.5 with hydrochloric acid, concentration and re-evaporation with ethanol, the residue was dissolved in ethanol, filtered and concentrated to yield 3-[(2-aminoethyl)thiomethyl]isothiazole hydrochloride (3.5 g.). This was converted directly to the free base by treatment with aqueous potassium carbonate and extraction with ether. The extracts were dried over magnesium sulphate, filtered and concentrated to yield the amine base as an oil (1.56 g.). The amine was dissolved in ethanol (10 ml.), methyl isothiocyanate (0.66 g.) added, and the solution heated under reflux for 30 minutes, Concentration, followed by purification of the crude product by chromatography on a column of silica gel with ethyl acetate as eluant followed by chromatography on a column of alumina with benzene/ethyl acetate as eluant gave N-methyl-N'-[2-(3-isothiazolylmethylthio)ethyl]thiourea. (Found: C, 38.9; H, 5.4; N, 16.5; S, 38.3. $C_8H_{13}N_3S_3$ requires: C, 38.8: H, 5.3; N, 17.0; S, 38.9.

(ii) Lead cyanamide (52.6 g.) was added to a solution of N-methyl-N'-[2-(3-isothiazolymlethylthio)ethyl]thiourea (17.7 g.) in acetonitrile (500 ml.) containing dimethylformamide (50 ml.). The mixture was stirred under reflux for 48 hours, then filtered and concentrated. The product was chromatographed on silica gel with ethyl acetate as eluant and recrystallised from isopropyl acetate-ether to give N-cyano-N'-[2-(3-isothiazolylmethylthio)ethyl]-N''-methylguanidine, in a crystalline form, m.p. 63°-64°. Further recrystallisation from isopropyl acetate afforded the cyanoguanidine in a crystalline form, m.p. 91°-92°. (Found: C, 42.6; H, 5.2; N, 27.4; S, 25.4. $C_9H_{13}N_5S_2$ requires: C, 42.3; H, 5.1; N, 27.4; S, 25.1).

(b) (i) The reaction of dimethyl-N-cyanoimidodithiocarbonate (1.50 g.) with 3-[(2-aminoethyl)thiomethyl]isothiazole (1.70 g.) by the procedure described in Example 3(c) afforded N-cyano-N'-[2-(3-isothiazolylmethylthio)ethyl]-S-methylisothiourea. Recrystallisation from isopropyl acetate afforded 0.68 g., m.p. 85°–87°. (Found: C, 39.7; H, 4.4; N, 20.6; S, 35.4. $C_9H_{12}N_4S_3$ requires: C, 39.7; H, 4.4; N, 20.6; S, 35.3).

(ii) The reaction of N-cyano-N'-[2-(3-isothiazolylmethylthio)ethyl]-S-methylisothiourea (0.27 g.) with excess methylamine according to the procedure described in Example 3(c) and recrystallisation of the product from isopropyl acetate afforded N-cyano-N'-[2-(3-isothiazolylmethylthio)ethyl]-N''-methylguanidine (0.12 g.), m.p. 91°–93°. (Found: C, 42.4; H, 5.1; N, 27.3; S, 25.2. $C_9H_{13}N_5S_2$ requires: C, 42.3; H, 5.1; N, 27.4; S, 25.1).

EXAMPLE 122

The reaction of 4-bromo-3-(bromomethyl)isothiazole (8.5 g.) with cysteamine (from cyteamine hydrochloride, 3.76 g.) was performed under conditions similar to those described in Example 121. From the reaction there was obtained 4-bromo-3-[(2-aminoethyl)thiomethyl]isothiazole hydrobromide, which, following recrystallisation from ethanol-ether and acetonitrile, gave needles (4.05 g.) m.p. 111°–112°. The amine base (2.73 g.) was isolated by basification with sodium hydroxide and extraction with chloroform and then dissolved in ethanol and treated with methyl isothiocyanate (0.78 g.). The solution was heated under reflux for 30 minutes, concentrated and the residue triturated with ether to yield the crystalline thiourea (2.9 g.) m.p. 60°–61°. Recrystallisation from isopropyl acetate gave N-methyl-N'-[2-((4-bromo-3-isothiazolyl)methylthio)ethyl]thiourea (2.3 g.) as needles, m.p. 62°–63°.

Reaction of N-methyl-N'-[2-((4-bromo-3-isothiazolyl)methylthio)ethyl]thiourea with lead cyanamide by the procedure of Example 121 gives N-cyano-N'-[2-((4-bromo-3-isothiazolyl)methylthio)ethyl]-N''-methylguanidine.

Hydrolysis of the above product according to the procedure of Example 3(e) gives N-[2-((4-bromo-3-isothiazolyl)methylthio)ethyl]-N'-methylguanidine hydrochloride.

EXAMPLE 123

Reacting 4-hydroxymethyl-3-methylisothiazole (3.0 g.) with cysteamine hydrochloride (2.8 g.) in 48% aqueous hydrobromic acid (50 ml.) by the procedure of Example 1 gives 3-methyl-4-[-(2-aminoethyl)thiomethyl]isothiazole hydrobromide. Treatment of this intermediate with aqueous potassium carbonate, extracting with chloroform, drying the chloroform extract over magnesium sulphate and concentrating gives the free base, 5.0 g. of which is then reacted with methyl isothiocyanate (1.94 g.) in ethanol (25 ml.) under reflux for 30 minutes. The product is purified on a column of alumina and elution with benzene gives N-methyl-N'-[2-((3-methyl-4-isothiazolyl)methylthio)ethyl]thiourea. Reaction of this product by the procedure of Example 121 gives N-cyano-N'-methyl-N''-[2-((3-methyl-4-isothiazolyl)methylthio)ethyl]guanidine.

Using the following halomethylisothiazoles as starting materials in the above procedure:
3-bromomethyl-5-chloroisothiazole
4-bromo-5-chloromethyl-3-methylisothiazole
the following products are obtained, respectively:
N-[2-((5-chloro-3-isothiazolyl)methylthio)ethyl]-N'-cyano-N''-methylguanidine
N-[2-((4-bromo-3-methyl-5-isothiazolyl)methylthio)ethyl]-N'-cyano-N''-methylguanidine.

Using the above procedure, 3-mercaptopropylamine in place of cysteamine, the product obtained is N-cyano-N'-methyl-N''-[3-((3-methyl-4-isothiazolyl)methylthio)propyl]guanidine.

EXAMPLE 124

2-(3-(Isothiazolylethylthio)ethylguanidine sulphate

Reacting 3-[(2-aminoethyl)thiomethyl]isothiazole with S-methylisothiouronium sulphate by the procedure of Example 1 gives the title compound.

EXAMPLE 125

Reacting 3-[(2-aminoethyl)thiomethyl]isothiazole with S-methyl-N-nitroisothiourea by the procedure of Example 2(ii) gives N-[2(3-isothiazolylmethylthio)ethyl]-N'-nitroguanidine and reaction of the same starting material with N,S-dimethyl-N'-nitroisothiourea by the procedure of Example 2(iii) gives N-[2-(3-isothiazolylmethylthio)ethyl]-N'-methyl-N''-nitroguanidine.

EXAMPLE 126

Reacting N-cyano-N'-[2-(3-isothiazolylmethylthio)ethyl]-S-methylisothiourea, prepared from 3-[(2-aminoethyl)thiomethyl]isothiazole by the procedure of EXample 3(c) (i), with ethylamine by the procedure of Example 4 gives N-cyano-N'-ethyl-N''-[2-(3-isothiazolylmethylthio)ethyl]guanidine.

By the same procedure, using propylamine and 2-(dimethylamino)ethylamine, the products are, respectively, N-cyano-N'-[2-(3-isothiazolylmethylthio)ethyl]-N''-propylguanidine and N-cyano-N'-(2-dimethylaminoethyl)-N''-[2-(3-isothiazolylmethylthi)ethyl]guanidine.

EXAMPLE 127

3,5-Dimethyl-4-isothiazolecarboxylic acid is converted to the methyl ester and the ester is reduced with lithium aluminium hydride in tetrahydrofuran to give 4-hydroxymethyl-3,5-dimethylisothiazole. Treating this hydroxymethyl compound with thionyl bromide gives 4-bromomethyl-3,5-dimethylisothiazole which is used as the starting material in the procedure of Example 121 to give N-cyano-N'-methyl-N''-[2-((3,5-dimethyl-4-isohiazolyl)methylthio)ethyl]guanidine.

By the same procedure, using 3,5-isothiazoledicarboxylic acid, the product is 3,5-bis-[2-(N-cyano-N'-methylguanidino)ethylthiomethyl]isothiazole.

EXAMPLE 128

N-CyanoN'-[3-(3-isothiazolylmethoxy)propyl]-N''-methylguanidine

Using 3-bromomethylisothiazole as the starting material in the procedure of Example 22 gives the title compound.

EXAMPLE 129

N-Cyano-N'-[2-(2--(3-isothiazolyl)ethyl)thioethyl]-N''-methylguanidine

3-Isothiazoleacetic acid is esterified and the ester is reduced with lithium aluminium hydride in tetrahydrofuran to give 3(2-hydroxyethyl)isothiazole. Reacting this hydroxyethyl compound with thionyl chloride gives 3-(2-chloroethyl)isothiazole which is used as the starting material in the procedure of Example 17 to give the title compound.

EXAMPLE 130

Using 3[(2-aminoethyl)thiomethyl]isothiazole as the starting material in Example 18 gives N-cyano-N'-[2-(3-isothiazolylmethylthio)ethyl]guanidine.

EXAMPLE 131

| Ingredients | Amounts |
| --- | --- |
| N-Cyano-N'-[2-(3-isothiazolylmethylthio)ethyl]N''-methylguanidine | 200 mg. |
| Lactose | 100 mg. |

The ingredients are mixed and filled into a hard gelatin capsule.

EXAMPLE 132

N-Cyano-N'-methyl-N''-[3-(2-oxazolyl)thiopropyl]-guanidine (i) Hydrochloric acid (90 ml.) was added to potassium thiocyanate in ethanol (1.8 l.) with stirring. Following filtration from inorganic matrerial, glycollaldehyde (35.9 g.) was added and the resulting solution was heated under reflux for 24 hours. Concentration, followed by cooling afforded a white solid, which following recrystallisation from ethanol afforded oxazole-2-thiol (30 g.), m.p. 143°–4°.

(ii) 3-Bromopropylphthalimide (13.4 g.) was added to a stirred solution of sodium ethoxide (from 1.15 g. sodium) and oxazole-2-thiol (5.1 g.) in ethanol (100 ml.). The resultant solution was heated under reflux for 2.5 hours and concentrated under reduced pressure. The residue was triturated with water (100 ml.) to afford 2-(3-phthalimidopropylthio)oxazole (14 g.) m.p. 101°. Recrystallisation from ethanol gave the pure oxazole, m.p. 102°–3°.

(iii) Hydrazine hydrate (5.3 g.) was added carefully to a solution of 2-(3-phthalimidopropylthio)oxazole (10 g.) in ethanol (173 ml.) with stirring. The solution was then heated under reflux for 25 minutes. After cooling, and filtration from phthalhydrazide, the filtrate was concentrated under reduced pressure and the residue was re-evaporated with ethanol to yield crude 2-(3-aminopropylthio)oxazole which was washed twice with ether and dissolved in ethanol (60 ml.). Methyl isothiocyanate (2.54 g.) was added and the solution was heated under reflux for 30 minutes. Following cooling and filtration from insoluble material, the filtrate was concentrated to an oil which was chromatographed on a column of silica gel with ethyl acetate as eluant. The product obtained crystallised from ethanol-ether-n-hexane to give N-methyl-N'-[3-(2-oxazolyl)thiopropyl]thiourea (2.4 g.). m.p. 43°–45°.

Reaction of N-methyl-N'-[3-(2-oxazoyl)thiopropyl]-thourea with lead cyanamide by the procedure of Example 121 gives the title compound.

EXAMPLE 133

N-Cyano-N'-methyl-N''-[3(4-methyl-2-oxazolyl)thiopropyl]-guanidine

The reaction of 4-methyloxazole-2-thiol (5.8 g.) with 3-bromopropylphthalimide (13.4 g.) using the conditions described in EXampe 132 afforded 4-methyl-2-(3-phthalimidopropylthio)oxazole (14 g.) m.p. 92°–93° (ethanol-ether).

Treatment of the phthalimide compound (3.0 g.) with hydrazine (1.53 g.) followed by reaction of the product directly with methyl isothiocyanate (0.73 g.) using the conditions described in Example 132 afforded N-methyl-N'-[3-(4-methyl-2-oxazolyl)thiopropyl]thiourea (1.0 g.), m.p. 73°–74° (from ethanol-ether-n-hexane).

Reaction of N-methyl-N'-[3-(4-methyl-2-oxazolyl)-thiopropyl]thiourea with lead cyanamide by the procedure of Example 121 gives the title compound.

EXAMPLE 134

Using the following 2-(chloroethyl)oxazoles as starting materials in the procedure of Example 17:
5-(2-chloroethyl)-4-methyloxazole
5-(2-chloroethyl)-4-trifluoromethyloxazole
the products are, respectively:
N-cyano-N'-methyl-N''-[2-(2-(4-methyl-5-oxazolyl)ethyl)-thioethyl]guanidine
N-cyano-N'-methyl-N''-[2-(2-(4-trifluoromethyl-5-oxazolyl)-ethyl)thioethyl]guanidine.

Also, using 2-amino-5-(2-chloroethyl)oxazole, prepared by reacting 2-amino-5-(2-hydroxyethyl)oxazole with thionyl chloride, in the procedure of Example 17 gives N-[2-(2-(2-amino-5-oxazolyl)ethyl)thioethyl]-N'-cyano-N''-methylguanidine.

EXAMPLE 135

Methyl 5-benzyl-4-oxazolecarboxylate is reduced with lithium aluminium hydride in tetrahydrofuran to give 5-benzyl-4-hydroxymethyloxazole, which by reacting with thionyl chloride is converted to 5-benzyl-4-chloromethyloxazole.

Using 5-benzyl-4-chloromethyloxazole as the starting material in the procedure of Example 1(i)(b) gives 4-[(2-aminoethyl)thiomethyl]-5-benzyloxazole.

Using the above prepared intermediate as the starting material in the procedure of Example 3(d) gives N-[2-((5-benzyl-4-oxazolyl)methylthio)ethyl]-N'-cyano-N''-methylguanidine.

Also, esterifying the following carboxylic acids and using the esters in the procedure described above:
2,5-dimethyl-4-oxazolecarboxylic acid
4,5-oxazoledicarboxylic acid
the products are, respectively:
N-cyano-N'-[2-((2,5-dimethyl-4-oxazolyl)methylthio)-ethyl]-N''-methylguanidine
4,5-bis-[2-(N-cyano-N'-methylguanidino)ethylthiomethyl]-oxazole.

Reacting 4-chloromethyl-2,5-dimethyloxazole, prepared from the corresponding carboxylic acid as described above, with 3-mercaptopropylamine by the procedure of Example 1(i)(b) and using the resulting 4-[(3-aminopropyl)-thiomethyl]-2,5-dimethyloxazole as the starting material in the procedure of Example 3(d) gives N-cyano-N'-[3-((2,5-dimethyl-4-oxazolyl)methylthio)propyl]-N''-methylguanidine.

Reduction of 5-chloro-2-methyl-4-oxazolecarboxylic acid with diborane, conversion of the resultant hydroxymethyl compound to 5-chloro-4-chloromethyl-2-methyloxazole and using this chloromethyl compound as the starting material gives, by the procedure of Example 1(i)(b) and 3(d), N-[2-((5-chloro-2-methyl-4-oxazolyl)methylthio)ethyl]-N'-cyano-N''-methylguanidine.

EXAMPLE 136

Reacting 2-(3-aminopropylthio)oxazole with dimethyl-N-cyanoimidodithiocarbonate by the procedure of Example 3(c)(i) gives N-cyano-N'-[3-(2-oxazolyl)thiopropyl]-S-methylisothiourea. Reacting this intermediate with ethylamine by the procedure of Example 4 gives N-cyano-N'-ethyl-N''-[3-(2-oxazolyl)thiopropyl]-guanidine.

Using 2-(dimethylamino)ethylamine in place of ethylamine gives N-cyano-N'-(2-dimethylaminoethyl)-N''-[3-(2-oxazolyl)thiopropyl]guanidine.

EXAMPLE 137

3-(2-Oxazolyl)thiopropylguanidine

Reacting 2-(3-aminopropylthio)oxazole with S-methylisothiourea by the procedure of Example 1 gives the title compound.

EXAMPLE 138

Reacting 2-(3-aminopropylthio)oxazole with S-methyl-N-nitroisothiourea by the procedure of Example 2(ii) gives N-nitro-N'-[3-(2-oxazolyl)thiopropyl]-guanidine. Similarly, reaction of the same starting material with N,S-dimethyl-N'-nitroisothiourea by the procedure of Example 2(iii) gives N-methyl-N'-nitro-N''-[3-(2-oxazolyl)thiopropyl]guanidine.

EXAMPLE 139

N-Cyano-N'-methyl-N''-[3-((5-methyl-4-oxazolyl)methoxy)-propyl]guanidine

Using 4-chloromethyl-5-methyloxazole as the starting material in the procedure of Example 22 gives the title compound.

EXAMPLE 140

Using 2-(3-aminopropylthio)oxazole as the starting material in the procedure of Example 18 gives N-cyano-N'-[3-(2-oxazolyl)thiopropyl]guanidine.

EXAMPLE 141

| Ingredients | Amounts |
| --- | --- |
| N-Cyano-N'-methyl-N''-[3-(4-methyl-2-oxazolyl)thiopropyl]guanidine | 200 mg. |
| Lactose | 100 mg. |

The ingredients are mixed and filled into a hard gelatin capsule.

EXAMPLE 142

(a) A solution of 3-chloromethylisoxazole (5.8 g.) and cysteamine hydrochloride (6.25 g.) in aqueous hydrobromic acid (48%, 100 ml) was heated under reflux for 6 hours. Concentration in the presence of water and subsequently n-propanol, followed by recrystallisation of the residue from isopropyl alcohol-ethanol afforded 3-[(2-aminoethyl)thiomethyl]isoxazole hydrobromide, m.p. 131°–133°. (Found: Br, 33.6; S, 13.7. $C_6H_{10}N_2O S \cdot H Br$ requires: Br, 33.4; S, 13.4).

(b) A solution of 3-[(2-aminoethyl)thiomethyl]isoxazole (2.44 g.) extracted from the hydrobromide and potassium carbonate with ether-ethanol (3:1) and ethyl isothiocyanate (1.36 g.) in absolute ethanol (40 ml.) was heated under reflux for 1.5 hours. Concentration followed by chromatographic purification on a column of silica gel with ether as eluant afforded N-methyl-N'-[2-(3-isoxazolylmethylthio)ethyl]thiourea as a colourless oil (2.5 g.). (Found: C, 41.3; H, 6.2; N, 18.2; S, 27.3. $C_8H_{13}N_2O_2S$ requires: C, 41.5; H, 5.7; N, 18.2; S, 27.7).

(c) Reaction of N-methyl-N'-[2-(3-isoxazolylmethylthio)-ethyl]thiourea with lead cyanamide by the procedure of Example 121 gives N-cyano-N'-methyl-N''-[2(3-isoxazolylmethylthio)ethyl]guanidine.

Hydrolysis of the last prepared compound according to the procedure of Example 3(e) gives N-methyl-N'-[2-(3-isoxazolylmethylthio)ethyl]guanidine hydrochloride.

EXAMPLE 143

Using the following chloromethylisoxazoles (prepared from the corresponding hydroxymethylisoxazoles by treatment thereof with thionyl chloride) as starting materials in the procedure of Example 142:

3-chloromethyl-5-methylisoxazole
3-bromo-5-chloromethylisoxazole
4-chloromethyl-3,5-dimethylisoxazole
4-(2-chloroethyl)-5-methylisoxazole the products are, respectively:

N-cyano-N'-methyl-N''-[2-(5-methyl-3-isoxazolylmethylthio)ethyl]guanidine

N-cyano-N'-methyl-N''-[2-(3-bromo-5-isoxazolymethylthio)ethyl]guanidine

N-cyano-N'-methyl-N''-[2-(3,5-dimethyl-4-isoxazolylmethylthio)ethyl]guanidine

N-cyano-N'-methyl-N''[2-(2-(5-methyl-4-isoxazolyl)ethylthio)ethyl]guanidine.

EXAMPLE 144

Using in the procedure of Example 142, 3-mercaptopropylamine in place of cysteamine the product is N-cyano-N'-methyl-N''-[3-(3-isoxazolylmethylthio)-propyl]guanidine.

EXAMPLE 145

Reaction of 3-[(2-aminoethyl)thiomethyl]isoxazole with S-methyl-isothiourea by the procedure of Example 1 gives [2-(3-isoxazolylmethylthio)ethyl]guanidine.

EXAMPLE 146

By the procedure of Example 22, 3-chloromethylisoxazole is used as the starting material to give N-cyano-N'-[2-(3-isoxazolylmethoxy)ethyl]-N''-methylguanidine.

EXAMPLE 147

3-[(2-Aminoethyl)thiomethyl]isoxazole is used as the starting material in the procedure of Example 18 to give N-cyano-N'-[2-(3-isoxazolylmethylthio)ethyl]guanidine.

EXAMPLE 148

Reaction of 3-[(2-aminoethyl)thiomethyl]isoxazole with dimethyl-N-cyanoimidodithiocarbonate by the procedure of Example 3(c)(i) gives N-cyano-N'-[2-(3-isoxazolylmethylthio)ethyl]-S-methylisothiourea. Reacting this intermediate with the following amines by the procedure of Example 4:

ethylamine
propylamine
2-(dimethylamino)ethylamine gives the following products, respectively:

N-cyano-N'-ethyl-N''-[2-(3-isoxazolylmethylthio)ethyl]guanidine

N-cyano-N'-propyl-N''-[2-(3-isoxazolylmethylthio)ethyl]guanidine

N-cyano-N'-(2-dimethylaminoethyl)-N''-[2-(3-isoxazolylmethylthio)ethyl]guanidine.

EXAMPLE 149

Reacting 3-[(2-aminoethyl)thiomethyl]isoxazole with S-methyl-N-nitroisothiourea by the procedure of Example 2(ii) gives N-nitro-N'-[2-(3-isoxazolylmethylthio)ethyl]guanidine.

Similarly, reaction of the same starting material with N,S-dimethyl-N'-nitroisothiourea by the procedure of Example 2(iii) gives N-methyl-N'-nitro-N''-[2-(3-isoxazolylmethylthio)ethyl]guanidine.

EXAMPLE 150

| Ingredients | Amounts |
| --- | --- |
| N-Cyano-N'-methyl-N''-[2-(3-isoxazolylmethylthio)ethyl]thiourea | 200 mg. |
| Lactose | 100 mg. |

The ingredients are mixed and filled into a hard gelatin capsule.

Compounds of formula I wherein A is such that there is formed together with the carbon atoms shown a five membered unsaturated heterocyclic ring having one nitrogen atom, one sulphur or oxygen atom and three carbon atoms, said unsaturated heterocyclic ring being thiazole, isothiazole, oxazole or isoxazole, and Y is NH are exemplified by the following examples.

EXAMPLE 151

Reacting 2-hydroxymethylthiazole with thionyl chloride, then using the resulting 2-chloromethylthiazole as the starting material in the procedure of Example 34 gives 2-(2-thiazolylmethylamino)ethylguanidine sulphate.

Similarly, from 4-hydroxymethylthiazole, 2-(4-thiazolylmethylamino)ethylguanidine sulphate is prepared.

EXAMPLE 152

(a) Reacting ethylenediamine with 2-chloromethylthiazole by the procedure of Example 34 gives N-(2-thiazolylmethyl)ethylenediamine. Reacting this intermediate with S-methyl-N-nitroisothiourea by the procedure of Example 2(ii) gives N-nitro-N'-[2-(2-thiazolylmethylamino)ethyl]guanidine. Treatment with hydrobromic acid gives the hydrobromide salt.

(b) Similarly, reaction of the same intermediate with N,S-dimethyl-N'-nitroisothiourea by the procedure of Example 2(iii) gives N-methyl-N'-nitro-N''-[2-(2-thiazolylmethylamino)ethyl]guanidine.

EXAMPLE 153

Reacting ethylenediamine with 2-chloromethylthiazole by the procedure of Example 34, then reacting the resulting N-(2-thiazolylmethyl)ethylenediamine with N-cyano-N',S-dimethylisothiourea by the procedure of Example 3(a), gives N-cyano-N'-methyl-N''-[2-(2-thiazolylmethylamino)ethyl]guanidine. Hydrolysis of this compound by the procedure of Example 3(e) gives N-methyl-N'-[2-(2-thiazolylmethylamino)ethyl]guanidine trihydrochloride.

EXAMPLE 154

Using, in the procedure of Example 153, N-(4-thiazolylmethyl)ethylenediamine (prepared by treating 4-hydroxymethylthiazole with thionyl chloride and reacting the resulting 4-chloromethylthiazole with ethylenediamine by the procedure of Example 34), N-cyano-N'-methyl-N''-[2-(4-thiazolylmethylamino)ethyl]guanidine is prepared.

Similarly, from 5-hydroxymethylthiazole, N-cyano-N'-methyl-N''-[2-(5-thiazolylmethylamino)ethyl]guanidine is prepared.

EXAMPLE 155

Reacting N-(2-thiazolylmethyl)ethylenediamine with ethyl isothiocyanate by the procedure of Example 3(b) and then chromatographing gives N-ethyl-N'-[2-(2-thiazolylmethylamino)ethyl]thiourea. Reacting this thiourea with lead cyanamide by the procedure of Example 3(b) gives N-cyano-N'-ethyl-N''-[2-(2-thiazolylmethylamino)ethyl]guanidine.

Using 2-dimethylaminoethyl isothiocyanate in place of ethyl isothiocyanate in the above procedure gives N-cyano-N'-(2-dimethylaminoethyl)-N''-[2-(2-thiazolylmethylamino)ethyl]guanidine.

EXAMPLE 156

Using, in the procedure of Example 153, the following haloalkylthiazoles (which may be prepared by treating the hydroxyalkylthiazoles with a thionyl halide):

2-amino-4-chloromethylthiazole
2-chloromethyl-4-methylthiazole
2-chloro-4-chloromethylthiazole
2-bromomethyl-4,5-dimethylthiazole
2-chloromethyl-4-ethyl-5-methylthiazole the products are, respectively:

N-[2-((2-amino-4-thiazolyl)methylamino)ethyl]-N'-cyano-N''-methylguanidine

N-cyano-N'-methyl-N''-[2-((4-methyl-2-thiazolyl)methylamino)ethyl]guanidine

N-[2-((2-chloro-4-thiazolyl)methylamino)ethyl]-N'-cyano-N''-methylguanidine

N-cyano-N'-methyl-N''-[2-((4,5-dimethyl-2-thiazolyl)methylamino)ethyl]guanidine

N-cyano-N'-[2-((4-ethyl-5-methyl-2-thiazolyl)methylamino)ethyl]-N'-methylguanidine.

Also, using as starting materials in the procedure of Example 153, the following chloromethylthiazoles (which may be prepared by converting the corresponding thiazolecarboxylic acid compounds to the hydroxymethylthiazoles by the procedure of Example 116 and then treating the hydroxymethylthiazoles with thionyl chloride):

2-benzyl-4-chloromethylthiazole
2,4-di(chloromethyl)thiazole
5-bromo-2-chloromethyl-4-methylthiazole
4-chloromethyl-2hydroxythiazole the products are, respectively:

N-[2-((2-benzyl-4-thiazolyl)methylamino)ethyl]-N'-cyano-N''-methylguanidine 2,4-bis-[2-(N-cyano-N'-methylguanidino)ethylaminomethyl]thiazole N-[2-((5-bromo-4-methyl-2-thiazolyl)methylamino)ethyl]-N'-cyano-N''-methylguanidine N-cyano-N'-[2-((2-hydroxy-4-thiazolyl)methylamino)ethyl]-N''-methylguanidine.

Using, in the procedure of Example 153, 1,3-diaminopropane in place of ethylenediamine, the product is N-cyano-N'-methyl-N''-[3-(2-thiazolylmethylamino)-propyl]guanidine.

EXAMPLE 157

N-Cyano-N'-methyl-N''-[3-(2-thiazolylamino)propyl]-guanidine

Using 2-aminothiazole as the starting material in the procedure of Example 40 gives the title compound.

EXAMPLE 158

Using 2-(3-aminopropylamino)thiazole as the starting material in the procedure of Example 18 gives N-cyano-N'-[3-(2-thiazolylamino)propyl]guanidine.

EXAMPLE 159

| Ingredients | Amounts |
| --- | --- |
| N-Cyano-N'-methyl-N''-[2-(2-thiazolyl-methylamino)ethyl]guanidine | 200 mg. |
| Lactose | 100 mg. |

The ingredients are mixed and filled into a hard gelatin capsule.

EXAMPLE 160

2-(3-Isothiazolylmethylamino)ethylguanidine sulphate

By the procedure of Example 34, ethylenediamine is reacted with 3-bromomethylisothiazole to give N-(3-isothiazolylmethyl)ethylenediamine. This intermediate is heated under reflux with S-methylisothiouronium sulphate in water for 3 hours by the procedure of Example 1 to give the title compound.

EXAMPLE 161

Reaction of N-(3-isothiazolylmethyl)ethylenediamine with S-methyl-N-nitroisothiourea by the procedure of Example 2(ii) gives N-[2-(3-isothiazolylmethylamino)ethyl]-N'-nitroguanidine.

Similarly, reaction of the same starting material with N,S-dimethyl-N'-nitroisothiourea by the procedure of Example 2(iii) gives N-[2-(3-isothiazolylmethylamino)ethyl]-N'-methyl-N''-nitroguanidine.

EXAMPLE 162

Reaction of 3-bromomethylisothiazole with ethylenediamine by the procedure of Example 34 and reaction of the resulting N-(3-isothiazolylmethyl)ethylenediamine with methyl isothiocyanate by the procedure of Example 3(b) and then chromatographing gives N-methyl-N'-[2-(3-isothiazolylmethylamino)ethyl]thiourea. This intermediate is reacted with lead cyanamide by the procedure of Example 3(b) to give N-cyano-N'-[2-(3-isothiazolylmethylamino)ethyl]-N''-methylguanidine. Hydrolysis of the last prepared compound by the procedure of Example 3(e) gives N-[2-(3-isothiazolylmethylamino)ethyl]-N'-methylguanidine dihydrochloride.

EXAMPLE 163

Using ethyl isothiocyanate in place of methyl isothiocyanate in the procedure of Example 162 gives N-cyano-N'''-[2-(3-isothiazolylmethylamino)ethyl]guanidine.

By the same procedure, using 2-dimethylaminoethyl isothiocyanate, N-cyano-N'-(2-dimethylaminoethyl)-N''-[2-(3-isothiazolylmethylamino)ethyl]guanidine is prepared.

EXAMPLE 164

Using, in the procedure of Example 162, the following haloalkylisothiazoles:
4-bromo-3-bromomethylisothiazole
3-bromomethyl-5-chloroisothiazole
4-bromo-5-chloromethyl-3-methylisothiazole
4-chloromethyl-3-methylisothiazole
4-bromomethyl-3,5-dimethylisothiazole
3,5-di(bromomethyl)isothiazole
3-(2-chloroethyl)isothiazole
the products are, respectively:
N-[2-((4-bromo-3-isothiazolyl)methylamino)ethyl]-N'-cyano-N''-methylguanidine
N-[2-((5-chloro-3-isothiazolyl)methylamino)ethyl]-N'-cyano-N''-methylguanidine
N-[2-((4-bromo-3-methyl-5-isothiazolyl)methylamino)ethyl]-N'-cyano-N''-methylguanidine
N-cyano-N'-methyl-N''-[2-((3-methyl-4-isothiazolyl)methylamino)ethyl]guanidine
N-cyano-N'-methyl-N''-[2-((3,5-dimethyl-4-isothiazolyl)methylamino)ethyl]guanidine
3,5-bis-[2-(N-cyano-N'-methylguanidino)ethylaminomethyl]isothiazole
N-cyano-N'-[2-(2-(3-isothiazolyl)ethyl)aminoethyl]-N''-methylguanidine.

Using, in the procedure of Example 162, 1,3-diaminopropane in place of ethylenediamine, the product is N-cyano-N'-[3-(3-isothiazolylmethylamino)propyl]-N''-methylguanidine.

EXAMPLE 165

Using 3-aminoisothiazole as the starting material in the procedure of Example 40 gives 3-(3-aminopropylamino)isothiazole.

Using 3-(3-aminopropylamino)isothiazole as the starting material in the procedure of Example 3 gives N-cyano-N'-[3-(3-isothiazolylamino)propyl]-N''-methylguanidine.

EXAMPLE 166

Using 3-(3-aminopropylamino)isothiazole as the starting material in the procedure of Example 18 gives N-cyano-N'-[3-(3-isothiazolylamino)propyl]guanidine.

EXAMPLE 167

| Ingredients | Amounts |
| --- | --- |
| N-Cyano-N'-[2-(3-isothiazolyl-methylamino)ethyl]-N''-methyl-guanidine | 150 mg. |
| Lactose | 100 mg. |

The ingredients are mixed and filled into a hard gelatin capsule.

EXAMPLE 168

Using the following chloroethyloxazoles as starting materials in the procedure of Example 34:
5-(2-chloroethyl)-4-methyloxazole
5-(2-chloroethyl)-4-trifluoromethyloxazole
2-amino-5-(2-chloroethyl)oxazole
the following products are obtained, respectively:
2-[2-(4-methyl-5-oxazolyl)ethylamino]ethylguanidine
2-[2-(4-trifluoromethyl-5-oxazolyl)ethylamino]ethylguanidine
2-[2-(2-amino-5-oxazolyl)ethylamino]ethylguanidine.

EXAMPLE 169

5-Benzyl-4-oxazolecarboxylic acid is converted to 5-benzyl-4-hydroxymethyloxazole by the procedure of Example 135. Treating this hydroxymethyl compound with thionyl chloride gives 5-benzyl-4-chloromethyloxazole.

Reacting ethylenediamine with 5-benzyl-4-chloromethyloxazole by the procedure of Example 34, then reacting the resulting N-(5-benzyl-4-oxazolylmethyl)ethylenediamine with methyl isothiocyanate by the procedure of Example 3(b) and chromatographing gives N-methyl-N'-[2-((5-benzyl-4-oxazolyl)methylamino)ethyl]-thiourea. Reacting this thiourea with lead cyanamide by the procedure of Example 3(b) gives N-[2-((5-benzyl-4-oxazolyl)methylamino)ethyl]-N'-cyano-N''-methylguanidine.

By the same procedure, using the following compounds as the starting materials:
2,5-dimethyl-4-oxazolecarboxylic acid
4,5-oxazoledicarboxylic acid
the following products are obtained, respectively:
N-cyano-N'-[2-((2,5-dimethyl-4-oxazolyl)methylamino)ethyl]-N''-methylguanidine
4,5-bis-[2-(N-cyano-N'-methylguanidino)ethylaminomethyl]oxazole.

Reduction of 5-chloro-2-methyl-4-oxazolecarboxylic acid with diborane and treatment of the resultant hydroxymethyl compound with thionyl chloride gives 5-chloro-4-chloromethyl-2-methyloxazole which, by the above procedure, is converted to N-[2-((5-chloro-2-methyl-4-oxazolyl)methylamino)ethyl]-N'-cyano-N''-methylguanidine.

EXAMPLE 170

Using 5-chloromethyl-4-methyloxazole as the starting material, by the procedures of Example 152(a) and (b), N-[2-((4-methyl-5-oxazolyl)methylamino)ethyl]-N'-nitroguanidine and N-methyl-N'-[2-((4-methyl-5-oxazolyl)methylamino)ethyl]-N''-nitroguanidine are prepared.

EXAMPLE 171

Reaction of 5-chloromethyl-4-methyloxazole with ethylenediamine by the procedure of Example 34 and reaction of the resulting N-(4-methyl-5-oxazolylmethyl)ethylenediamine with ethyl isothiocyanate by the procedure of Example 3(b) gives, after purifying by column chromatography, N-ethyl-N'-[2-(4-methyl-5-oxazolylmethylamino)ethyl]thiourea. This thiourea is reacted with lead cyanamide by the procedure of Example 3(b) to give N-cyano-N'-ethyl-N''-[2-((4-methyl-5-oxazolyl)methylamino)ethyl]guanidine.

By the same procedure, using 2-dimethylaminoethyl isothiocyanate in place of ethyl isothiocyanate, N-cyano-N'-(2-dimethylaminoethyl)-N''-[2-((4-methyl-5-oxazolyl)-methylamino)ethyl]guanidine is prepared.

Using 1,3-diaminopropane in place of ethylenediamine and methyl isothiocyanate in place of ethyl isothiocyanate in the above procedure gives N-cyano-N'-methyl-N''-[3-((4-methyl-5-oxazolyl)methylamino)-propyl]guanidine.

EXAMPLE 172

| Ingredients | Amounts |
| --- | --- |
| N-[2-((4-Methyl-5-oxazolyl)methylamino)ethyl]-N'-cyano-N''-methylguanidine | 200 mg. |
| Lactose | 100 mg. |

The ingredients are mixed and filled into a hard gelatin capsule.

EXAMPLE 173

Using, in the procedure of Example 153, the following chloroalkylisoxazoles:
3-chloromethylisoxazole
3-chloromethyl-5-methylisoxazole
3-bromo-5-chloromethylisoxazole
4-chloromethyl-3,5-dimethylisoxazole
4-(2-chloroethyl)-5-methylisoxazole
the products are, respectively:
N-cyano-N'-methyl-N''-[2-(3-isoxazolylmethylamino)ethyl]guanidine
N-cyano-N'-methyl-N''-[2-(5-methyl-3-isoxazolylmethylamino)ethyl]guanidine
N-cyano-N'-methyl-N''-[2-(3-bromo-5-isoxazolylmethylamino)ethyl]guanidine
N-cyano-N'-methyl-N''-[2-(3,5-dimethyl-4-isoxazolylmethylamino)ethyl]guanidine
N-cyano-N'-methyl-N''-[2-(2-(5-methyl-4-isoxazolyl)ethylamino)ethyl]guanidine.

EXAMPLE 174

Using in the procedure of Example 153, 3-chloromethylisoxazole and 1,3-diaminopropane as the starting materials, the product is N-cyano-N'-methyl-N''-[3-(3-isoxazolylmethylamino)propyl]guanidine.

EXAMPLE 175

3-Chloromethylisoxasole is used as starting material in the procedure of Example 34 to give 2-(3-isoxazolylmethylamino)ethylguanidine.

EXAMPLE 176

By the procedure of Example 155, N-(3-isoxazolylmethyl)ethylenediamine is reacted with the following isothiocyanates:
ethyl isothiocyanate
propyl isothiocyanate
2-dimethylaminoethyl isothiocyanate
and the resulting thiourea intermediates are reacted with lead cyanamide by the procedure of Example 3(b) to give the following products, respectively:
N-cyano-N'-ethyl-N''-[2-(3-isoxazolylmethylamino)ethyl]guanidine
N-cyano-N'-propyl-N''-[2-(3-isoxazolylmethylamino)ethyl]guanidine
N-cyano-N'-(2-dimethylaminoethyl)-N''-[2-(3-isoxazolylmethylamino)ethyl]guanidine.

EXAMPLE 177

Using 3-chloromethylisoxazole as the starting material, by the procedures of Example 152(a) and (b), N-[2-(3-isoxazolylmethylamino)ethyl]-N'-nitroguanidine and N-[2-(3-isoxazolylmethylamino)ethyl]-N'-methyl-N''-nitroguanidine are prepared.

EXAMPLE 178

| Ingredients | Amounts |
| --- | --- |
| N-Cyano-N'-methyl-N''-[2-(3-isoxazolyl-methylamino)ethyl]guanidine | 200 mg. |
| Lactose | 100 mg. |

The ingredients are mixed and filled into a hard gelatin capsule.

Compounds of formula I where A is such that there is formed together with the carbon atom shown a triazole ring and Y is oxygen or sulphur (sulphur is preferred) are exemplified by the following examples.

EXAMPLE 179

2-[3-(1,2,4-triazolyl)methylthio]ethylguanidine sulphate

By the procedure of Example 1, 3-[(2-aminoethyl)thiomethyl]-1,2,4-triazole dihydrobromide, m.p. 177°–179°, was prepared.

This amine salt is converted to the free base and reacted with S-methylisothiouronium sulphate by the procedure of Example 1 to give the title compound.

EXAMPLE 180

Treatment of 3-[(2-aminoethyl)thiomethyl]-1,2,4-triazole with dimethyl-N-cyanoimidodithiocarbonate and then with methylamine by the procedure of Example 3(c) gives N-cyano-N'-methyl-N''-[2-(3-(1,2,4-triazolyl)methylthio)ethyl]guanidine.

Hydrolysis of this compound by the method of Example 3(e) gives N-methyl-N'-[2-(3-(1,2,4-triazolyl)methylthio)ethyl]guanidine dihydrochloride.

EXAMPLE 181

2-[4-Methyl-3-(1,2,4-triazolyl)methylthio]ethylguanidine sulphate

Ethoxyacetyl chloride (57 g.) was added slowly to a stirred solution of 4-methylthiosemicarbazide (53.5 g.) in dry pyridine (500 ml.) at 0°–5°. The mixture was allowed to attain room temperature and stirring was continued for 18 hours. Following concentration under reduced pressure the residue was treated with a solution of sodium (21.4 g.) in ethanol (500 ml.) and the mixture was heated under reflux for 24 hours. Following concentration and acidification with hydrochloric acid a solid was obtained. After partial concentration the solid was collected and recrystallised from ethyl acetate to give 3-ethoxymethyl-4-methyl-1,2,3-triazoline-5-thione (53 g.), m.p. 137°–138°. The thione (44 g.) was desulphurised by slow addition to a solution prepared from nitric acid (75 ml.) water (150 ml.) and sodium nitrite (1.5 g.) at 15°–20°. Following subsequent basification with sodium carbonate and concentration the residue was extracted with ethanol-ether 1:1 and distilled to afford 3-ethoxymethyl-4-methyl-1,2,4-triazole (30 g.) b.p. 154°–156°/0.05 mm. The above compound (15 g.) dissolved in 48% aqueous hydrobromic acid (150 ml.) was heated under reflux for 24 hours and concentrated to dryness to give 3-hydroxymethyl-4-methyl-1,2,4-triazole.

Reaction of 3-hydroxymethyl-4-methyl-1,2,4-triazole with cysteamine hydrochloride and hydrobromic acid by the procedure of Example 1 gives 3-[(2-aminoethyl)-thiomethyl]-4-methyl-1,2,4-triazole dihydrobromide, m.p. 175°–177°.

The above prepared dihydrobromide salt is converted to the free base by the procedure of Example 1. Reaction of 3-[(2-aminoethyl)thiomethyl]-4-methyl-1,2,4-triazole with S-methylisothiouronium sulphate by the procedure of Example 1 gives the title compound.

EXAMPLE 182

3,5-bis-[2-(N-Cyano-N'-methylguanidino)ethylthiomethyl]-1,2,4-triazole (i) The reaction of 3,5-dihydroxymethyl-1,2,4-triazole (9.0 g; obtained from 1,2,4-triazole and excess formaldehyde at elevated temperatures) with cysteamine hydrochloride (17.3 g.) by the procedure described in Example 1 (i)(a) afforded 3,5-bis-((2-aminoethyl)thiomethyl)-1,2,4-triazole trihydrobromide (4.7 g.), m.p. 214°–215°.

(ii) The reaction of 3,5-bis-((2-aminoethyl)thiomethyl)-1,2,4-triazole(from 6.5 g. trihydrobromide) with methyl isothiocyanate (1.93 g.) afforded the bis-thiourea which was purified by passage through a column of silica gel with ethanol as eluant. Trituration with isopropyl acetate, followed by recrystallisation from ethanol-ether afforded 3,5-bis-[2-N-methylthioureido)ethylthiomethyl]-1,2,4-triazole (0.9 g.) m.p. 133°–135°.

(iii) The reaction of 3,5-bis-[2-(N-methylthioureido)ethylthiomethyl]-1,2,4-triazole with lead cyanamide by the procedure of Example 3(b) gives the title compound.

EXAMPLE 183

The reaction of 3-[(2-aminoethyl)thiomethyl]-4-methyl-1,2,4-triazole with S-methyl-N-nitroisothiourea by the procedure of Example 2(ii) gives N-(2-(4-methyl-3-(1,2,4-triazolyl)methylthio)ethyl]-N'-nitroguanidine. Reaction of the same starting material with N,S-dimethyl-N'-nitroisothiourea by the procedure of Example 2(iii) gives N-methyl-N'-[2-(4-methyl-3-(1,2,4-triazolyl)-methylthio)ethyl]-N''-nitroguanidine.

EXAMPLE 184

By the procedure of Example 1, the following hydroxymethyl triazoles:

2-benzyl-3-hydroxymethyl-1,2,4-triazole
3-amino-5-hydroxymethyl-1,2,4-triazole
3-bromo-5-hydroxymethyl-1,2,4-triazole
1-benzyl-4-hydroxymethyl-1,2,3-triazole are converted to the corresponding (2-aminoethyl)thiomethyl triazoles and these intermediates are reacted with dimethyl-N-cyanoimidodithiocarbonate and methylamine by the procedure of Example 3(c) to give the following products, respectively:

N-[2-(2-benzyl-3-(1,2,4-triazolyl)methylthio)ethyl]N'-cyano-N''-methylguanidine
N-[2-(3-amino-5-(1,2,4-triazolyl)methylthio)ethyl]N'-cyano-N''-methylguanidine
N-[2-(3-bromo-5-(1,2,4-triazolyl)methylthio)ethyl]N'-cyano-N''-methylguanidine
N-[2-(1-benzyl-4-(1,2,3-triazolyl)methylthio)ethyl]N'-cyano-N''-methylguanidine

EXAMPLE 185

Converting 5-methyl-4-(1,2,3-triazole)carboxylic acid to the methyl ester and then reducing the ester with lithium aluminum hydride in tetrahydrofuran gives 4-hydroxymethyl-5-methyl-1,2,3-triazole.

Converting 4-hydroxymethyl-5-methyl-1,2,3-triazole to 4-[(2-aminoethyl)thiomethyl]-5-methyl-1,2,3-triazole by the procedure of Example 1 and using this intermediate as the starting material in the procedure of Example 3 gives N-cyano-N'-methyl-N''-[2-(5-methyl-4-(1,2,3-triazolyl)methylthio)ethyl]guanidine.

By the same procedure, using the following ethyl triazolecarboxylate compounds:

diethyl 4,5-(1,2,3-triazole)dicarboxylate ethyl 3-hydroxy-5-(1,2,4-triazole)carboxylate(prepared by esterification of the corresponding acid)
ethyl 5-amino-4-(1,2,3-triazole)carboxylate
ethyl 5-hydroxy-4-(1,2,3-triazole)carboxylate
the following products are obtained, respectively:
4,5-bis-[2-(N-cyano-N'-methylguanidino)ethylthiomethyl]-1,2,3-triazole
N-cyano-N'-[2-(3-hydroxy-5-(1,2,4-triazolyl)methylthio)ethyl]-N''-methylguanidine
N-[2-(5-amino-4-(1,2,3-triazolyl)methylthio)ethyl]-N'-cyano-N''-methylguanidine
N-cyano-N'-[2-(5-hydroxy-4-(1,2,3-triazolyl)methylthio)ethyl]-N'-methylguanidine.

Reduction of 3-chloro-5-(1,2,4-triazole)carboxylic acid with diborane gives the corresponding hydroxymethyl compound and, using this as starting material in the above process, gives N-[2-(3-chloro-5-(1,2,4-triazolyl)methylthio)ethyl]-N'-cyano-N''-methylguanidine.

Reacting 4-hydroxymethyl-5-methyl-1,2,3-triazole with 3-mercaptopropylamine by the procedure of Example 1 and using the resulting 4-[(3-aminopropyl)thiomethyl]-5-methyl-1,2,3-triazole as the starting material in the procedure of Example 3 gives N-cyano-N'-methyl-N''-[3-(5-methyl-4-(1,2,3-triazolyl)methylthio)-propyl]-guanidine.

EXAMPLE 186

Reaction of 3-[(2-aminoethyl)thiomethyl]-4-methyl-1,2,4-triazole with dimethyl-N-cyanoimidodithiocarbonate by the procedure of Example 3(c)(i) gives N-cyano-N'-[2-(4-methyl-3-(1,2,4-triazolyl)methylthio)ethyl]-S-methylisothiourea. Reaction of this intermediate with ethylamine by the procedure of Example 4 gives N-cyano-N'-ethyl-N''-[2-(4-methyl-3-(1,2,4-triazolyl)-methylthio)ethyl]guanidine.

Using propylamine in place of ethylamine gives N-cyano-N'-[2 -(4-methyl-3-(1,2,4-triazolyl)methylthio)ethyl]-N''-propylguanidine.

EXAMPLE 187

Using 3-mercapto-1,2,4-triazole as the starting material in the procedure of Example 20 gives N-cyano-N'-methyl-N''-[3-(3-(1,2,4-triazolyl)thio)propyl]-guanidine.

Using 4-mercapto-1,2,3-triazole, the product is N-cyano-N'-methyl-N''-[3-(4-(1,2,3-triazolyl)thio)-propyl]guanidine.

EXAMPLE 188

Using 3-(2-chloroethyl)-1,2,4-triazole as the starting material in the procedure of Example 17 gives N-cyano-N'-methyl-N''-[2-(2-(3-(1,2,4-triazolyl)ethyl)-thioethyl]-guanidine.

EXAMPLE 189

N-Cyano-N'-methyl-N''-[3-(3-(1,2,4-triazolyl)methoxy)-propyl]guanidine

Using 3-chloromethyl-1,2,4-triazole as the starting material in the procedure of Example 22 gives the title compound.

EXAMPLE 190

Using 3-[(2-aminoethyl)thiomethyl]-4-methyl-1,2,4-triazole as the starting material in the procedure of Example 18 gives N-cyano-N'-[2-(4-methyl-3-(1,2,4-triazolyl)methylthio)ethyl]guanidine.

By the same procedure, using 4-[(2-aminoethyl)thiomethyl]-5-methyl-1,2,3-triazole, N-cyano-N'-[2-(5-methyl-4-(1,2,3-triazolyl)methylthio)ethyl]guanidine is prepared.

EXAMPLE 191

| Ingredients | Amounts |
|---|---|
| N-Cyano-N'-methyl-N''-[2-(3-(1,2,4-triazolyl)methylthio)ethyl]guanidine | 200 mg. |
| Lactose | 100 mg. |

The ingredients are mixed and filled into a hard gelatin capsule.

Compounds of formula I wherein A is such that there is formed together with the carbon atom shown a triazole ring and Y is NH are exemplified by the following examples.

EXAMPLE 192

2-[3-(1,2,4-Triazolyl)methylamino]ethylguanidine sulphate

By the procedure of Example 34, ethylenediamine is reacted with 3-chloromethyl-1,2,4-triazole to give N-[3-(1,2,4-triazolyl)methyl]ethylenediamine.

The above prepared compound is heated under reflux with S-methylisothiouronium sulphate in water for 3 hours by the procedure of Example 1 to give the title compound.

EXAMPLE 193

Reacting N-[3-(1,2,4-triazolyl)methyl]-ethylenediamine with S-methyl-N-nitroisothiourea by the procedure of Example 2(ii) gives N-nitro-N'-[2-(3-(1,2,4-triazolyl)methylamino)ethyl]guanidine.

Treatment of the product with hydrobromic acid gives the hydrobromide salt. Treatment of the same starting material with N,S-dimethyl-N'-nitroisothiourea by the procedure of Example 2(iii) gives N-methyl-N'-nitro-N''[2-(3-(1,2,4-triazolyl)methylamino)ethyl]guanidine.

EXAMPLE 194

Treating 4-hydroxymethyl-5-methyl-1,2,3-triazole with thionyl chloride gives 4-chloromethyl-5-methyl-1,2,3-triazole. Reacting ethylenediamine with 4-chloromethyl-5-methyl-1,2,3-triazole and reacting the resulting N-[5-methyl-4-(1,2,3-triazolyl)methyl]ethylenediamine with S-methylisothiouronium sulphate by the procedure of Example 1 gives 2-[5-methyl-4-(1,2,3-triazoly)methylamino]ethylguanidine sulphate.

Using N-[5-methyl-4-(1,2,3-triazolyl)methyl]ethylenediamine in the procedure of Example 35 gives N-nitro-N'-[2-(5-methyl-4-(1,2,3-triazolyl)methylamino)ethyl]guanidine.

EXAMPLE 195

Reacting 3-chloromethyl-1,2,4-triazole with ethylenediamine by the procedure of Example 34, then reacting the resulting N-[3-(1,2,4-triazolyl)methyl]ethylenediamine with methyl isothiocyanate by the procedure of Example 3(b), then chromatographing gives N-methyl-N'-[2-(3-(1,2,4-triazolyl)methylamino)ethyl]thiourea. This thiourea is reacted with lead cyanamide by the procedure of Example 3(b) to give N-cyano-N'-methyl-N''-[2-(3-(1,2,4-triazolyl)methylamino)ethyl]guanidine. Hydrolysis of this compound by the procedure of Example 3(e) gives N-methyl-N'-[2-(3-(1,2,4-triazolyl)methylamino)ethyl]guanidine trihydrochloride.

EXAMPLE 196

Ethylenediamine is reacted with 4-chloromethyl-5-methyl-1,2,3-triazole by the procedure of Example 34 and the resulting N-[5-methyl-4-(1,2,3-triazolyl)methyl]ethylenediamine is reacted with methyl isothiocyanate by the procedure of Example 3(b) to give, after chromatographing, N-methyl-N'-[2-(5-methyl-4-(1,2,3-triazolyl)methylamino)ethyl]thiourea. This thiourea is reacted with lead cyanamide by the procedure of Example 3(b) to give N-cyano-N'-methyl-N''-[2-(5-methyl-4-(1,2,3-triazolyl)methylamino)ethyl]guanidine.

Using ethyl isothiocyanate is place of methyl isothiocyanate in the above procedure gives N-cyano-N'-ethyl-N''-[2-(5-methyl-4-(1,2,3-triazolyl)methylamino)ethyl]guanidine.

EXAMPLE 197

Using 2-dimethylaminoethyl isothiocyanate in place of methyl isothiocyanate in the procedure of Example 196 gives N-cyano-N'-(2-dimethylaminoethyl)-N''-[2-(5-methyl-4-(1,2,3-triazolyl)methylamino)ethyl]guanidine.

Using in the procedure of Example 196, N-[3-(1,2,4-triazolyl)methyl]ethylenediamine and 2-dimethylaminoethyl isothiocyanate gives N-cyano-N'-(2-dimethylaminoethyl)-N''-[2-(3-(1,2,4-triazolyl)methylamino)ethyl]guanidine.

EXAMPLE 198

Using, in the procedure of Example 195, the following chloroalkyltriazoles (which may be prepared by treating the corresponding hydroxyalkyltriazoles with thionyl chloride):
3-(2-chloroethyl)-1,2,4-triazole
3-chloromethyl-4-methyl-1,2,4-triazole
3,5-di(chloromethyl)-1,2,4-triazole
3-chloromethyl-2-benzyl-1,2,4-triazole
3-amino-5-chloromethyl-1,2,4-triazole
3-bromo-5-chloromethyl-1,2,4-triazole
the products are, respectively:
N-cyano-N'-methyl-N''-[2-(2-(3-(1,2,4-triazolyl))ethylamino)ethyl]guanidine
N-cyano-N'-methyl-N''-[2-(4-methyl-3-(1,2,4-triazolyl)methylamino)ethyl]guanidine
3,5-bis-[2-(N-cyano-N'-methylguanidino)ethylaminomethyl]-1,2,4-triazole
N-[2-(2-benzyl-3-(1,2,4-triazolyl)methylamino)ethyl]-N'-cyano-N''-methylguanidine
N-[2-(3-amino-5-(1,2,4-triazolyl)methylamino)ethyl]-N'-cyano-N''-methylguanidine
N-[2-(3-bromo-5-(1,2,4-triazolyl)methylamino)ethyl]-N'-cyano-N''-methylguanidine.

Using in the procedure of Example 195, 1,3-diaminopropane in place of ethylenediamine, the product is N-cyano-N'-methyl-N''-[3-(3-(1,2,4-triazolyl)methylamino)propyl]guanidine.

EXAMPLE 199

Using in the procedure of Example 195, the following chloroalkyltriazoles, prepared from the corresponding hydroxyalkyl compounds by reacting with thionyl chloride:
1-benzyl-4-chloromethyl-1,2,3-triazole
4-chloromethyl-5-methyl-1,2,3-triazole
5-amino-4-chloromethyl-1,2,3-triazole
4-chloromethyl-5-hydroxy-1,2,3-triazole
4,5-di(chloromethyl)-1,2,3-triazole
3-chloro-5-chloromethyl-1,2,4-triazole
3-hydroxy-5-chloromethyl-1,2,4-triazole
the products are, respectively:
N-[2-(1-benzyl-4-(1,2,3-triazolyl)methylamino)ethyl]-N'-cyano-N''-methylguanidine
N-cyano-N'-methyl-N''-[2-(5-methyl-4-(1,2,3-triazolyl)methylamino)ethyl]guanidine
N-[2-(5-amino-4-(1,2,3-triazolyl)methylamino)ethyl]-N'-cyano-N''-methylguanidine
N-cyano-N'-[2-(5-hydroxy-4-(1,2,3-triazolyl)methylamino)ethyl]-N''-methylguanidine
4,5-bis-[2-(N-cyano-N'-methylguanidino)ethylaminomethyl]-1,2,3-triazole
N-[2-(3-chloro-5-(1,2,4-triazolyl)methylamino)ethyl]-N'-cyano-N''-methylguanidine
N-cyano-N'-[2-(3-hydroxy-5-(1,2,4-triazolyl)methylamino)ethyl]-N''-methylguanidine.

EXAMPLE 200

A mixture of 3-chloro-1,2,4-triazole (10.3 g., 0.1 m.) and 1,3-diaminopropane (7.4 g, 0.1 m.) in ethanol containing sodium ethoxide is allowed to stand overnight. The solvent is removed to give 3-(3-aminopropylamino)-1,2,4-triazole and this intermediate is reacted with dimethyl-N-cyanoimidodithiocarbonate and methylamine by the procedure of Example 3(d) to give N-cyano-N'-methyl-N''-[3-(3-(1,2,4-triazolyl)amino)propyl]guanidine.

By the same procedure, using 4-chloro-5-methyl-1,2,3-triazole as the starting material, the intermediate 4-(3-aminopropylamino)-5-methyl-1,2,3-triazole and the product N-cyano-N'-methyl-N''- [3-(5-methyl-4-(1,2,3-triazolyl)amino)propyl]guanidine are prepared.

EXAMPLE 201

By the procedure of Example 18, 3-(3-aminopropylamino)-1,2,4-triazole is used as the starting material to give N-cyano-N''-[3-(3-(1,2,4-triazolyl)amino)propyl]guanidine.

By the same procedure, using 4-(3-aminopropylamino)-5-methyl-1,2,3-triazole, there is obtained N-cyano-N'-[3-(5-methyl-4-(1,2,3-triazolyl)amino)propyl]guanidine.

EXAMPLE 202

| Ingredients | Amounts |
| --- | --- |
| N-Cyano-N'-methyl-N''-[2-(3-(1,2,4-triazolyl)methylamino)ethyl]guanidine | 200 mg. |

| Ingredients | Amounts |
| --- | --- |
| Lactose | 100 mg. |

The ingredients are mixed and filled into a hard gelatin capsule.

Similarly, a capsule is prepared using 200 mg. of N-cyano-N'-methyl-N''-[2-(5-methyl-4-(1,2,3-triazolyl)-methylamino)ethyl]guanidine.

Compounds of formula I wherein A is such that there is formed together with the carbon atom shown a thiadiazole ring and Y is oxygen or sulphur (sulphur is preferred) are exemplified by the following examples.

EXAMPLE 203

2-(2-Amino-5-(1,3,4-thiadiazolyl)methylthio)ethylguanidine sulphate

By the procedure of Example 1, the following intermediate amine salt was prepared: 2-amino-5-(2-aminoethyl)thiomethyl-1,3,4-thiadiazole dihydrobromide, m.p. 229°–232° C. By the procedure of Example 1 converting this salt to the free base and then reacting with S-methylisothiouronium sulphate gives the title compound.

EXAMPLE 204

By the procedure of Example 20, using 2-amino-5-mercapto-1,3,4-thiadiazole as the starting material, the following intermediate dihydrobromide salt was prepared: 2-amino-5-(3-aminopropylthio)-1,3,4-thiadiazole dihydrobromide, m.p. 185°–188° C.

The above prepared dihydrobromide salt is converted to the free base and reacted with dimethyl-N-cyanoimidodithiocarbonate and then with methylamine by the procedure of Example 3(c) to give N-[3-(2-amino-5-(1,3,4-thiadiazolyl)thio)propyl]-N'-cyano-N''-methylguanidine. Hydrolysis of this compound by the procedure of Example 3(e) gives N-[3-(2-amino-5-(1,3,4-thiadiazolyl)thio)propyl]-N'-methylguanidine dihydrochloride.

EXAMPLE 205

Reacting 5-chloro-3-chloromethyl-1,2,4-thiadiazole with cysteamine by the procedure of Example 1(i)(c) gives 3-[(2-aminoethyl)thiomethyl]-5-chloro-1,2,4-thiadiazole.

Using the above prepared intermediate in the procedure of Example 3 gives N-[2-(5-chloro-3-(1,2,4-thiadiazolyl)methylthio)ethyl]-N'-cyano-N''-methylguanidine.

Reacting 3-[(2-aminoethyl)thiomethyl]-5-chloro-1,2,4-thiadiazole with S-methyl-N-nitroisothiourea by the procedure of Example 2(ii) gives N-[2-(5-chloro-3-(1,2,4-thiadiazolyl)methylthio)ethyl]-N'-nitroguanidine, and with N,S-dimethyl-N'-nitroisothiourea by the procedure of Example 2(iii) gives N-[2-(5-chloro-3-(1,2,4-thiadiazolyl)methylthio)ethyl]-N'-methyl-N''-nitroguanidine.

EXAMPLE 206

Reacting 2-amino-5-(2-aminoethyl)thiomethyl-1,3,4-thiadiazole with S-methyl-N-nitroisothiourea by the procedure of Example 2 gives N-[2-(2-amino-5-(1,3,4-thiadiazolyl)methylthio)ethyl]-N'-nitroguanidine.
Treatment with hydriodic acid gives the hydroiodide salt.

EXAMPLE 207

N-Cyano-N'-methyl-N''-[3-(2-trifluoromethyl-5-(1,3,4-thiadiazolyl)thio)propyl]guanidine Using 2-trifluoromethyl-5-mercapto-1,3,4-thiadiazole as the starting material in the procedure of Example 20, the title compound is prepared.

EXAMPLE 208

N-Cyano-N'-methyl-N''-[3-(2-(1,3,4-thiadiazolyl)thio)propyl]guanidine

Using 2-mercapto-1,3,4-thiadiazole as the starting material in the procedure of Example 20 gives the title compound.

EXAMPLE 209

N-Cyano-N'-methyl-N''-[3-(3-(1,2,4-thiadiazolyl)thio)propyl]guanidine

Using 3-mercapto-1,2,4-thiadiazole as the starting material in the procedure of Example 20 gives the title compound.

EXAMPLE 210

Reacting 4-hydroxymethyl-1,2,3-thiadiazole with cysteamine by the procedure of Example 1 gives 4-[(2-aminoethyl)thiomethyl]-1,2,3-thiadiazole. From this compound by the procedures of Examples 1, 2 and 3, the following products are prepared:
2-(4-(1,2,3-thiadiazolyl)methylthio)ethylguanidine sulphate
N-nitro-N'-[2-(4-(1,2,3-thiadiazolyl)methylthio)ethyl]guanidine
N-cyano-N'-methyl-N''-[2-(4-(1,2,3-thiadiazolyl)methylthio)ethyl]guanidine.

EXAMPLE 211

Converting 5-methyl-4-(1,2,3-thiadiazole)carboxylic acid to the methyl ester and reducing the ester with lithium aluminium hydride in tetrahydrofuran gives 4-hydroxymethyl-5-methyl-1,2,3-thiadiazole.

Reacting 4-hydroxymethyl-5-methyl-1,2,3-thiadiazole with cysteamine by the procedure of Example 1 gives 4-[(2-aminoethyl)thiomethyl]-5-methyl-1,2,3-thiadiazole.

Using the above prepared compound as the starting material in the procedure of Example 3 gives N-cyano-N'-methyl-N''-[2-(5-methyl-4-(1,2,3-thiadiazolyl)methylthio)ethyl]guanidine.

By the same procedure using the following as starting materials (prepared from the corresponding carboxylic acids by the above process or, in the case of the 4-chloro substituted compound, by treatment with diborane):
5-amino-4-hydroxymethyl-1,2,3-thiadiazole
4,5-di(hydroxymethyl)-1,2,3-thiadiazole
4-hydroxy-3-hydroxymethyl-1,2,5-thiadiazole
4-chloro-3-hydroxymethyl-1,2,5-thiadiazole
the following products are obtained, respectively:
N-[2-(5-amino-4-(1,2,3-thiadiazolyl)methylthio)ethyl]-N'-cyano-N''-methylguanidine
4,5-bis-[2-(N-cyano-N'-methylguanidino)ethylthiomethyl]-1,2,3-thiadiazole
N-cyano-N'-[2-(4-hydroxy-3-(1,2,5-thiadiazolyl)methylthio)ethyl]-N''-methylguanidine
N-[2-(4-chloro-3-(1,2,5-thiadiazolyl)methylthio)ethyl]-N'-cyano-N''-methylguanidine.

Also, reacting 4-hydroxymethyl-5-methyl-1,2,3-thiadiazole with 3-mercaptopropylamine and using the resulting 4-[(3-aminopropyl)thiomethyl]-5-methyl-1,2,3-thiadiazole as the starting material in the procedure of Example 3 gives N-cyano-N'-methyl-N''-[3-(5-methyl-4-(1,2,3-thiadiazolyl)methylthio)propyl]guanidine.

EXAMPLE 212

N-[2-(2-(2-Amino-5-(1,3,4-thiadiazolyl))ethyl)thioethyl]N'-cyano-N''-methylguanidine 2-Amino-5-(1,3,4-thiadiazole)acetic acid is converted to the methyl ester and the ester is reduced with lithium aluminium hydride in tetrahydrofuran to give 2-amino-5-(2-hydroxyethyl)-1,3,4-thiadiazole. Treating with thionyl chloride gives 2-amino-5-(2-chloroethyl)-1,3,4-thiadiazole. Using this compound as the starting material in the procedure of Example 17 gives the title compound.

EXAMPLE 213

N-Cyano-N'-methyl-N''-[3-(4-(1,2,3-thiadiazolyl)methoxy)propyl]guanidine

Treating 4-hydroxymethyl-1,2,3-thiadiazole with thionyl chloride and using the resulting 4-chloromethyl-1,2,3-thiadiazole as the starting material in the procedure of Example 22 gives the title compound.

EXAMPLE 214

Using 2-amino-5-(2-aminoethyl)thiomethyl-1,3,4-thiadiazole as the starting material in the procedure of Example 18 gives N-[2-(2-amino-5-(1,3,4-thiadiazolyl)-methylthio)ethyl]-N'-cyanoguanidine.

EXAMPLE 215

Reaction of 2-amino-5-(2-aminoethyl)thiomethyl-1,3,4-thiadiazole with dimethyl-N-cyanoimidodithiocarbonate by the procedure of Example 3(c)(i) gives N-[2-(2-amino-5-(1,3,4-thiadiazolyl)methylthio)ethyl]-N'-cyano-S-methylisothiourea.

By the procedure of Example 3(c)(ii), the above prepared isothiourea is reacted with methylamine to give N-[2-(2-amino-5-(1,3,4-thiadiazolyl)methylthio)ethyl]-N'-cyano-N''-methylguanidine.

Reaction of the above prepared isothiourea with ethylamine by the procedure of Example 4 gives N-[2-(2-amino-5-(1,3,4-thiadiazolyl)methylthio)ethyl]N'-cyano-N''-ethylguanidine.

By the same procedure, using 2-(dimethylamino)ethylamine in place of ethylamine, N-[2-(2-amino-5-(1,3,4-thiadiazolyl)methylthio)ethyl]-N'-cyano-N''-(2-dimethylaminoethyl)guanidine is prepared.

EXAMPLE 216

| Ingredients | Amounts |
|---|---|
| N-[3-(2-Amino-5-(1,3,4-thiadiazolyl)-thiopropyl]-N'-cyano-N''-methylguanidine | 150 mg. |
| Lactose | 100 mg. |

The ingredients are mixed and filled into a hard gelatin capsule.

Compounds of formula I wherein A is such that there is formed together with the carbon atom shown a thiadiazole ring and Y is NH are exemplified by the following examples.

EXAMPLE 217

2-(2-Amino-5-(1,3,4-thiadiazolyl)methylamino)ethylguanidine sulfate

By the procedure of Example 34, using 2-amino-5-chloromethyl-1,3,4-thiadiazole, prepared by reacting the corresponding 5-hydroxymethyl compound with thionyl chloride, as the starting material, the title compound is prepared.

EXAMPLE 218

Reacting ethylenediamine with 2-amino-5-chloromethyl-1,3,4-thiadiazole by the procedure of Example 34, then reacting the resulting N-[2-amino-5-(1,3,4-thiadiazolyl)methyl]ethylenediamine with S-methyl-N-nitroisothiourea by the procedure of Example 2(ii) gives N-[2-(2-amino-5-(1,3,4-thiadiazolyl)methylamino)ethyl]-N'-nitroguanidine. Similarly, reaction of N-[2-amino-5-(1,3,4-thiadiazolyl)methyl]ethylenediamine with N,S-dimethyl-N'-nitroisothiourea by the procedure of Example 2(iii) gives N-[2-(2-amino-5-(1,3,4-thiadiazolyl)methylamino)ethyl]-N'-methyl-N''-nitroguanidine.

EXAMPLE 219

Ethylenediamine is reacted with 2-amino-5-chloromethyl-1,3,4-thiadiazole by the procedure of Example 34 and the resulting N-[2-amino-5-(1,3,4-thiadiazolyl)methyl]ethylenediamine is reacted with methyl isothiocyanate by the procedure of Example 3(b) to give, after chromatographing, N-methyl-N'-[2-(2-amino-5-(1,3,4-thiadiazolyl)methylamino)ethyl]thiourea. This thiourea is reacted with lead cyanamide by the procedure of Example 3(b) to give N-[2-(2-amino-5-(1,3,4-thiadiazolyl)methylamino)ethyl]-N'-cyano-N''-methylguanidine. Acid hydrolysis of this compound by the procedure of Example 3(e) gives N-[2-(2-amino-5-(1,3,4-thiadiazolyl)methylamino)ethyl]-N'-methylguanidine dihydrochloride.

EXAMPLE 220

Using ethyl isothiocyanate in place of methyl isothiocyanate in the procedure of Example 219 gives N-[2-(2-amino-5-(1,3,4-thiadiazolyl)methylamino)ethyl]-N'-cyano-N''-ethylguanidine.

By the same procedure, using propyl isothiocyanate, N-[2-(2-amino-5-(1,3,4-thiadiazolyl)methylamino)ethyl]-N'-cyano-N''-propylguanidine is prepared.

Similarly, using 2-dimethylaminoethyl isothiocyanate, the corresponding N''-(2-dimethylaminoethyl) compound is prepared.

EXAMPLE 221

Using, in the procedure of Example 219, the following chloroalkylthiadiazoles (which may be prepared by treating the corresponding hydroxyalkyl compounds with thionyl chloride):

5-chloro-3-chloromethyl-1,2,4-thiadiazole
4-chloromethyl-1,2,3-thiadiazole
3-chloromethyl-4-hydroxy-1,2,5-thiadiazole
4-chloromethyl-5-methyl-1,2,3-thiadiazole
2-amino-5-(2-chloroethyl)-1,3,4-thiadiazole
4,5-di(chloromethyl)-1,2,3-thiadiazole
the following products are obtained, respectively:
N-[2-(5-chloro-3-(1,2,4-thiadiazolyl)methylamino)ethyl]-N'-cyano-N''-methylguanidine N-cyano-N'-methyl-N''-[2-(4-(1,2,3-thiadiazolyl)methylamino)ethyl]guanidine
N-cyano-N'-[2-(4-hydroxy-3-(1,2,5-thiadiazolyl)methylamino)ethyl]-N''-methylguanidine
N-cyano-N'-methyl-N''-[2-(5-methyl-4-(1,2,3-thiadiazolyl)methylamino)ethyl]guanidine
N-[2-(2-(2-amino-5-(1,3,4-thiadiazolyl))ethylamino)ethyl]-N'-cyano-N''-methylguanidine
4,5-bis-[2-(N-cyano-N'-methylguanidino)ethylaminomethyl]-1,2,3-thiadiazole.

Using, in the procedure of Example 219, 1,3-diaminopropane in place of ethylenediamine gives N-[3-(2-amino-5-(1,2,3-thiadiazolyl)methylamino)propyl]-N'-cyano-N''-methylguanidine.

EXAMPLE 222

Using 2-amino-1,3,4-thiadiazole as the starting material in the procedure of Example 40 gives 2-(3-aminopropylamino)-1,3,4-thiadiazole.

Using 2-(3-(aminopropylamino)-1,3,4-thiadiazole as the starting material in the procedure of Example 3 gives N-cyano-N'-methyl-N''-[3-(2-(1,3,4-thiadiazolyl)amino)propyl]guanidine.

EXAMPLE 223

Using 2-(3-aminopropylamino)-1,3,4-thiadiazole as the starting material in the procedure of Example 18 gives N-cyano-N'-[3-(2-(1,3,4-thiadiazolyl)amino)propyl]guanidine.

EXAMPLE 224

Using the following compounds as starting materials in the procedure of Example 200:
3-chloro-1,2,5-thiadiazole
2-bromo-5-trifluoromethyl-1,3,4-thiadiazole
the following products are obtained, respectively:
N-cyano-N'-methyl-N''-[3-(3-(1,2,5-thiadiazolyl)amino)propyl]guanidine
N-cyano-N'-methyl-N''-[3-(5-trifluoromethyl-2-(1,3,4-thiadiazolyl)amino)propyl]guanidine.

Reaction of 3-amino-1,2,4-thiadiazole with 3-phthalimidopropyl bromide and hydrazinolysis of the product gives 3-(3-aminopropylamino)-1,2,4-thiadiazole and from this intermediate N-cyano-N'-methyl-N''-[3-(3-(1,2,4-thiadiazolyl)amino)propyl]guanidine is prepared.

EXAMPLE 225

| Ingredients | Amounts |
|---|---|
| N-[2-(2-Amino-5-(1,3,4-thiadiazolyl)methylamino)ethyl]-N'-cyano-N''-methylguanidine | 200 mg. |
| Lactose | 100 mg. |

The ingredients are mixed and filled into a hard gelatin capsule.

Compounds of formula I wherein A is such that there is formed together with the carbon atom shown a benzimidazole ring and Y is oxygen or sulphur (sulphur is preferred) are exemplified by the following examples.

EXAMPLE 226

2-(2-Benzimidazolylmethylthio)ethylguanidine sulphate

By the procedure of Example 1, the following intermediate amine salt was prepared: 2-[(2-aminoethyl)thiomethyl]benzimidazole, dihydrobromide, m.p. 242°–245° C. By the procedure of Example 1, converting this salt to the free base and then reacting with S-methylisothiouronium sulphate gives the title compound.

EXAMPLE 227

Reacting 2-[(2-aminoethyl)thiomethyl]benzimidazole with S-methyl-N-nitroisothiourea by the procedure of Example 2(ii) gives N-[2-(2-benzimidazolylmethylthio)ethyl]-N'-nitroguanidine. Treatment with hydrochloric acid gives the hydrochloride salt.

Similarly, reaction of the same starting material with N,S-dimethyl-N'-nitroisothiourea by the procedure of Example 2(iii) gives N-[2-(2-benzimidazolylmethylthio)ethyl]-N'-methyl-N''-nitroguanidine.

EXAMPLE 228

Reacting 2-[(2-aminoethyl)thiomethyl]benzimidazole with dimethyl-N-cyanoimidodithiocarbonate by the procedure of Example 3(c)(i) gives N-cyano-N'-[2-(2-benzimidazolylmethylthio)ethyl]-S-methylisothiourea. Reacting this isothiourea compound with methylamine by the procedure of Example 3(c)(ii) gives N-[2-(2-benzimidazolylmethylthio)ethyl]-N'-cyano-N''-methylguanidine. Hydrolysis of this compound by the procedure of Example 3(e) gives N-[2-(2-benzimidazolylmethylthio)ethyl]-N'-methylguanidine dihydrochloride.

EXAMPLE 229

Reacting N-cyano-N'-[2-(2-benzimidazolylmethylthio)ethyl]-S-methylisothiourea with ethylamine by the procedure of Example 4 gives N-[2-(2-benzimidazolylmethylthio)ethyl]-N'-cyano-N''-ethylguanidine.

Similarly, using propylamine in place of ethylamine, the corresponding N''-propyl compound is prepared.

Using 2-(dimethylamino)ethylamine in place of ethylamine gives the corresponding N''-(2-dimethylaminoethyl) compound.

EXAMPLE 230

N-[2-(2-(2-Benzimidazolyl)ethyl)thioethyl]-N'-cyano-N''-methylguanidine

Using 2-(2-chloroethyl)benzimidazole, prepared by treating 2-(2-hydroxyethyl)benzimidazole with thionyl chloride, as the starting material in the procedure of Example 17 gives the title compound.

EXAMPLE 231

Using 2-chloromethylbenzimidazole, prepared by reacting 2-hydroxymethylbenzimidazole with thionyl chloride, as the starting material in the procedure of Example 22 gives N-[3-(2-benzimidazolylmethoxy)propyl]-N'-cyano-N''-methylguanidine. Treatment with citric acid in ethanol gives the citrate salt.

EXAMPLE 232

By the procedure of Example 20 using 2-mercaptobenzimidazole as the starting material, N-[3-(2-benzimidazolylthio)propyl]-N'-cyano-N''-methylguanidine is prepared.

EXAMPLE 233

Using 2-[(2-aminoethyl)thiomethyl]benzimidazole as the starting material in the procedure of Example 18 gives N-[2-(2-benzimidazolylmethylthio)ethyl]-N'-cyanoguanidine.

EXAMPLE 234

| Ingredients | Amounts |
| --- | --- |
| N-[2-(2-Benzimidazolylmethylthio)-ethyl]-N'-cyano-N''-methyl-guanidine | 150 mg. |
| Sucrose | 75 mg. |
| Starch | 25 mg. |
| Talc | 5 mg. |
| Stearic acid | 2 mg. |

The ingredients are mixed and filled into a hard gelatin capsule.

Compounds of formula I wherein A is such that there is formed together with the carbon atom shown a benzimidazole ring and Y is NH are exemplified by the following examples.

EXAMPLE 235

2-(2-benzimidazolylmethylamino)ethylguanidine sulphate

Using 2-chloromethylbenzimidazole as the starting material in the procedure of Example 34, the title compound is prepared.

EXAMPLE 236

Reacting ethylenediamine with 2-chloromethylbenzimidazole by the procedure of Example 34, then using the resulting N-(2-benzimidazolylmethyl)ethylenediamine as the starting material in the procedures of Examples 35 gives N-[2-(2-benzimidazolylmethylamino)ethyl]-N'-nitroguanidine and N-[2-(2-benzimidazolylmethylamino)-ethyl]-N'-methyl-N''-nitroguanidine.

EXAMPLE 237

Reacting N-(2-benzimidazolylmethyl)ethylenediamine with N-cyano-N',S-dimethylisothiourea by the procedure of Example 36 gives N-[2-(2-benzimidazolylmethylamino)ethyl]-N'-cyano-N''-methylguanidine. Treating with hydrobromic acid gives the hydrobromide salt. Hydrolysis of this compound by the procedure of Example 3(e) gives N-[2-(2-benzimidazolylmethylamino)-ethyl]-N'-methylguanidine trihydrochloride.

EXAMPLE 238

Reacting N-(2-benzimidazolylmethyl)ethylenediamine with ethyl isothiocyanate by the procedure of Example 3(b), then chromatographing and reacting the resulting thiourea with lead cyanamide by the procedure of Example 3(b) gives N-[2-(2-benzimidazolylmethylamino)ethyl]-N'-cyano-N''-ethylguanidine.

Similarly, using the following isothiocyanates in place of ethyl isothiocyanate:
propyl isothiocyanate
2-dimethylaminoethyl isothiocyanate
the following products are obtained, respectively:
N-[2(2-benzimidazolylmethylamino)ethyl]-N'-cyano-N''-propylguanidine
N-[2-(2-benzimidazolylmethylamino)ethyl]-N'-cyano-N''-(2-dimethylaminoethyl)guanidine.

Using in the above procedure, 2-[(3-aminopropyl)aminomethyl]benzimidazole (prepared by reacting 2-chloromethylbenzimidazole with 1,3-diaminopropane) and methyl isothiocyanate, the product is N-[3-(2-benzimidazolylmethylamino)propyl]-N'-cyano-N''-methylguanidine.

EXAMPLE 239

Using 2-aminobenzimidazole as the starting material in the procedure of Example 40 gives 2-(3-aminopropylamino)benzimidazole as the intermediate and N-[3-(2-benzimidazolylamino)propyl]-N'-cyano-N''-methylguanidine as the product.

EXAMPLE 240

Using 2-(3-aminopropylamino)benzimidazole as the starting material in the procedure of Example 18 gives N-[3-(2-benzimidazolylamino)propyl]-N'-cyanoguanidine.

EXAMPLE 241

N-[2-(2-(2-Benzimidazolyl)ethylamino)ethyl]-N'-cyano-N''-methylguanidine

Reacting 2-(2-chloroethyl)benzimidazole with ethylenediamine by the procedure of Example 34, then reacting the resulting N-[2-(2-benzimidazolyl)ethyl]-ethylenediamine with N-cyano-N',S-dimethylisothiourea by the procedure of Example 3(a) gives the title compound.

EXAMPLE 242

| Ingredients | Amounts |
| --- | --- |
| N-[2-(2-Benzimidazolylmethylamino)-ethyl]-N'-cyano-N''-methylguanidine | 200 mg. |
| Lactose | 100 mg. |

The ingredients are mixed and filled into a hard gelatin capsule.

Compounds of formula I wherein A is such that there is formed together with the carbon atom shown a 5,6,7,8-tetrahydroimidazo[1,5-a]pyridine ring and Y is oxygen or sulphur (sulphur is preferred) are exemplified by the following examples.

EXAMPLE 243

2-[3-(5,6,7,8-Tetrahydroimidazo[1,5-a]pyridyl)methylthio]-ethylguanidine sulphate A solution of 1.58 molar n-butyl lithium in n-hexane (49 ml.) was added over 0.5 hour to a stirred solution of 5,6,7,8-tetrahydroimidazo[1,5-a]pyridine (8.9 g.) in dry ether at −60° under nitrogen. After 3 hours, gaseous formaldehyde generated by the thermal condensation of paraformaldehyde (6.9 g.) was passed into the red solution. The mixture was allowed to warm to room temperature overnight, acidified with hydrochloric acid and extracted with chloroform. The aqueous layer was basified with an excess of saturated sodium carbonate solution and extracted with chloroform. Concentration and recrystallisation of the residue from ethanol-ethyl acetate-petroleum ether afforded 3-hydroxymethyl-5,67,8-tetrahydroimidazo[1,5-a]pyridine (7.7 g.) m.p. 188°–199°.

Reacting 3-hydroxymethyl-5,6,7,8-tetrahydroimidazo[1,5-a]pyridine with cysteamine hydrochloride by the procedure of Example 1 gives 3-[(2-aminoethyl)thiomethyl]-5,6,7,8-tetrahydroimidazo[1,5-a]pyridine.

Reacting the above prepared intermediate with S-methylisothiouronium sulphate by the procedure of Example 1 gives the title compound.

EXAMPLE 244

Reacting 3-[(2-aminoethyl)thiomethyl]-5,6,7,8-tetrahydroimidazo[1,5-a]pyridine with S-methyl-N-nitroisothiourea by the procedure of Example 2(ii) gives N-nitro-N'-[2-(3-(5,6,7,8-tetrahydroimidazo[1,5-a]-pyridyl)methylthio)ethyl]guanidine. Treating with hydrobromic acid gives the hydrobromide salt. Reaction of the same starting material with N,S-dimethyl-N'-nitroisothiourea by the procedure of Example 2(iii) gives N-methyl-N'-nitro-N''-[2-(3-(5,6,7,8-tetrahydroimidazo[1,5-a]pyridyl)methylthio)ethyl]guanidine.

EXAMPLE 245

Reacting 3-[(2aminoethyl)thiomethyl]-5,6,7,8-tetrahydroimidazo[1,5-a]pyridine with dimethyl-N-cyanoimidodithiocarbonate by the procedure of Example 3 (c)(i) gives N-cyano-N'-[2-(3-(5,6,7,8-tetrahydroimidazo[1,5-a]pyridyl)methylthio)ethyl]-S-methylisothiourea.

Reacting this isothiourea compound with methylamine by the procedure of Example 3(c)(ii) gives N-cyano-N'-methyl-N''-[2-(3-(5,6,7,8-tetrahydroimidazo[1,5-a]pyridyl)methylthio)ethyl]guanidine. Acid hydrolysis of this compound by the procedure of Example 3(e) gives N-methyl-N'-[2-(3-(5,6,7,8-tetrahydroimidazo[1,5-a]pyridyl)methylthio)ethyl]guanidine dihydrochloride.

EXAMPLE 246

Reacting N-cyano-N'-[2-(3-(5,6,7,8-tetrahydroimidazo[1,5-a]pyridyl)methylthio)ethyl]-S-methylisothiourea with ethylamine by the procedure of Example 4 gives N-cyano-N'-ethyl-N''-[2-(3-(5,6,7,8-tetrahydroimidazo[1,5-a]pyridyl)methylthio)ethyl]-guanidine.

By the same procedure, using propylamine in place of ethylamine, the corresponding N'-propyl compound is prepared.

Also, using 2-(dimethylamino)ethylamine, the corresponding N'-(2-dimethylaminoethyl) compound is prepared.

EXAMPLE 247

N-Cyano-N'-methyl-N''-[3-(3-(5,6,7,8-tetrahydroimidazo[1,5-a]pyridyl)methoxy)propyl]guanidine By the procedure of Example 22 using as the starting material 3-chloromethyl-5,6,7,8-tetrahydroimidazo[1,5-a]pyridine, prepared by treating the 3-hydroxymethyl compound with thionyl chloride, the title compound is prepared.

EXAMPLE 248

By the procedure of Example 18, using 3-[(2-aminoethyl)thiomethyl]-5,6,7,8-tetrahydroimidazo[1,5-a]pyridine as the starting material, N-cyano-N'-[2-(3-(5,6,7,8-tetrahydroimidazo[1,5-a]pyridyl)methylthio)ethyl]-guanidine is prepared.

EXAMPLE 249

| Ingredients | Amounts |
| --- | --- |
| N-Cyano-N'-methyl-N''-[2-(3-(5,6,7,8-tetrahydroimidazo]1,5-a]pyridyl)-methylthio)ethyl]guanidine | 200 mg. |
| Lactose | 100 mg. |

The ingredients are mixed and filled into a hard gelatin capsule.

Compounds of formula I wherein A is such that there is formed together with the carbon atom shown a 5,6,7,8-tetrahydroimidazo[1,5-a]pyridine ring and Y is NH are exemplified by the following examples.

EXAMPLE 250

2-[3-(5,6,7,8-Tetrahydroimidazo[1,5-a]pyridyl)methylamino]ethylguanidine sulphate Using 3-chloromethyl-5,6,7,8-tetrahydroimidazo[1,5-a]pyridine, prepared by treating the corresponding hydroxymethyl compound with thionyl chloride, as the starting material in the procedure of Example 34 gives the title compound.

EXAMPLE 251

Reacting 3-chloromethyl-5,6,7,8-tetrahydroimidazo[1,5-a]pyridine with ethylenediamine by the procedure of Example 34 gives N-[3-(5,6,7,8-tetrahydroimidazo[1,5-a]pyridyl)methyl]ethylenediamine. Reacting this intermediate with S-methyl-N-nitroisothiourea by the procedure of Example 2(ii) gives N-nitro-N''-[2-(3-(5,6,7,8-tetrahydroimidazo[1,5-a]pyridyl)methylamino)ethyl]-guanidine. Treating with hydrochloric acid gives the hydrochloride salt.

Reaction of the above intermediate with N,S-dimethyl-N'-nitroisothiourea by the procedure of Example 2-(iii) gives N-methyl-N'-nitro-N''-[2-(3-(5,6,7,8-tetrahydroimidazo[1,5-a]pyridyl)methylamino)ethyl]guanidine.

EXAMPLE 252

Using 3-chloromethyl-5,6,7,8-tetrahydroimidazo[1,5-a]pyridine as the starting material in the procedure of Example 36 gives N-cyano-N'-methyl-N''-[2-(3-(5,6,7,8-tetrahydroimidazo[1,5-a]pyridyl)methylamino)ethyl]-guanidine. Acid hydrolysis by the procedure of Example 3(e) gives N-methyl-N'-[2-(3-(5,6,7,8-tetrahydroimidazo[1,5-a]pyridyl)methylamino)ethyl]guanidine trihydrochloride.

EXAMPLE 253

Reacting N-[3-(5,6,7,8-tetrahydroimidazo[1,5-a]pyridyl)methyl]ethylenediamine with ethyl isothiocyanate by the procedure of Example 3(b), then chromatographing gives N-ethyl-N'-[2-(3-(5,6,7,8-tetrahydroimidazo[1,5-a]pyridyl)methylamino)ethyl]thiourea. Reacting this thiourea compound with lead cyanamide by the procedure of Example 3(b) gives N-cyano-N'-ethyl-N''-[2-(3-(5,6,7,8-tetrahydroimidazo[1,5-a]pyridyl)methylamino)ethyl]guanidine.

Using in place of ethyl isothiocyanate the following:
propyl isothiocyanate
2-dimethylaminoethyl isothiocyanate
the following products are obtained, respectively:
N-cyano-N'-propyl-N''-[2-(3-(5,6,7,8-tetrahydroimidazo[1,5-a]pyridyl)methylamino)ethyl]guanidine
N-cyano-N'-(2-dimethylaminoethyl)-N''-[2-(3-(5,6,7,8-tetrahydroimidazo[1,5-a]pyridyl)methylamino)ethyl]guanidine.

EXAMPLE 254

N-Cyano-N'-methyl-N''-[3-(3-(5,6,7,8-tetrahydroimidazo[1,5-a]pyridyl)methylamino)propyl]guanidine Using, as the starting materials in the procedure of Example 36, 1,3-diaminopropane and 3-chloromethyl-5,6,7,8-tetrahydroimidazo[1,5-a]pyridine, the title product is prepared.

EXAMPLE 255

| Ingredients | Amounts |
|---|---|
| N-Cyano-N'-methyl-N''-[2-(3-(5,6,7,8-tetrahydroimidazo[1,5-a]pyridyl)-methylamino)ethyl]guanidine | 200 mg. |
| Lactose | 100 mg. |

The ingredients are mixed and filled into a hard gelatin capsule.

The pharmaceutical compositions prepared as in foregoing examples are administered to a subject within the dose ranges given hereabove to inhibit H-2 histamine receptors.

In the foregoing examples, the temperatures are in degrees Centigrade.

What we claim is:

1. A compound of the formula:

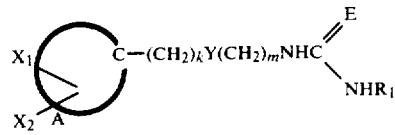

wherein A is such that there is formed together with the carbon atom shown an unsaturated heterocyclic nucleus, said unsaturated heterocyclic nucleus being a benzimidazole or 3-(5,6,7,8-tetrahydroimidazo[1,5-a]pyridine) ring; $X_1$ is hydrogen, lower alkyl, hydroxyl, trifluoromethyl, benzyl, halogen, amino or

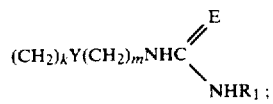

$X_2$ is hydrogen or when $X_1$ is lower alkyl, lower alkyl or halogen; k is 0 to 2 and m is 2 or 3, provided that the sum of k and m is 3 or 4; Y is oxygen, sulphur or NH; E is $NR_2$; $R_1$ is hydrogen, lower alkyl or di-lower alkylamino-lower alkyl; and $R_2$ is hydrogen, nitro or cyano, or a pharmaceutically acceptable addition salt thereof.

2. A compound of claim 1 wherein Y is oxygen or sulphur.

3. A compound of claim 1 wherein Y is NH.

4. A compound of claim 1 wherein said unsaturated heterocyclic nucleus is benzimidazole or 3-(5,6,7,8-tetrahydroimidazo[1,5-a]pyridine) and $R_2$ is hydrogen or nitro.

5. A compound of claim 4 wherein k is 1 and m is 2.

6. A compound of claim 1, said compound being N-[2-(2-benzimidazolylmethylthio)ethyl]-N'-cyano-N''-methylguanidine.

7. A compound of claim 1, said compound being N-cyano-N'-methyl-N''-[2-(3-(5,6,7,8-tetrahydroimidazo[1,5-a]pyridyl)methylthio)ethyl]guanidine.

* * * * *